US009460246B2

(12) United States Patent
Williams

(10) Patent No.: US 9,460,246 B2
(45) Date of Patent: *Oct. 4, 2016

(54) DEVICE FOR PREDICTING NON-LINEAR, TIME-DEPENDENT RESPONSES OF A COMPONENT OF A SYSTEM TO AN INPUT INTO THE SYSTEM

(71) Applicant: Arrapoi, Inc., Redwood City, CA (US)

(72) Inventor: Glenn A. Williams, Redwood City, CA (US)

(73) Assignee: ARRAPOI, INC., Redwood City, CA (US)

( * ) Notice: Subject to any disclaimer, the term of this patent is extended or adjusted under 35 U.S.C. 154(b) by 594 days.

This patent is subject to a terminal disclaimer.

(21) Appl. No.: 13/962,961

(22) Filed: Aug. 9, 2013

(65) Prior Publication Data

US 2014/0172383 A1    Jun. 19, 2014

Related U.S. Application Data

(63) Continuation of application No. 13/717,644, filed on Dec. 17, 2012, now Pat. No. 8,554,712.

(51) Int. Cl.
*G06F 17/50*      (2006.01)
*G06F 17/17*      (2006.01)
(Continued)

(52) U.S. Cl.
CPC ........... *G06F 17/5009* (2013.01); *G06F 17/17* (2013.01); *G06N 5/02* (2013.01); *G06F 19/12* (2013.01); *G06F 19/704* (2013.01)

(58) Field of Classification Search
CPC .... G06F 17/5009; G06F 17/17; G06F 19/12; G06F 19/704; G06N 5/002; G06N 3/00; G06N 7/00; G06N 7/06
See application file for complete search history.

(56) References Cited

U.S. PATENT DOCUMENTS 8,554,712 B1    10/2013   Williams
2005/0075274 A1*   4/2005   Willmann ........... G06F 19/3437
                                                       514/1

(Continued)

FOREIGN PATENT DOCUMENTS

WO   PCT/US2013/073654    12/2012
WO   PCT/US2014/058696    10/2013

OTHER PUBLICATIONS

Prediction of peptide bonding affinity: kernel methods for nonlinear modeling, by Bergeron, published Aug. 2011.*

(Continued)

*Primary Examiner* — Stanley K Hill
*Assistant Examiner* — Thomas Fink
(74) *Attorney, Agent, or Firm* — Brian S. Boyer; Syndicated Law, PC

(57) ABSTRACT

Non-mechanistic, differential-equation-free approaches for predicting a particular non-linear, response of a system to a given input are provided in the form of systems, methods, and devices. These approaches are generally directed to a non-compartmental method of predicting a non-linear, time-dependent response of a component of a system to an input into the system. The systems, methods, and devices provide the ability to (i) reduce the cost of research and development by offering an accurate modeling of heterogeneous and complex physical systems; (ii) reduce the cost of creating such systems and methods by simplifying the modeling process; (iii) accurately capture and model inherent nonlinearities in cases where sufficient knowledge does not exist to a priori build a model and its parameters; and, (iv) provide one-to-one relationships between model parameters and model outputs, addressing the problem of the ambiguities inherent in the current, state-of-the-art systems and methods.

30 Claims, 16 Drawing Sheets

(51) Int. Cl.
*G06N 5/02* (2006.01)
*G06F 19/00* (2011.01)
*G06F 19/12* (2011.01)

(56) References Cited

U.S. PATENT DOCUMENTS

| | | | |
|---|---|---|---|
| 2005/0143927 A1 | 6/2005 | Cammia et al. | |
| 2007/0287144 A1 | 12/2007 | Kouchi et al. | |
| 2008/0027651 A1* | 1/2008 | Siekmeier | G06F 19/707 |
| | | | 702/19 |
| 2008/0174842 A1 | 7/2008 | Cromwell et al. | |
| 2009/0138286 A1 | 5/2009 | Linder et al. | |
| 2010/0185426 A1 | 7/2010 | Ganesan et al. | |
| 2010/0312508 A1 | 12/2010 | Mott et al. | |
| 2011/0119212 A1 | 5/2011 | De Bruin et al. | |
| 2011/0166883 A1 | 7/2011 | Palmer et al. | |
| 2011/0295567 A1 | 12/2011 | Thiesson et al. | |
| 2011/0313777 A1 | 12/2011 | Baeckstroem et al. | |
| 2012/0124051 A1 | 5/2012 | Lin et al. | |

OTHER PUBLICATIONS

Volterra Series in Pharmacokinetics and Pharmacodynamics, by Verotta, published 2003.*
Nonlinear Models for Repeated Measurement Data, by Davidian, published 1995.*
Search Report and the written opinion for PCT/US2014/058696, Dec. 30, 2014.
U.S. Appl. No. 13/962,962, Williams, filed Dec. 17, 2012.
U.S. Appl. No. 14/046,918, Williams, filed Oct. 4, 2013.
U.S. Appl. No. 14/084,608, Williams, filed Oct. 4, 2013.
Search report for PCT/US2013/073654, Dec. 17, 2012.
Barditch-Covo, P., et al. Phase I/II trail of the pharmacokinetics, safety, and antiretroviral activity of tenofovir disoproxil fumarate in human immunodeficiency virus-Infected adults. Antimicrobal agents and chemotherapy 45(10): 2733-2739 (Oct. 2001).
Bergman, A., et al. Dose-proportionality of a final market image sitagliptin formulation, an oral dipeptidyl peptidase-4 inhibitor, in healthy volunteers. Biopharmaceutics & Drug Disposition 307-313 (2007).
Bonate, P.L. Pharmacokinetic-pharmacodynamic modeling and simulation, 2nd Edition. Springer New York 20-41 (2002).
Bourne, D.W.A. Mathematical modeling of pharmacokinetic data. Lancaster P.A., Technomic Publishing 62-63 (1995).
Bronzino, J.D. The Biomedical Engineering Handbook, 2nd Edition, vol. II. Washington D.C. CRC Press LLC Chapter 159 (2002).
Chittick, G.E., et al. Pharmacokinetics of tenofovir disoproxil fumarate and ritonavir-boosted saquinavir mesylate administered alone or in combination at steady state. Antimicrobial agents and Chemotherapy 50(4): 1304-1310 (Apr. 2006).
Clark, D.P. Ex vivo biomarkers: functional tools to guide targeted drug development and therapy. Expert Rev Mol Diagn 9(8): 787-794 (2009).
Cobelli, C., et al. Parameter and structural identifiability concepts and ambiguities: a criticial review and analysis. Am J Physiol Regul Integr Comp Physiol 239: R7-R24 (1980).
Czock, D., et al. Mechanism-based pharmacokinetics-pharmacodynamic modeling of antimicrobial drug effects. J Pharmacokinet Pharmacodyn 34: 727-751 (2007).
Danhof, M., et al. Mechanism-based pharmacokinetic-pharmacodynamic modeling: biophase distribution, receptor theory, and dynamical systems analysis. Annu Rev Pharmcol Toxicol 47: 357-400 (2007).
Dayneka et al. Comparison of four basic modles of indirect pharmacodynamics responses. Journal of pharmacokinetics and biopharmaceutics 21(4): 457-478 (1993).
Deeb, O. Recent applications of quantitative structure-activity relationships in drug design. Medicinal Chemistry and Drug Design 55-82 (Apr. 2012).
Droste, J.A.H., et al. Pharmacokinetic study of tenofovir disoproxil fumarate combined with rifampin in healthy volunteers. Antimicrobial Agents and Chemotherapy 49(2): 680-684 (Feb. 2005).
Dunne, A. Jana: A new iterative polyexponential curve stripping program. Computer Methods and Programs in Biomedicine 20: 269-275 (1985).
Duwal, S., et al. Pharmacokinetics and Pharmacodynamics of the reverse transcriptase nhibitor tenofovir and prophylactic efficacy against HIV-1 Infection. PLoS One 7(7): 1-14 (Jul. 2012).
Dyson, R.D., et al. Analysis of exponential curves by a method of moments, with special attention to sedimentation equilibrium and fluorescence decay. Biochemistry 10(17): 3233-3241 (1971).
Garner, C.R., et al. The phase 0 microdosing concept. Br J Clin Pharmcol 61(4): 367-370 (2006).
Gramatica, P. On the Development and Validation of QSAR Models Computational Toxicology: vol. II. Methods in Molecular Biology 930, Springer Protocols, Humana Press 499-526 (2013).
Generaux, C.N., et al. Compartmental and enzyme kinetic modeling to elucidate the Biotransformation pathway of a centrally acting antitrypanosomal prodrug. Drug Metab Dispos 45(10): 518-528 (Feb. 2013).
Kitamura, R. Application of models of activity behavior for activity based demand forecasting. Kyoto University (1996) [online] URL: http://media.tmiponline.org/clearinghouse/abtf/kitamura.pdf [retrieved Feb. 15, 2013].
Mager, D.E., et al. Diverisyt of mechanism-based pharmacodynamic models. Drug Metabolism and Disposition 31(5): 510-518 (2003).
Mamas, M., et al. The role of metabolites and metabolomics in clinically applicable biomarkers of disease. Archives of Toxicology 85: 5-17 (2011).
Pascual, B., et al. Comparative study of four different pharmacokinetic computer programs: Case study of a factor viii preparation. Eur J Clin Pharmacol 52: 59-64 (1997).
Press, W.H., et al. Numerical recipes in C: the art of scientific computing, second edition. Cambridge Univerity Press 394-402 (2002).
Sobol, W.T. Analysis of variance for 'component stripping' decomposition of multiexponential curves. Comput Meth Prog Bio 39: 243-257 (1993).
Von Kleist, M. et al. Drug-class specific impact of antivirals on the reproductive capacity of HIV. PLoS Computational Biology 6(3): 1-13 (Mar. 2010).
Walsh, R. Alternative perspectives of enzyme kinetic modeling. Medicinal Chemistry and Drug Design. InTech Croatia 357-372 (2012).
Walter, E. On the identifiability and distinguishability of nonlinear parametric models. Math Comput Simulat 42: 125-134 (1996).
Yu, T., et al. Quantification and Deconvolution of Asymmetric LC-MS Peaks Using the Bi-Gaussian Mixture Model and Statistical Model Selection. BMC Bioinformatics 11: 10 pages (2010).

* cited by examiner

DEVICE FOR PREDICTING NON-LINEAR, TIME-DEPENDENT RESPONSES OF A COMPONENT OF A SYSTEM TO AN INPUT INTO THE SYSTEM

BACKGROUND

1. Field of the Invention

The teachings generally relate to a non-mechanistic, differential-equation-free approach for predicting a particular non-linear, response of a system to a given input.

2. Description of the Related Art

Research and development has historically relied on physical modeling to develop new technologies. Given the speed at which computers can perform computations, and the vast amount of computer memory available, computer modeling allows us to speed-up and reduce costs of research by facilitating the creation of a large number of simulations over a wide range of physical scales very quickly. As with physical modeling, computer modeling and simulation deals with first characterizing and then predicting input-response type relationships. What type of reaction will occur between two chemicals? What is the flow response when a given amount of water is introduced into a particular porous media? How will the components of a watershed - - - rivers, reservoirs, aquifers, etc. - - - react when subjected to a given rainfall or contamination event? How will a person's blood glucose level respond to a given meal? How will a diseased tissue respond to a drug regimen? These are all input-response-type questions that can be addressed through mathematical/computational modeling and simulation. Generally speaking, this can be referred to as "input-response modeling". In the field of drug design, this can also be referred to as "dose-response modeling." An accurate model will give researchers a way of running simulations to quickly observe and test a large number of complex input-response phenomena that might be too costly and time-consuming to observe and test in a real-world setting.

The reliance on physical modeling can be very expensive, which makes the use of computer modeling an attractive way to reduce costs. For example, the average drug developed by a major pharmaceutical company costs at least $4 billion, and it can be as much as $11 billion. The range of money spent is quite wide, for example, as AstraZeneca has spent about $12 billion in research money for every new drug approved; Eli Lilly spent about $4.5 billion per drug; and, Amgen has spent about $3.7 billion per drug. The costs are so high, at least in part, because single clinical trial can cost $100 million, and the combined cost of manufacturing and clinical testing for some drugs can add up to $1 billion. Computer modeling of drugs, if improved such that it can be done efficiently and effectively, can cut costs and help make the business of drug discovery more attractive. Other industries, of course, can also benefit from such efficient and effective computer modeling methods.

State-of-the-art systems and methods, however, typically use mechanistic computer models to try and avoid the costs of physical modeling. Unfortunately, such models can be very complex, insufficient and ambiguous, and moreover, lacking in accuracy. Such models use established empirical formulas as "first principles" that provide the framework to make "mechanistic" predictions. Complex biological systems can be modeled, for example, using laboratory experiments to establish such first-principle-type relationships between components of the system. For example, laboratory experiments can be used to determine the ways in which a certain disease progresses in the human body, and this can be used to help predict how effective a drug might be in stopping, or slowing down, the progression of a disease.

Unfortunately, the current, state-of-the-art approaches have some serious limitations. There are problems, for example, in dealing with heterogeneous and complex systems, in that the models fail by insufficiently characterizing the systems. Predicting the flow of rainfall through the ground to an adjacent stream, for example, involves a complex and heterogeneous combination of media types in the ground. The variations throughout the media make it difficult-to-impossible to apply Darcy's Law accurately in such a complex system. And, although possible in theory, accurately identifying and modeling such complex and heterogeneous media throughout the system is often considered cost prohibitive, as well as time prohibitive in many cases. As the systems become more mechanistically complex, of course, we need more empirical relationships and a more complex model. Hydraulic conductivity mechanisms may not be enough, for example, as there can also be chemical reaction mechanisms affecting the movement of the fluids. Human biological systems are examples of highly complex systems that are difficult to scale from the lab to the human body, as measurements that can be taken in the lab may not be obtainable in the human body, for example. In predicting the response of a tumor to a drug, for example, measuring in vitro or ex vivo tumor size and growth in small time scales is one thing, but getting such in vivo measurements can be difficult-to-impossible. In addition, a system may have nonlinearities that need to be addressed, requiring further and often futile attempts at adjusting the mechanistic model. Moreover, current models often cannot map input properties to model parameters. This is because they lack the necessary one-to-one relationships between model parameters and model output. This lack of specificity results in an ambiguity between model parameters and output that makes it impossible to get unique input-response relationships, such that the same input can produce a wide range of responses, or many different inputs could produce the same response.

Accordingly, one of skill will appreciate a data-based, non-mechanistic, differential-equation-free approach for predicting a particular response of a system to a given input. In particular, one of skill will appreciate having the ability to (i) reduce the cost of research and development by offering an accurate modeling of heterogeneous and complex physical systems; (ii) reduce the cost of creating such systems and methods by simplifying the modeling process; (iii) accurately capture and model inherent nonlinearities in cases where sufficient knowledge does not exist to a priori build a model and its parameters; and, (iv) provide one-to-one relationships between model parameters and model outputs, addressing the problem of the ambiguities inherent in the current, state-of-the-art systems and methods.

SUMMARY

The teachings generally relate to a non-mechanistic, differential-equation-free approach for predicting a particular response of a system to a given input. In some embodiments, the teachings are generally directed to a non-compartmental method of predicting a time-dependent response of a component of a system to an input into the system. The method can comprise identifying the system, the component, the input, and the time-dependent response; wherein, the input includes a set of actual inputs and a test input, and the time-dependent response includes a set of time-dependent actual responses and a test response; obtaining the set of time-dependent actual responses of the component to the set of actual inputs; and, using the set of actual inputs and the set of time-dependent actual responses to provide a model for predicting the test response to the test input, the model comprising the formula:

$$C(t) = [M_0^0 + M_0^1(\text{kernel})] + \qquad (9)$$

$$[M_1^0 + M_1^1(\text{kernel})] \left\{ \frac{1 - e^{-[N_1^0 + N_1^1(\text{kernel})]t}}{1 + (e^K - 2)e^{-[N_1^0 + N_1^1(\text{kernel})]t}} \right\} + \ldots +$$

$$[M_n^0 + M_n^1(\text{kernel})] \left\{ \frac{1 - e^{-[N_n^0 + N_n^1(\text{kernel})]t}}{1 + (e^K - 2)e^{-[N_n^0 + N_n^1(\text{kernel})]t}} \right\}$$

wherein,
$M_0^0, \ldots, M_n^0$ and $M_0^1, \ldots, M_n^1$ are overall scaling parameters;
$N_1^0, \ldots, N_n^0$ and $N_1^1, \ldots, N_n^1$ are exponential scaling parameters;
n ranges from 1 to 4;
K is an overall shifting parameter; and,
C(t) is the time-dependent response to the test input at time t;
and, $$\text{kernel} \equiv \frac{1 - e^{-\alpha_p C_0}}{1 + (e^{K_p} - 2)e^{-\alpha_p C_0}};$$

wherein, $C_O$ is the initial amount of the input; $K_p$ is a shifting parameter related to $C_O$; and, $\alpha_p$ is shifting and scaling parameter related to $C_O$.

The teachings include a non-compartmental method of predicting a time-dependent response of a component of a mammalian system to an input into the system. And, it should be appreciated that the response can be measured in vivo, in vitro, or ex vivo, in some embodiments. The methods can also comprise selecting a component of the system, the component selected from the group consisting of a cell, a tissue, an organ, a DNA, a virus, a protein, an antibody, a bacteria; selecting a set of actual inputs, the set of actual inputs having an element selected from the group consisting of a DNA, a virus, a protein, an antibody, a bacteria, a chemical, a dietary supplement, a nutrient, and a drug; obtaining a set of time-dependent actual responses of the component to the set of actual inputs; and, using the set of actual inputs and the set of time-dependent actual responses to provide a model for predicting a test response to a test input, the model comprising the formula $$C(t) = [M_0^0 + M_0^1(\text{kernel})] + \qquad (9)$$

$$[M_1^0 + M_1^1(\text{kernel})] \left\{ \frac{1 - e^{-[N_1^0 + N_1^1(\text{kernel})]t}}{1 + (e^K - 2)e^{-[N_1^0 + N_1^1(\text{kernel})]t}} \right\} + \ldots +$$

$$[M_n^0 + M_n^1(\text{kernel})] \left\{ \frac{1 - e^{-[N_n^0 + N_n^1(\text{kernel})]t}}{1 + (e^K - 2)e^{-[N_n^0 + N_n^1(\text{kernel})]t}} \right\}$$

wherein,
$M_0^0, \ldots, M_n^0$ and $M_0^1, \ldots, M_n^1$ are overall scaling parameters;
$N_1^0, \ldots, N_n^0$ and $N_1^1, \ldots, N_n^1$ are exponential scaling parameters;
n ranges from 1 to 4;
K is an overall shifting parameter; and,
C(t) is the time-dependent response to the test input at time t;
and, $$\text{kernel} \equiv \frac{1 - e^{-\alpha_p C_0}}{1 + (e^{K_p} - 2)e^{-\alpha_p C_0}};$$

wherein, $C_O$ is the initial amount of the test input; $K_p$ is a shifting parameter related to $C_O$; and, $\alpha_p$ is shifting and scaling parameter related to $C_O$.

In some embodiments, the teachings are directed to a device for predicting a time-dependent response of a component of a physical system to an input into the system. In these embodiments, the device can comprise a processor; a database for storing a set of actual input data, a set of time-dependent actual response data, test input data, and time-dependent test response data on a non-transitory computer readable medium; an enumeration engine on a non-transitory computer readable medium to parameterize a non-compartmental model for predicting a test response to a test input, the non-compartmental model comprising the formula $$C(t) = [M_0^0 + M_0^1(\text{kernel})] + \qquad (9)$$

$$[M_1^0 + M_1^1(\text{kernel})] \left\{ \frac{1 - e^{-[N_1^0 + N_1^1(\text{kernel})]t}}{1 + (e^K - 2)e^{-[N_1^0 + N_1^1(\text{kernel})]t}} \right\} + \ldots +$$

$$[M_n^0 + M_n^1(\text{kernel})] \left\{ \frac{1 - e^{-[N_n^0 + N_n^1(\text{kernel})]t}}{1 + (e^K - 2)e^{-[N_n^0 + N_n^1(\text{kernel})]t}} \right\}$$

wherein,
$M_0^0, \ldots, M_n^0$ and $M_0^1, \ldots, M_n^1$ are overall scaling parameters;
$N_1^0, \ldots, N_n^0$ and $N_1^1, \ldots, N_n^1$ are exponential scaling parameters;
n ranges from 1 to 4;
K is an overall shifting parameter; and,
C(t) is the time-dependent response to the test input at time t;
and, $$\text{kernel} \equiv \frac{1 - e^{-\alpha_p C_0}}{1 + (e^{K_p} - 2)e^{-\alpha_p C_0}};$$

wherein, $C_O$ is the initial amount of the test input; $K_p$ is a shifting parameter related to $C_O$; and, $\alpha_p$ is shifting and scaling parameter related to $C_O$;

and, a transformation module on a non-transitory computer readable medium to transform the test data into the time-dependent response data using the non-compartmental model.

The systems can be virtually any physical or non-physical system known to one of skill in which that person of skill may want to predict a particular response of the system to a given input. In some embodiments, the system can be an environmental system, and the component can be selected from the group consisting of air, water, and soil. In some embodiments, the system can be a mammal, and the component can be selected from the group consisting of a cell, a tissue, an organ, a DNA, a virus, a protein, an antibody, a bacteria. In some embodiments, the system can be a chemical system, a biological system, a mechanical system, an electrical system, a financial system, a sociological system, a political system, or a combination thereof. As such, the teachings provided herein include general methods of predicting a particular response of any such system to a given input. For example, a biological system can have a biological input, a mechanical system can have a mechanical data input, an electrical system can have a relative electrical data input, a financial system can have a relative financial data input, a sociological system can have a relative sociological data input, a political system can have a relative political data input, and the like.

In some embodiments, the teachings are directed to a device for predicting a time-dependent response of a component of a mammalian system to an input into the system. In these embodiments, the device can comprise a processor; a database for storing a set of actual input data, a set of time-dependent actual response data, test input data, and time-dependent test response data on a non-transitory computer readable medium; an enumeration engine on a non-transitory computer readable medium to parameterize a non-compartmental model for predicting a test response to a test input, the non-compartmental model comprising the formula $$C(t) = [M_0^0 + M_0^1(\text{kernel})] + \qquad (9)$$
$$[M_1^0 + M_1^1(\text{kernel})]\left\{\frac{1 - e^{-[N_1^0 + N_1^1(\text{kernel})]t}}{1 + (e^K - 2)e^{-[N_1^0 + N_1^1(\text{kernel})]t}}\right\} + \ldots +$$
$$[M_n^0 + M_n^1(\text{kernel})]\left\{\frac{1 - e^{-[N_n^0 + N_n^1(\text{kernel})]t}}{1 + (e^K - 2)e^{-[N_n^0 + N_n^1(\text{kernel})]t}}\right\}$$

wherein,
$M_0^0, \ldots, M_n^0$ and $M_0^1, \ldots, M_n^1$ are overall scaling parameters;
$N_1^0, \ldots, N_n^0$ and $N_1^1, \ldots, N_n^1$ are exponential scaling parameters;
n ranges from 1 to 4;
K is an overall shifting parameter; and,
C(t) is the time-dependent response to the test input at time t;
and, $$\text{kernel} \equiv \frac{1 - e^{-\alpha_p C_0}}{1 + (e^{K_p} - 2)e^{-\alpha_p C_0}};$$

wherein, $C_0$ is the initial amount of the test input; $K_p$ is a shifting parameter related to $C_0$; and, $\alpha_p$ is shifting and scaling parameter related to $C_0$;
and, a transformation module on a non-transitory computer readable medium to transform the test data into the time-dependent response data using the non-compartmental model.

Any desired component known to one of skill can be used, in which the desired component is a component of interest to the person of skill. In some embodiments, the component can be blood, a tumor cell, a virus, a bacteria, or a combination thereof.

Any desired test response known to one of skill can be used, in which the desired test response is a response of interest to the person of skill. In some embodiments, the test response is a bacterial load, a viral load, a tumor marker, a blood chemistry, or a combination thereof.

Any desired set of actual inputs known to one of skill can be used, in which the desired set of actual inputs are of interest to the person of skill. In some embodiments, the set of actual inputs can include a set of dosages of a drug, a set of drugs, or a combination thereof.

Any desired input known to one of skill can be used, in which the desired input is of interest to the person of skill. In some embodiments, the input is a diabetes drug, and the time-dependent response can be glucose in the bloodstream.

The systems, methods, and devices taught herein transform input data into response data and, as such, can be used to obtain the time-dependent test response to the test input. And, the devices taught herein can be in any form, whether handheld, desktop, intranet, internet, or otherwise cloud-based. In some embodiments, the device can be a handheld device including, but not limited to, a PDA, a smartphone, an iPAD, a personal computer, and the like, including devices that are not intended for any other substantial use.

DETAILED DESCRIPTION

Non-mechanistic, differential-equation-free approaches for predicting a particular response of a system to a given input are provided in the form of systems, methods, and devices. These approaches are generally directed to a non-compartmental method of predicting a time-dependent response of a component of a system to an input into the system. The systems, methods, and devices provide the ability to (i) reduce the cost of research and development by offering an accurate modeling of heterogeneous and complex physical systems; (ii) reduce the cost of creating such systems and methods by simplifying the modeling process; (iii) accurately capture and model inherent nonlinearities in cases where sufficient knowledge does not exist to a priori build a model and its parameters; and, (iv) provide one-to-one relationships between model parameters and model outputs, addressing the problem of the ambiguities inherent in the current, state-of-the-art systems and methods.

Figure 1:
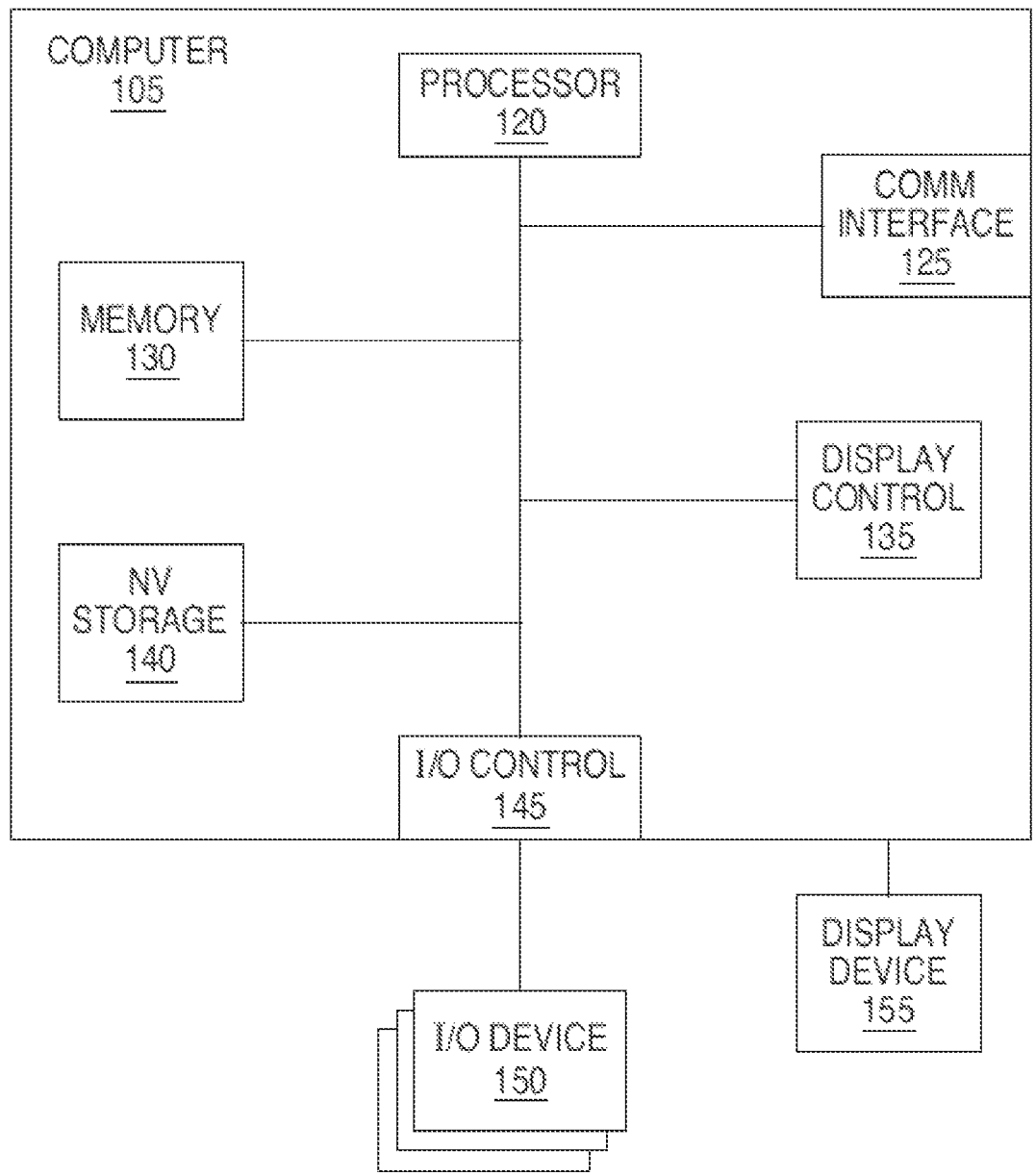
FIG. 1 shows a general technology platform for systems that can be used in the practice of the methods taught herein, according to some embodiments.

FIG. 1 shows a general technology platform for systems that can be used in the practice of the methods taught herein, according to some embodiments. The computer system 100 may be a conventional computer system and includes a computer 105, I/O devices 110, and a display device 115. The computer 105 can include a processor 120, a communications interface 125, memory 130, display controller 135, non-volatile storage 140, and I/O controller 145. The computer system 100 may be coupled to or include the I/O devices 150 and display device 155.

The computer 105 interfaces to external systems through the communications interface 125, which may include a modem or network interface. It will be appreciated that the communications interface 125 can be considered to be part of the computer system 100 or a part of the computer 105. The communications interface 125 can be an analog modem, isdn modem, cable modem, token ring interface, satellite transmission interface (e.g. "direct PC"), or other interfaces for coupling the computer system 100 to other computer systems. In a cellular telephone or PDA, for example, this interface can be a radio interface for communication with a cellular network and may also include some form of cabled interface for use with an immediately available personal computer. In a two-way pager, the communications interface 125 is typically a radio interface for communication with a data transmission network but may similarly include a cabled or cradled interface as well. In a personal digital assistant, for example, the communications interface 125 typically can include a cradled or cabled interface and may also include some form of radio interface, such as a BLUETOOTH or 802.11 interface, or a cellular radio interface.

The processor 120 may be, for example, a conventional microprocessor such as an Intel Pentium microprocessor or Motorola power PC microprocessor, a Texas Instruments digital signal processor, or a combination of such components. The memory 130 is coupled to the processor 120 by a bus. The memory 130 can be dynamic random access memory (DRAM) and can also include static ram (SRAM). The bus couples the processor 120 to the memory 130, also to the non-volatile storage 140, to the display controller 135, and to the I/O controller 145.

The I/O devices 150 can include a keyboard, disk drives, printers, a scanner, and other input and output devices, including a mouse or other pointing device. The display controller 136 may control in the conventional manner a display on the display device 155, which can be, for example, a cathode ray tube (CRT) or liquid crystal display (LCD). The display controller 135 and the I/O controller 145 can be implemented with conventional well known technology, meaning that they may be integrated together, for example.

The non-volatile storage 140 is often a FLASH memory or read-only memory, or some combination of the two. Any non-volatile storage can be used. A magnetic hard disk, an optical disk, or another form of storage for large amounts of data may also be used in some embodiments, although the form factors for such devices typically preclude installation as a permanent component in some devices. Rather, a mass storage device on another computer is typically used in conjunction with the more limited storage of some devices. Some of this data is often written, by a direct memory access process, into memory 130 during execution of software in the computer 105. One of skill in the art will immediately recognize that the terms "machine-readable medium," "computer-readable storage medium," or "computer-readable medium" includes any type of storage device that is accessible by the processor 120 and also encompasses a carrier wave that encodes a data signal. Objects, methods, inline caches, cache states and other object-oriented components may be stored in the non-volatile storage 140, or written into memory 130 during execution of, for example, an object-oriented software program. In some embodiments, these media can include modules or engines, for example, in which the modules or engines are complete, in that they can include the software, hardware, software/hardware combinations, and any other components recognized by one of skill that enable their operability in their functions as taught herein.

The computer system 100 is one example of many possible different architectures. For example, personal computers based on an Intel microprocessor often have multiple buses, one of which can be an I/O bus for the peripherals and one that directly connects the processor 120 and the memory 130 (often referred to as a memory bus). The buses are connected together through bridge components that perform any necessary translation due to differing bus protocols.

In addition, the computer system 100 is controlled by operating system software which includes a file management system, such as a disk operating system, which is part of the operating system software. One example of an operating system software with its associated file management system software is the family of operating systems known as Windows CE® and Windows® from Microsoft Corporation of Redmond, Wash., and their associated file management systems. Another example of operating system software with its associated file management system software is the LINUX operating system and its associated file management system. Another example of an operating system software with its associated file management system software is the PALM operating system and its associated file management system. The file management system is typically stored in the non-volatile storage 140 and causes the processor 120 to execute the various acts required by the operating system to input and output data and to store data in memory, including storing files on the non-volatile storage 140. Other operating systems may be provided by makers of devices, and those operating systems typically will have device-specific features which are not part of similar operating systems on similar devices. Similarly, WinCE® or PALM operating systems may be adapted to specific devices for specific device capabilities. Other examples include Google's ANDROID, Apple's IOS, Nokia's SYMBIAN, RIM's BLACKBERRY OS, Samsung's BADA, Microsoft's WINDOWS PHONE, Hewlett-Packard's WEBOS, and embedded Linux distributions such as MAEMO and MEEGO, and the like.

The computer system 100 may be integrated onto a single chip or set of chips in some embodiments, and typically is fitted into a small form factor for use as a personal device. Thus, it is not uncommon for a processor, bus, onboard memory, and display/I-O controllers to all be integrated onto a single chip. Alternatively, functions may be split into several chips with point-to-point interconnection, causing the bus to be logically apparent but not physically obvious from inspection of either the actual device or related schematics.

Figure 2:
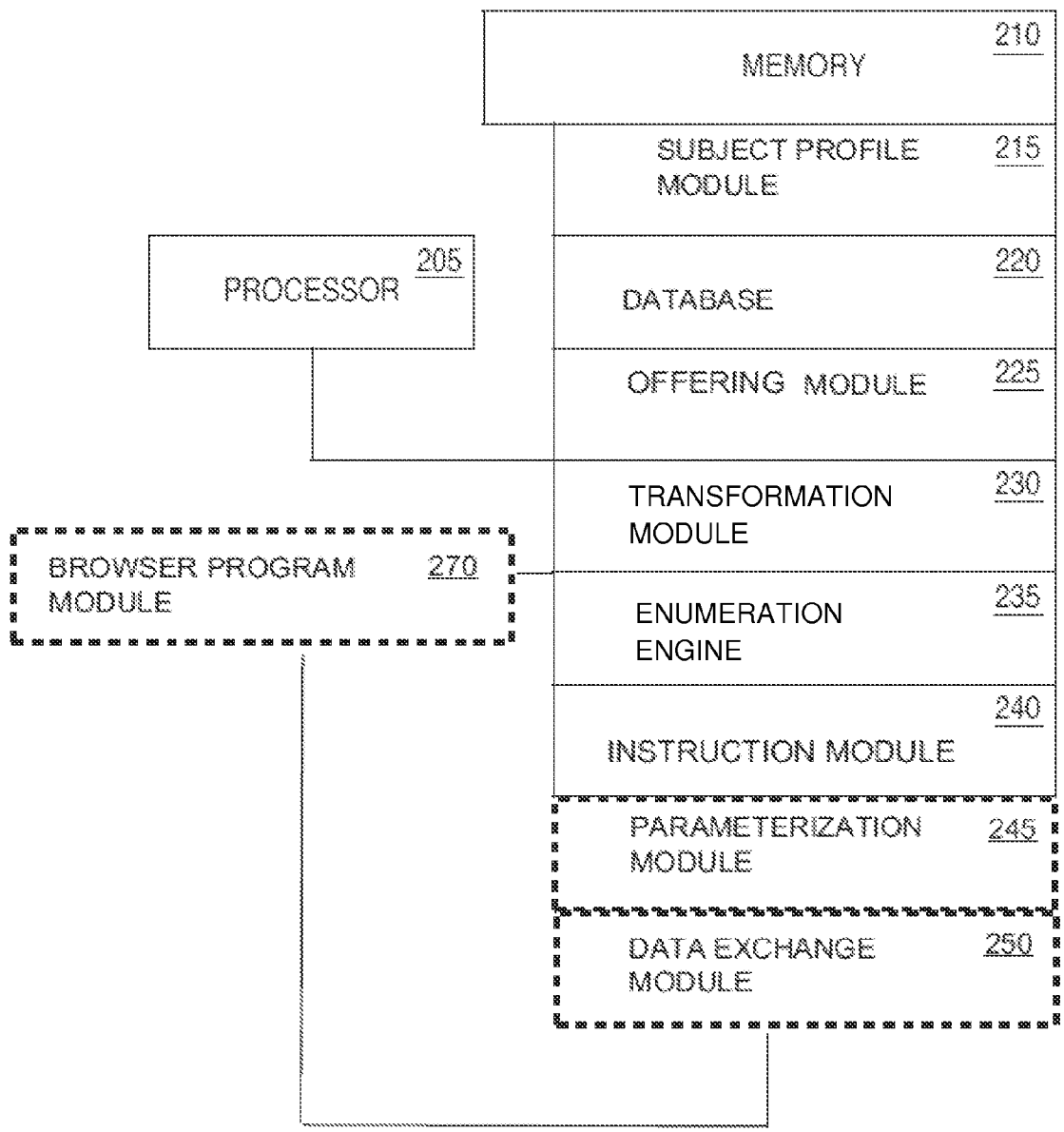
FIG. 2 illustrates a processor-memory diagram to describe components of a system, according to some embodiments.

FIG. 2 illustrates a processor-memory diagram to describe components of a system, according to some embodiments. The system 200 shown in FIG. 2 can include, for example, a processor 205 and a memory 210 (that can include non-volatile memory), wherein the memory 210 includes a subject-profile module 215, a database 220, an offering module 225, a solutions module 230, an integration engine 235, and an instruction module 240. And, as shown in the figure, other components can be included.

The system includes an input device (not shown) operable to allow a user to enter a personalized subject-profile into the computing system. Examples of input devices include a keyboard, a mouse, a data exchange module operable to interact with external data formats, voice-recognition software, a hand-held device in communication with the system, and the like.

The offering module 225 can be embodied in a non-transitory computer readable storage medium and operable for offering an opportunity for members of a network community to provide a submission of input data, response data, or the like, to the network community. The instruction module 240 can be embodied in a non-transitory computer readable storage medium and operable for providing instruction to a member of the network community regarding a criteria for making a submission of any type, or interacting within the community in any way.

The player/challenge database 220 can be embodied in a non-transitory computer readable storage medium and operable to store a library of users, user-submissions, input data, response data, and the like, wherein the database can include any text or any other media, including data compilations, statistics, and the like, or whatever other information may be considered useful to the network community.

The subject-profile module 215 can be embodied in a non-transitory computer readable storage medium and operable for receiving the personalized subject-profile and converting the personalized subject profile into a user profile. The user profile can comprise a set of personal statistics for the user, along with a tracking of the user's participation in the network community, as well as data regarding the same. As such, this provides a way for users of similar interests to identify one another and target community groups, subgroups, and even one-on-one communications. The input device can allow a user to enter a personalized subject-profile into a computing system. And, the personalized subject-profile can comprise a questionnaire designed to obtain information to be used to produce a personalized file for the user.

The transformation module 230 can be embodied in a non-transitory computer readable storage medium and operable for parsing input data, response data, other such data, and the like in the database into categories for use in user analyses. The enumeration engine 235 can be embodied in a non-transitory computer readable storage medium and operable to parameterize, for example, a non-compartmental model for predicting a test response to a test input.

It should be appreciated that any of the modules or engines can have additional functions, and additional modules or engines can be added to further provide even more functionality. Of course, the system will have a processor 205. And, the graphical user interface (not shown) can be used for displaying video, audio, and/or text to the user.

In some embodiments, the system further comprises a parameterization module operable 245 to derive select parameters such as, for example, display-preference parameters from the user profile, and the graphical user interface displays select data from the database 220 in accordance with the user's display preferences and in the form of the customized set of information subset options. Select parameters may include user selections, administrator selections, or some combination thereof. For example, the user may prefer a select combination of shapes, colors, sound, and any other of a variety of screen displays and multimedia options. Furthermore, the selections can be used to personalize and change the display-preference parameters easily and at any time.

In some embodiments, the system further comprises a data exchange module 250 operable to interact with external data formats obtained from another database or source, such as a remote memory source, including any external memory or file known to one of skill, including other user databases within the network community.

In some embodiments, the system further comprises a messaging module (not shown) operable to allow users to communicate with other users. The users can email one another, post blogs, or have instant messaging capability for real-time communications. In some embodiments, the users have video and audio capability in the communications, wherein the system implements data streaming methods known to those of skill in the art.

The systems taught herein can be practiced with a variety of system configurations, including personal computers, multiprocessor systems, microprocessor-based or programmable consumer electronics, network PCs, minicomputers, mainframe computers, and the like. The teachings can also be practiced in distributed computing environments where tasks are performed by remote processing devices that are linked through a communications network. As such, in some embodiments, the system further comprises an external computer connection and a browser program module 270. The browser program module 270 can be operable to access external data through the external computer connection.

Figure 3:
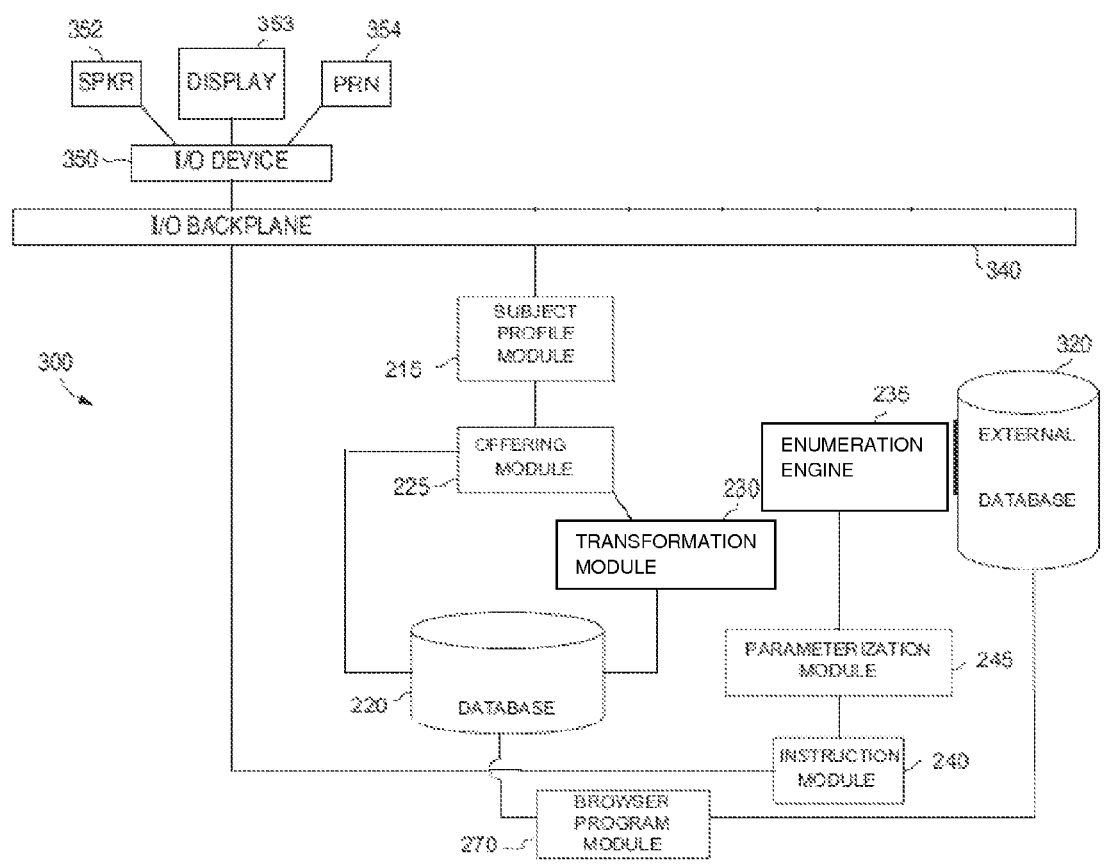
FIG. 3 is a concept diagram illustrating a system taught herein, according to some embodiments.

FIG. 3 is a concept diagram illustrating a system taught herein, according to some embodiments. The system 300 contains components that can be used in a typical embodiment. In addition to the subject-profile module 215, database 220, the offering module 225, the transformation module 230, the enumeration engine 235, and the instruction module 240 shown in FIG. 2, the memory 210 of the device 300 also includes parameterization module 245 and the browser program module 270 for accessing the external database 320. The system can include a speaker 352, display 353, and a printer 354 connected directly or through I/O device 350 connected to I/O backplane 340.

It should be appreciated that, in some embodiments, the system can be implemented in a stand-alone device, rather than a computer system or network, such that the device functions as a virtual system as provided herein, but does not perform any other substantially different functions. In FIG. 3, for example, the I/O device 350 connects to the speaker (spkr) 352, display 353, and microphone (mic) 354, but could also be coupled to other features. Other features can be added such as, for example, an on/off button, a start button, an ear phone input, and the like. In some embodiments, the system can turn on and off through motion. And, in some embodiments, the systems can include security measures to protect the user's privacy, integrity of data, or both.

State-of-the-Art Modeling is Complex, Insufficient, and Ambiguous

Input-response computer modeling is typically formulated mathematically by relating the rates of change of species within the system to amounts of species present in the system. Rates of change are expressed as first-order derivatives; therefore the resulting formulation is a system of first-order differential equations. Running a simulation, or running the model, is simply solving the system of differential equations. The output of the simulation are the concentration vs. time curves of each of the species in the system. The coefficients of the terms in the differential equations are often referred to as the parameters of the model. An example of such a system is given below:

$$\frac{\partial C_1}{\partial t} = k_{11}C_1 + k_{12}C_2 + \ldots + k_{1n}C_n$$

$$\frac{\partial C_2}{\partial t} = k_{21}C_1 + k_{22}C_2 + \ldots + k_{2n}C_n$$

$$\vdots$$

$$\frac{\partial C_n}{\partial t} = k_{n1}C_1 + k_{n2}C_2 + \ldots + k_{nn}C_n;$$

where, in this example, $C_1, C_2, \ldots, C_n$ represent the concentrations of the n different species in the system and $k_{11}, k_{12}, \ldots, k_{nn}$ are the parameters of the model. Changing the values of the parameters will change the output of the model. Proper adjustment of the parameters will yield the desired output; i.e., concentration curves that match a desired set of available data. This adjustment of parameters to produce desired output is referred to as parameter optimization or model calibration.

If all of the $k_{ij}$'s are real-valued constants, then the system is said to be a linear system of differential equations. Many physical systems are modeled using linear systems of differential equations, but there are often cases where a linear model is insufficient and a nonlinear model is required. In a nonlinear system of differential equations, at least one of the $k_{ij}$'s is a function of one of the $C_i$'s. For a linear system, the solution for the $C_i$'s as functions of time will be of the form $$C_i(t) = M_{i_1} e^{\beta_{i_1} t} + M_{i_2} C^{\beta_{i_1} t} + \ldots + M_{i_n} C^{\beta_{i_n} t}$$

where, the number of terms n is the same as the number of species being modeled. Each of the solution variables $M_{ij}$, and $\beta_{ij}$ is a function of the model parameters $k_{11}, \ldots, k_{nn}$. For a linear system, each of the solution functions, $C_i(t)$, will be a linear function of all the initial values, $C_i(0)$.

This approach of setting up a model (system of differential equations, etc.) with associated parameters that affect the output (solution functions) is called a mechanistic approach to modeling. In a mechanistic approach, the model species and parameters can be constructed to represent actual physiological components (physiologically-based modeling) or can simply serve as a sufficient number of mathematical degrees of freedom to allow for accurate model fits to given data.

In order to formulate a system of differential equations in the modeling process, a compartmental approach is often used. That is, a network of compartments is set up, with connections between each that specify the rate at which species are transferred between compartments. Compartmental models can be constructed using linear or nonlinear reactions between compartments. In linear models, parameter values are constants. FIG. 1 shows an example of a simple two-compartment linear model, with forward ($k_f$) and reverse ($k_r$) reactions between the two compartments as well as elimination ($k_e$) from the second compartment. In this linear model, $k_f$, $k_r$, and $k_e$ are all real-valued constants.

Figure 4:
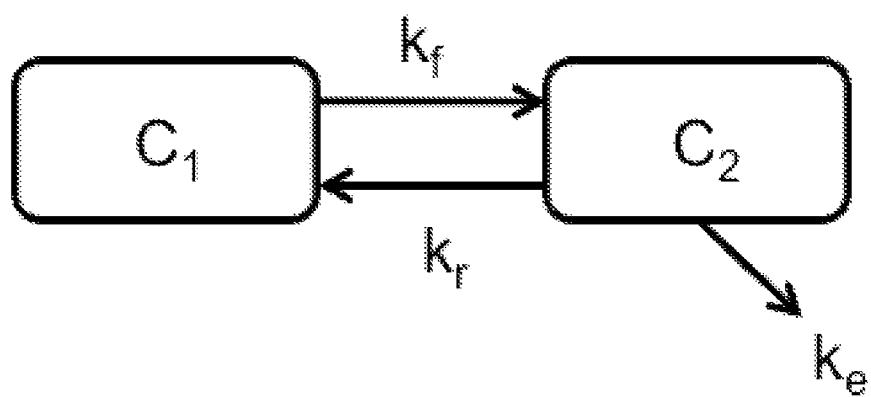
FIG. 4 shows an example of a prior art, simple two-compartment linear model, with forward ($k_f$) and reverse ($k_r$) reactions between the two compartments as well as elimination ($k_e$) from the second compartment, according to some embodiments.

FIG. 4 shows an example of a prior art, simple two-compartment linear model, with forward ($k_f$) and reverse ($k_r$) reactions between the two compartments as well as elimination ($k_e$) from the second compartment, according to some embodiments.

The resulting differential equations are:

$$V_1 \frac{\partial C_1}{\partial t} = -k_f C_1 + k_r C_2$$

$$V_2 \frac{\partial C_2}{\partial t} = k_f C_1 - (k_r + k_e) C_2;$$

where, $V_1$ and $V_2$ represent the physical volumes of compartments 1 and 2, respectively. These volumes are often not known and have to be either physically or mathematically estimated. The compartmental modeling approach can be, but is not always, physiologically-based. In a physiologically-based model, each compartment represents an actual physiological entity, and the reactions between compartments are based on expert knowledge of the interactions between the included physiological entities.

FIG. 4 is an example of a mechanistic approach to input-response modeling, and the vast majority of input-response modeling is done using a mechanistic approach. In this approach, the components of the model - - - nodes, connections, differential equations, parameters, etc. - - - are set up based on knowledge of the underlying physical mechanisms present in the system. Parameter values are initially set based on expert knowledge of how certain components of the system should behave with respect to other related components. This provides a very useful tool in exploratory research, where one can examine the effects that result from turning certain 'knobs' or 'handles' (parameters) in the model. There are two serious limitations of this mechanistic approach. The first is one of sufficiency and the other is one of ambiguity.

Mechanistic models often lack sufficient content to provide accurate predictions of input-response relationships, and this is because current expert knowledge is often lacking in its ability to fully characterize a system or all of the interactions within a system. This lack of knowledge might manifest itself in not having enough compartments in a compartmental model, or in having linear transfer rates between compartments when in fact the underlying process is nonlinear. What is often done in these cases is to go back to the model and arbitrarily add compartments or make certain reactions nonlinear, in an attempt provide the necessary mathematical foundation to allow for sufficiently accurate fits to given data. In this way, many models become non-physiologically-based when the intent was to build a physiologically-based model.

Another significant limitation to the mechanistic approach comes from the fact that in mechanistic models, the model parameters are serving as an intermediary between the model inputs and outputs. The parameters are useful in serving as handles to affect output, but there is often not a unique mapping between model inputs and output. That is, there may be more than one way (or even an infinite number of ways) to achieve a certain output from a given set of inputs. This ambiguity can be very problematic when attempting to do things like map the properties of the input to the output. For example, in a dose-response model, it would be extremely valuable to be able to map molecular properties of a drug compound to a particular response within the body. Using a mechanistic dose-response model, this mapping would have to go from input to model parameters to output. If there are many different sets of model parameters that can produce the same output, then it becomes very difficult, or impossible, to use the parameters as an intermediary in constructing an effective mapping from input properties (molecular properties of dose compound) to output (response within the body).

The Systems and Methods Set-Forth Herein are Simple, Sufficient, and Unambiguous To address the limitations of the current, state-of-the-art, the teachings set-forth herein include a novel system of modeling that uses a data-based, non-mechanistic, differential-equation-free approach for predicting a particular response of a system to a given input. There is no system of differential equations, yet the form of the response function is similar to a solution function obtained from a system of differential equations. Because there is no system of differential equations, there are no associated "model parameters." The only unknowns that need to be optimized are the variables in the response function. This eliminates the potential ambiguity that is present in using differential equation parameters as the intermediary between input and output, as is the case in a mechanistic approach. The response function for this new approach is an extension of the solution function for a system of linear differential equations, Equation 1, where the exponential terms are replaced by terms containing rational functions of exponentials. The basic form is given by:

$$C(t) = M_0 + M_1 \left[ \frac{1 - e^{-\alpha_1 t}}{1 + (e^K - 2)e^{-\alpha_1 t}} \right] + \ldots + M_n \left[ \frac{1 - e^{-\alpha_n t}}{1 + (e^K - 2)e^{-\alpha_n t}} \right]. \quad (2)$$

If $K=\ln(2)$, then the response function (2) reduces to a form that is equivalent to the linear solution function (1).

One of the characteristics of a solution function for a nonlinear system is that the variables $M_0, M_1, \ldots, M_n$ and $\alpha_1, \ldots, \alpha_n$ are all functions of the initial input condition, or dose. That is, if we define dose as $C_0$, then $M_0, M_1, \ldots, M_n$ and $\alpha_1, \ldots, \alpha_n$ are all functions of $C_0$. In this new formulation, the functions $M_0(C_0), M_1(C_0), \ldots, M_n(C_0)$ and $\alpha_1(C_0)$ and $\alpha_1(C_0), \ldots, \alpha_n(C_0)$ are also defined using the formulation of Equation (2). These functions are given by:

$$M_0(C_0) = M_0^0 + M_0^1 \left[ \frac{1 - e^{(-\alpha_{M_0}^1)C_0}}{1 + (e^{K_{M_0}} - 2)e^{(-\alpha_{M_0}^1)C_0}} \right] +$$

$$\ldots + M_0^q \left[ \frac{1 - e^{(-\alpha_{M_0}^q)C_0}}{1 + (e^{K_{M_0}} - 2)e^{(-\alpha_{M_0}^q)C_0}} \right]$$

$$\vdots$$

$$M_n(C_0) = M_n^0 + M_n^1 \left[ \frac{1 - e^{(-\alpha_{M_n}^1)C_0}}{1 + (e^{K_{M_n}} - 2)e^{(-\alpha_{M_n}^1)C_0}} \right] +$$

$$\ldots + M_n^q \left[ \frac{1 - e^{(-\alpha_{M_n}^q)C_0}}{1 + (e^{K_{M_n}} - 2)e^{(-\alpha_{M_n}^q)C_0}} \right]$$

$$\alpha_1(C_0) = N_1^0 + N_1^1 \left[ \frac{1 - e^{(-\alpha_{\alpha_1}^1)C_0}}{1 + (e^{K_{\alpha_1}} - 2)e^{(-\alpha_{\alpha_1}^1)C_0}} \right] +$$

$$\ldots + N_1^q \left[ \frac{1 - e^{(-\alpha_{\alpha_1}^q)C_0}}{1 + (e^{K_{\alpha_1}} - 2)e^{(-\alpha_{\alpha_1}^q)C_0}} \right]$$

$$\vdots$$

$$\alpha_n(C_0) =$$

$$N_n^0 + N_n^1 \left[ \frac{1 - e^{(-\alpha_{\alpha_n}^1)C_0}}{1 + (e^{K_{\alpha_n}} - 2)e^{(-\alpha_{\alpha_n}^1)C_0}} \right] + \ldots + N_n^q \left[ \frac{1 - e^{(-\alpha_{\alpha_n}^q)C_0}}{1 + (e^{K_{\alpha_n}} - 2)e^{(-\alpha_{\alpha_n}^q)C_0}} \right].$$

The full implementation of this formulation would require the estimation of a large number of parameters. In many embodiments, however, a reduced form will be sufficient for providing accurate models of input-response relationships. In some embodiments, a less reduced form, or even the full implementation, may be used.

The reduced form makes two assumptions. The first is that the number of terms in the $M_0(C_0), M_1(C_0), \ldots, M_n(C_0)$ and $\alpha_1(C_0), \ldots, \alpha_n(C_0)$ functions is truncated at 1; i.e., q=1. The second is that only one α parameter and only one K parameter is used for all of the $M_0(C_0), M_1(C_0), \ldots, M_n(C_0)$ and $\alpha_1(C_0), \ldots, \alpha_n(C_0)$ functions; i.e., $$\alpha_{M_0}^1 = \alpha_{M_1}^1 = \ldots = \alpha_{M_n}^1 = \alpha_{\alpha_1}^1 = \ldots = \alpha_{\alpha_n}^1 \equiv \alpha_p \quad (3)$$

$$K_{M_0}^1 = K_{M_1}^1 = \ldots = K_{M_n}^1 = K_{\alpha_1}^1 = \ldots = K_{\alpha_n}^1 \equiv K_p \quad (4)$$

Substituting the relationships (3) and (4) into the functions $M_0(C_0), M_1, \ldots, (C_0), \ldots, M_n(C_0)$ and $\alpha_1(C_0), \ldots, \alpha_n(C_0)$, and truncating those functions at q=1 yields:

$$M_0(C_0) = M_0^0 + M_0^1 \left[ \frac{1 - e^{-\alpha_p C_0}}{1 + (e^{K_p} - 2)e^{-\alpha_p C_0}} \right] \quad (5)$$

$$\vdots$$

$$M_n(C_0) = M_n^0 + M_n^1 \left[ \frac{1 - e^{-\alpha_p C_0}}{1 + (e^{K_p} - 2)e^{-\alpha_p C_0}} \right] \quad (6)$$

$$\alpha_1(C_0) = N_1^0 + N_1^1 \left[ \frac{1 - e^{-\alpha_p C_0}}{1 + (e^{K_p} - 2)e^{-\alpha_p C_0}} \right] \quad (7)$$

$$\vdots$$

$$\alpha_n(C_0) = N_n^0 + N_n^1 \left[ \frac{1 - e^{-\alpha_p C_0}}{1 + (e^{K_p} - 2)e^{-\alpha_p C_0}} \right] \quad (8)$$

To simplify, define a kernel function, which is a function of initial input condition, or dose, $C_0$ $$\text{kernel} \equiv \frac{1 - e^{-\alpha_p C_0}}{1 + (e^{K_p} - 2)e^{-\alpha_p C_0}}$$

Substituting Equations (5)-(8) into Equation (2) yields:

$$C(t) = [M_0^0 + M_0^1(\text{kernel})] + \qquad (9)$$
$$[M_1^0 + M_1^1(\text{kernel})] \left\{ \frac{1 - e^{-[N_1^0 + N_1^1(\text{kernel})]t}}{1 + (e^K - 2)e^{-[N_1^0 + N_1^1(\text{kernel})]t}} \right\} + \ldots +$$
$$[M_n^0 + M_n^1(\text{kernel})] \left\{ \frac{1 - e^{-[N_n^0 + N_n^1(\text{kernel})]t}}{1 + (e^K - 2)e^{-[N_n^0 + N_n^1(\text{kernel})]t}} \right\}$$

This new form for the response function allows for nonlinear model behavior as well as time-lagged effects. Theoretically, this allows for accurate characterization and model description of complex physical phenomena. The new response function contains n terms, where n is an arbitrary number and can be set to achieve desired accuracy.

The modeling approach using this new formulation is to estimate the values of $K$, $K_p$, $\alpha_p$, $M_0^0$, ..., $M_n^0$, $M_0^1$, ..., $M_n^1$, $N_1^0$, ..., $N_n^0$, and $N_1^1$, ..., $N_n^1$ that yield the best fit of response function to available data. In this approach, there will be much less (ideally not any) ambiguity between values of response function variables and goodness of fit between model and data. In other words, if you define error as the difference between available data and model prediction, then error as a function of response function variables will be more convex and contain fewer local minima than the error as a function of model parameters in the case of a mechanistic modeling approach.

A great deal of system information is condensed into the response function variables of the new formulation. Complex phenomena such as nonlinear behavior can be described using much fewer degrees of freedom than is the case in a mechanistic approach where a large number of model parameters is typically used. This will reduce the redundancy that often occurs in mechanistic models using a large number of model parameters. The response variables in the new formulation can even take into account information that is not known prior to building a model, but shows up in the form of response data. Thus, the new formulation avoids the insufficiency that is often seen in mechanistic models.

Essentially, the variables in the response function (Equation (9)) will all be unique functions of the model parameters, but the reverse is not true. That is, the model parameters are not necessarily unique functions of response variables (as will be demonstrated in detail in Example 1). Therefore, the response variables in the systems and methods taught herein represent some (unknown) function of model parameters, if there were model parameters. But because the systems and methods taught herein allow for nonlinear behavior, for which there are not analytical solutions, the response variables represent complicated functions of many different potential model parameters, and therefore provide sufficiency in the case where sufficient knowledge does not exist to a priori build the model and its parameters. This new formulation also removes the ambiguity that exists in mechanistic modeling approaches, where model parameters are not unique functions of response variables.

The optimization of the response variables in the systems and methods taught herein is even more complicated than the optimization of the variables in the linear response function given by Equation (1), and requires a series of unconstrained and constrained linear and nonlinear optimization procedures (which are described in more detail in Example 9). It should be noted that if a linear response function is sufficient, then the optimization of the response variables in the systems and methods taught herein can be used, in some embodiments, to yield a response function that is equivalent to the linear response function given by Equation (1). Therefore, the systems and methods taught herein will accurately describe both linear and nonlinear phenomena. Once optimal values of response variables are obtained for a given system, the model can be used to yield an accurate prediction of the system's response to the introduction of an input of interest. The goal of this method is to provide accurate input-response predictions over a wide range of scale. For example, this algorithm could be used to make accurate predictions of responses on the tissue/organ-scale in the human body based solely on the molecular properties of input compounds. This could have significant impact in areas such as absorption-distribution-metabolism-excretion (ADME) prediction in drug design, as well as drug development in personalized medicine.

Figure 5:
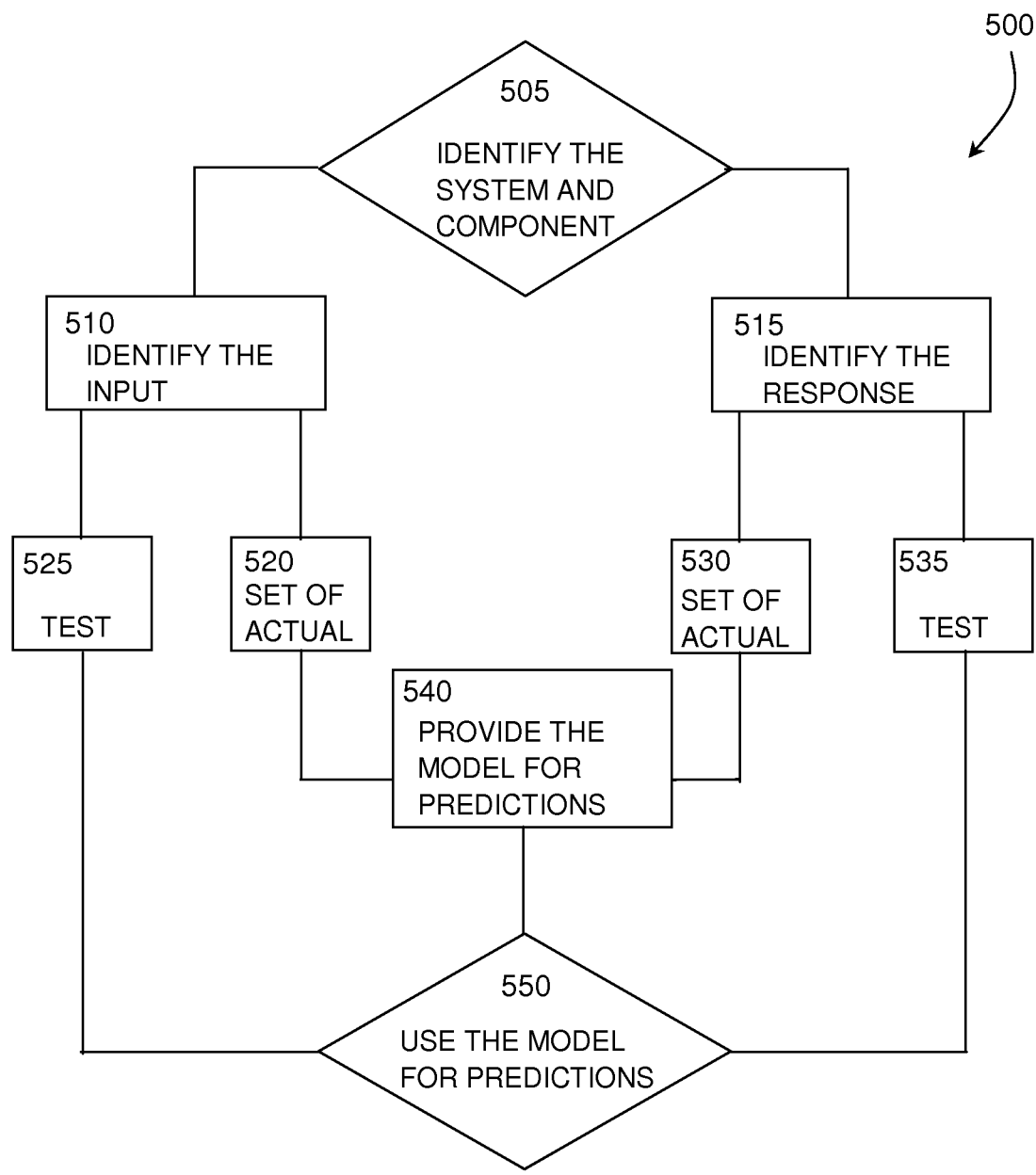
FIG. 5 illustrates a flowchart for a non-compartmental method of predicting a time-dependent response of a component of a system to an input into the system, according to some embodiments.

FIG. 5 illustrates a flowchart for a non-compartmental method of predicting a time-dependent response of a component of a system to an input into the system, according to some embodiments. The method can comprise identifying 505 the system and the component, identifying 510 the input, and identifying 515 the time-dependent response; wherein, the input includes a set of actual 520 inputs and a test 525 input, and the time-dependent response includes a set of time-dependent actual 530 responses and a test 535 response; obtaining the set of time-dependent actual responses of the component to the set of actual inputs; and, using the set of actual inputs and the set of time-dependent actual responses to provide 540 a model for predicting the test response to the test input, the model comprising the formula:

$$C(t) = [M_0^0 + M_0^1(\text{kernel})] + \qquad (9)$$
$$[M_1^0 + M_1^1(\text{kernel})] \left\{ \frac{1 - e^{-[N_1^0 + N_1^1(\text{kernel})]t}}{1 + (e^K - 2)e^{-[N_1^0 + N_1^1(\text{kernel})]t}} \right\} + \ldots +$$
$$[M_n^0 + M_n^1(\text{kernel})] \left\{ \frac{1 - e^{-[N_n^0 + N_n^1(\text{kernel})]t}}{1 + (e^K - 2)e^{-[N_n^0 + N_n^1(\text{kernel})]t}} \right\}$$

wherein,
$M^0{}_0$, ..., $M^0{}_n$ and $M^1{}_0$, ..., $M^1{}_n$ are overall scaling parameters;
$N^0{}_1$, ..., $N^0{}_n$ and $N^1{}_1$, ..., $N^1{}_n$ are exponential scaling parameters;
n ranges from 1 to 4;
K is an overall shifting parameter; and,
C(t) is the time-dependent response to the test input at time t;
and, $$\text{kernel} \equiv \frac{1 - e^{-\alpha_p C_0}}{1 + (e^{K_p} - 2)e^{-\alpha_p C_0}};$$

wherein, $C_0$ is the initial amount of the test input; $K_p$ is a shifting parameter related to $C_0$; and, $\alpha_p$ is shifting and scaling parameter related to $C_0$.

The last step in FIG. 5 is using 550 the model for predictions.

Non-compartmental methods of predicting a time-dependent response of a component of a mammalian system to an input into the system are also provided. In these embodiments, the methods can comprise selecting a component of the system, the component selected from the group consisting of a cell, a tissue, an organ, a DNA, a virus, a protein, an antibody, a bacteria; selecting a set of actual inputs, the set of actual inputs having an element selected from the group consisting of a DNA, a virus, a protein, an antibody, a bacteria, a chemical, a dietary supplement, a nutrient, and a drug; obtaining a set of time-dependent actual responses of the component to the set of actual inputs; and, using the set of actual inputs and the set of time-dependent actual responses to provide a model for predicting a test response to a test input, the model comprising the formula $$C(t) = [M_0^0 + M_0^1(\text{kernel})] + \quad (9)$$

$$[M_1^0 + M_1^1(\text{kernel})]\left\{\frac{1 - e^{-[N_1^0 + N_1^1(\text{kernel})]t}}{1 + (e^K - 2)e^{-[N_1^0 + N_1^1(\text{kernel})]t}}\right\} + \ldots +$$

$$[M_n^0 + M_n^1(\text{kernel})]\left\{\frac{1 - e^{-[N_n^0 + N_n^1(\text{kernel})]t}}{1 + (e^K - 2)e^{-[N_n^0 + N_n^1(\text{kernel})]t}}\right\}$$

wherein,
$M^0_0, \ldots, M^0_n$ and $M^1_0, \ldots, M^1_n$ are overall scaling parameters;
$N^0_1, \ldots, N^0_n$ and $N^1_1, \ldots, N^1_n$ are exponential scaling parameters;
n ranges from 1 to 4;
K is an overall shifting parameter; and,
C(t) is the time-dependent response to the test input at time t;
and, $$\text{kernel} \equiv \frac{1 - e^{-\alpha_p C_0}}{1 + (e^{K_p} - 2)e^{-\alpha_p C_0}};$$

wherein, $C_0$ is the initial amount of the test input; $K_p$ is a shifting parameter related to $C_0$; and, $\alpha_p$ is shifting and scaling parameter related to $C_0$.

Devices for predicting a time-dependent response of a component of a physical system to an input into the system are provided. In these embodiments, the device can comprise a processor; a database for storing a set of actual input data, a set of time-dependent actual response data, test input data, and time-dependent test response data on a non-transitory computer readable medium; an enumeration engine on a non-transitory computer readable medium to parameterize a non-compartmental model for predicting a test response to a test input, the non-compartmental model comprising the formula $$C(t) = [M_0^0 + M_0^1(\text{kernel})] + \quad (9)$$

$$[M_1^0 + M_1^1(\text{kernel})]\left\{\frac{1 - e^{-[N_1^0 + N_1^1(\text{kernel})]t}}{1 + (e^K - 2)e^{-[N_1^0 + N_1^1(\text{kernel})]t}}\right\} + \ldots +$$

$$[M_n^0 + M_n^1(\text{kernel})]\left\{\frac{1 - e^{-[N_n^0 + N_n^1(\text{kernel})]t}}{1 + (e^K - 2)e^{-[N_n^0 + N_n^1(\text{kernel})]t}}\right\}$$

wherein,
$M^0_0, \ldots, M^0_n$ and $M^1_0, \ldots, M^1_n$ are overall scaling parameters;
$N^0_1, \ldots, N^0_n$ and $N^1_1, \ldots, N^1_n$ are exponential scaling parameters;
n ranges from 1 to 4;
K is an overall shifting parameter; and,
C(t) is the time-dependent response to the test input at time t;
and, $$\text{kernel} \equiv \frac{1 - e^{-\alpha_p C_0}}{1 + (e^{K_p} - 2)e^{-\alpha_p C_0}};$$

wherein, $C_0$ is the initial amount of the test input; $K_p$ is a shifting parameter related to $C_0$; and, $\alpha_p$ is shifting and scaling parameter related to $C_0$;

and, a transformation module on a non-transitory computer readable medium to transform the test data into the time-dependent response data using the non-compartmental model.

The systems can be virtually any physical or non-physical system known to one of skill in which that person of skill may want to predict a particular response of the system to a given input. In some embodiments, the system can be an environmental system, and the component can be selected from the group consisting of air, water, and soil. In some embodiments, the system can be a mammal, and the component can be selected from the group consisting of a cell, a tissue, an organ, a DNA, a virus, a protein, an antibody, a bacteria. In some embodiments, the system can be a chemical system, a biological system, a mechanical system, an electrical system, a financial system, a sociological system, a political system, or a combination thereof. As such, the teachings provided herein include general methods of predicting a particular response of any such system to a given input. For example, a biological system can have a biological input, a mechanical system can have a mechanical data input, an electrical system can have a relative electrical data input, a financial system can have a relative financial data input, a sociological system can have a relative sociological data input, a political system can have a relative political data input, and the like.

In some embodiments, the input into the system can cause a substantial effect or a negligible effect. The term "negligible effect" can be used, for example, to mean that the activity does not increase or decrease more than about 10% when compared to any one or any combination of the compounds of interest, respectively, without the other components. In some embodiments, the term "negligible effect" can be used to refer to a change of less that 10%, less than 9%, less than 8%, less than 7%, less than 6%, less than 5%, less than 4%, and less than 3%. In some embodiments, the term "negligible effect" can be used to refer to a change ranging from about 3% to about 10%, in increments of 1%.

The effects of the input can be biological, such as in drug testing or the testing of compositions used in treating a subject. The compositions tested, for example, can be referred to as extracts, compositions, compounds, agents, active agents, bioactive agents, supplements, drugs, and the like. In some embodiments, the terms "composition," "compound," "agent," "active", "active agent", "bioactive agent," "supplement," and "drug" can be used interchangeably and, it should be appreciated that, a "formulation" can comprise any one or any combination of these. Likewise, in some embodiments, the composition can also be in a liquid or dry form, where a dry form can be a powder form in some embodiments, and a liquid form can include an aqueous or non-aqueous component. Moreover, the term "bioactivity" can refer to the function of the compound when administered in any way known to one of skill, including parenterally or non-parenterally, including orally, topically, or rectally to a subject. In some embodiments, the term "target site" can be used to refer to a select location on or in a subject that could benefit from an administration of a compound. In some embodiments, a target can include any site of action in which the agent's activity, such as any therapeutic activity including anti-hyperproliferative activity, antioxidant activity, anti-inflammatory activity, analgesic activity, and the like, can serve a benefit to the subject. The target site can be a healthy or damaged tissue of a subject. As such, the teachings include a method of administering one or more compounds taught herein to any healthy or damaged tissue, such as epithelial, connective, muscle, or nervous tissue, including hematopoietic, dermal, mucosal, gastrointestinal or otherwise.

The systems and methods herein can determine the stability of a composition in a system. In some embodiments, a composition or formulation can be considered as "stable" if it loses less than 10% of its original activity. In some embodiments, a composition or formulation can be considered as stable if it loses less than 5%, 3%, 2%, or 1% of its original activity. In some embodiments, a composition or formulation can be considered as "substantially stable" if it loses greater than about 10% of its original activity, as long as the composition can perform it's intended use to a reasonable degree of efficacy. In some embodiments, the composition can be considered as substantially stable if it loses activity at an amount greater than about 12%, about 15%, about 25%, about 35%, about 45%, about 50%, about 60%, or even about 70%. The activity loss can be measured by comparing activity at the time of packaging to the activity at the time of administration, and this can include a reasonable shelf life. In some embodiments, the composition is stable or substantially stable, if it remains useful for a period ranging from 3 months to 3 years, 6 months to 2 years, 1 year, or any time period therein in increments of about 1 month.

Moreover, the systems and methods provided herein can be used in predicting the efficacy of therapeutic treatments. The terms "treat," "treating," and "treatment" can be used interchangeably in some embodiments and refer to the administering or application of the compositions and formulations taught herein, including such administration as a health or nutritional supplement, and all administrations directed to the prevention, inhibition, amelioration of the symptoms, or even a cure of a condition in a subject. The terms "disease," "condition," "disorder," and "ailment" can be used interchangeably in some embodiments. The term "subject" and "patient" can be used interchangeably in some embodiments and refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, and the like.

In some embodiments, the methods further comprise orally administering an effective amount of an oral dosage form of a composition to a subject to systemically treat a disease or disorder, including any disease or disorder taught herein. In some embodiments, the methods further comprise orally administering an effective amount of an oral dosage form of a composition to a subject as a dietary supplement. In some embodiments, the methods further comprise orally administering an effective amount of an oral dosage form of a composition to a subject in combination with a second drug. In some embodiments, the teachings are directed to a method of treating an inflammation of a tissue of subject, the method comprising administering an effective amount of a composition to a tissue of the subject. In some embodiments, the teachings are directed to treating a wounded tissue, the method comprising administering an effective amount of a composition to a tissue of the subject. In some embodiments, the teachings are directed to treating a hyperproliferative disorder, such as cancer, either liquid or solid, the method comprising administering an effective amount of a composition to a subject in need thereof.

An "effective amount" of a compound can be used to describe a therapeutically effective amount or a prophylactically effective amount. An effective amount can also be an amount that ameliorates the symptoms of a disease. A "therapeutically effective amount" can refer to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount should be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition.

In cases of the prevention or inhibition of the onset of a disease or disorder, or where an administration is considered prophylactic, a prophylactically effective amount of a composition or formulation taught herein can be used. A "prophylactically effective amount" can refer to an amount that is effective at the dosages and periods of time necessary to achieve a desired prophylactic result, such as prevent the onset of a sunburn, an inflammation, allergy, nausea, diarrhea, infection, and the like. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, a therapeutically or prophylactically effective amount of a composition may range in concentration from about 0.01 nM to about 0.10 M; from about 0.01 nM to about 0.5 M; from about 0.1 nM to about 150 nM; from about 0.1 nM to about 500 µM; from about 0.1 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein. In some embodiments, the compositions may be administered in an amount ranging from about 0.005 mg/kg to about 100 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is often assumed to average about 70 kg. Moreover, the systems and methods taught herein can use micro-dosing, which can include the administration of dosages that are one, two, or perhaps three orders of magnitude less than the dosages described above, in some embodiments.

Any drug activity can be investigated using the systems and methods taught herein. In some embodiments, the activity can include, for example, free radical scavenger and antioxidant, inhibiting lipid peroxidation and oxidative DNA damage; anti-inflammatory activity; neurological treatments for Alzheimer's disease (anti-amyloid and other effects), Parkinson's disease, and other neurological disorders; anti-arthritic treatment; anti-ischemic treatment; treatments for multiple myeloma and myelodysplastic syndromes; psoriasis treatments (topically and orally); cystic fibrosis treatments; treatments for liver injury and alcohol-induced liver disease; multiple sclerosis treatments; antiviral treatments, including human immunodeficiency virus (HIV) therapy; treatments of diabetes; cancer treatments; and, reducing risk of heart disease; to name a few.

Any response can be investigated using the systems and methods taught herein. For example, the amounts of the agents can be reduced, even substantially, such that the amount of the agent or agents desired is reduced to the extent that a significant response is observed from the subject. A "significant response" can include, but is not limited to, a reduction or elimination of a symptom, a visible increase in a desirable therapeutic effect, a faster response to the treatment, a more selective response to the treatment, or a combination thereof. In some embodiments, the other therapeutic agent can be administered, for example, in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein. Combination therapies can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered desirable by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents. One of skill can readily select the frequency, duration, and perhaps cycling of each concurrent administration.

As such, in some embodiments, the teachings are directed to a device for predicting a time-dependent response of a component of a mammalian system to an input into the system. In these embodiments, the device can comprise a processor; a database for storing a set of actual input data, a set of time-dependent actual response data, test input data, and time-dependent test response data on a non-transitory computer readable medium; an enumeration engine on a non-transitory computer readable medium to parameterize a non-compartmental model for predicting a test response to a test input, the non-compartmental model comprising the formula $$C(t) = [M_0^0 + M_0^1(\text{kernel})] + \qquad (9)$$

$$[M_1^0 + M_1^1(\text{kernel})]\left\{\frac{1-e^{-[N_1^0+N_1^1(\text{kernel})]t}}{1+(e^K-2)e^{-[N_1^0+N_1^1(\text{kernel})]t}}\right\} + \ldots +$$

$$[M_n^0 + M_n^1(\text{kernel})]\left\{\frac{1-e^{-[N_n^0+N_n^1(\text{kernel})]t}}{1+(e^K-2)e^{-[N_n^0+N_n^1(\text{kernel})]t}}\right\}$$

wherein,
$M^0{}_0, \ldots, M^0{}_n$ and $M^1{}_0, \ldots, M^1{}_n$ are overall scaling parameters;
$N^0{}_1, \ldots, N^0{}_n$ and $N^1{}_1, \ldots, N^1{}_n$ are exponential scaling parameters;
n ranges from 1 to 4;
K is an overall shifting parameter; and,
C(t) is the time-dependent response to the test input at time t;
and, $$\text{kernel} \equiv \frac{1-e^{-\alpha_p C_0}}{1+(e^{K_p}-2)e^{-\alpha_p C_0}};$$

wherein, $C_0$ is the initial amount of the test input; $K_p$ is a shifting parameter related to $C_0$; and, $\alpha_p$ is shifting and scaling parameter related to $C_0$;
and, a transformation module on a non-transitory computer readable medium to transform the test data into the time-dependent response data using the non-compartmental model.

Any desired component known to one of skill can be used, in which the desired component is a component of interest to the person of skill. In some embodiments, the component can be blood, a tumor cell, a virus, a bacteria, or a combination thereof.

Any desired test response known to one of skill can be used, in which the desired test response is a response of interest to the person of skill. In some embodiments, the test response is a bacterial load, a viral load, a tumor marker, a blood chemistry, or a combination thereof.

Any desired set of actual inputs known to one of skill can be used, in which the desired set of actual inputs are of interest to the person of skill. In some embodiments, the set of actual inputs can include a set of dosages of a drug, a set of drugs, or a combination thereof.

Any desired input known to one of skill can be used, in which the desired input is of interest to the person of skill.

For example, the systems, methods, and devices can be used in drug screening. In some embodiments, the input is a diabetes drug candidate, and the time-dependent response can be glucose in the bloodstream. In some embodiments, the input is a cancer drug candidate, and the time-dependent response can be a cell apoptosis, tumor size reduction, reduced metastasis. In some embodiments, the input is an antibiotic drug candidate, and the time-dependent response can be a bacterial load. In some embodiments, the input is an antiviral drug candidate, and the time-dependent response can be a viral load. In some embodiments, the input is an immunomodulatory drug candidate, and the time-dependent response can be a measure of an immune response. In some embodiments, the input is an anti-inflammatory drug candidate, and the time-dependent response can be an inflammatory response. In some embodiments, the input is an analgesic drug candidate, and the time-dependent response can be a pain response.

The systems, methods, and devices taught herein transform input data into response data and, as such, can be used to obtain the time-dependent test response to the test input. And, the devices taught herein can be in any form, whether handheld, desktop, intranet, internet, or otherwise cloud-based. In some embodiments, the device can be a handheld device including, but not limited to, a PDA, a smartphone, an iPAD, a personal computer, and the like, including devices that are not intended for any other substantial use.

Figure 6:
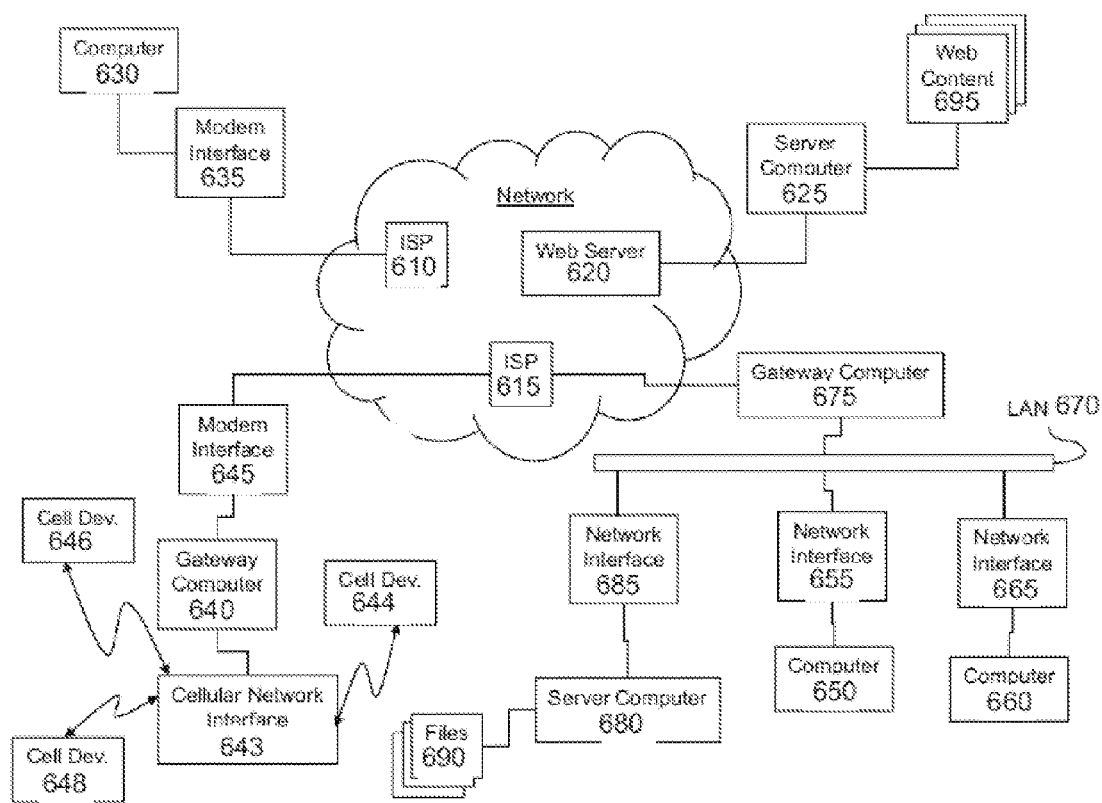
FIG. 6 shows how a network may be used for the systems and methods taught herein, in some embodiments.

FIG. 6 shows how a network may be used for the systems and methods taught herein, in some embodiments. FIG. 6 shows several computer systems coupled together through a network 605, such as the internet, along with a cellular network and related cellular devices. The term "internet" as used herein refers to a network of networks which uses certain protocols, such as the TCP/IP protocol, and possibly other protocols such as the hypertext transfer protocol (HTTP) for hypertext markup language (HTML) documents that make up the world wide web (web). The physical connections of the internet and the protocols and communication procedures of the internet are well known to those of skill in the art.

Access to the internet 605 is typically provided by internet service providers (ISP), such as the ISPs 610 and 615. Users on client systems, such as client computer systems 630, 650, and 660 obtain access to the internet through the internet service providers, such as ISPs 610 and 615. Access to the internet allows users of the client computer systems to exchange information, receive and send e-mails, and view documents, such as documents which have been prepared in the HTML format, for example. These documents are often provided by web servers, such as web server 620 which is considered to be "on" the internet. Often these web servers are provided by the ISPs, such as ISP 610, although a computer system can be set up and connected to the internet without that system also being an ISP.

In some embodiments, the system is a web enabled application and can use, for example, Hypertext Transfer Protocol (HTTP) and Hypertext Transfer Protocol over Secure Socket Layer (HTTPS). These protocols provide a rich experience for the end user by utilizing web 2.0 technologies, such as AJAX, Macromedia Flash, etc. In some embodiments, the system is compatible with Internet Browsers, such as Internet Explorer, Mozilla Firefox, Opera, Safari, etc. In some embodiments, the system is compatible with mobile devices having full HTTP/HTTPS support, such as IPHONE, ANDROID, SAMSUNG, POCKETPCs, MICROSOFT SURFACE, video gaming consoles, and the like. Others may include, for example, IPAD and ITOUCH devices. In some embodiments, the system can be accessed using a Wireless Application Protocol (WAP). This protocol will serve the non HTTP enabled mobile devices, such as Cell Phones, BLACKBERRY devices, etc., and provides a simple interface. Due to protocol limitations, the Flash animations are disabled and replaced with Text/Graphic menus. In some embodiments, the system can be accessed using a Simple Object Access Protocol (SOAP) and Extensible Markup Language (XML). By exposing the data via SOAP and XML, the system provides flexibility for third party and customized applications to query and interact with the system's core databases. For example, custom applications could be developed to run natively on APPLE devices, Java or .Net-enabled platforms, etc. One of skill will appreciate that the system is not limited to any of the platforms discussed above and will be amenable to new platforms as they develop.

The web server 620 is typically at least one computer system which operates as a server computer system and is configured to operate with the protocols of the world wide web and is coupled to the internet. Optionally, the web server 620 can be part of an ISP which provides access to the internet for client systems. The web server 620 is shown coupled to the server computer system 625 which itself is coupled to web content 695, which can be considered a form of a media database. While two computer systems 620 and 625 are shown in FIG. 6, the web server system 620 and the server computer system 625 can be one computer system having different software components providing the web server functionality and the server functionality provided by the server computer system 625 which will be described further below.

Cellular network interface 643 provides an interface between a cellular network and corresponding cellular devices 644, 646 and 648 on one side, and network 605 on the other side. Thus cellular devices 644, 646 and 648, which may be personal devices including cellular telephones, two-way pagers, personal digital assistants or other similar devices, may connect with network 605 and exchange information such as email, content, or HTTP-formatted data, for example. Cellular network interface 643 is coupled to computer 640, which communicates with network 605 through modem interface 645. Computer 640 may be a personal computer, server computer or the like, and serves as a gateway. Thus, computer 640 may be similar to client computers 650 and 660 or to gateway computer 675, for example. Software or content may then be uploaded or downloaded through the connection provided by interface 643, computer 640 and modem 645.

Client computer systems 630, 650, and 660 can each, with the appropriate web browsing software, view HTML pages provided by the web server 620. The ISP 610 provides internet connectivity to the client computer system 630 through the modem interface 635 which can be considered part of the client computer system 630. The client computer system can be, for example, a personal computer system, a network computer, a web TV system, or other such computer system.

Similarly, the ISP 615 provides internet connectivity for client systems 650 and 660, although as shown in FIG. 6, the connections are not the same as for more directly connected computer systems. Client computer systems 650 and 660 are part of a LAN coupled through a gateway computer 675. While FIG. 6 shows the interfaces 635 and 645 as generically as a "modem," each of these interfaces can be an analog modem, isdn modem, cable modem, satellite transmission interface (e.g. "direct PC"), or other interfaces for coupling a computer system to other computer systems.

Client computer systems 650 and 660 are coupled to a LAN 670 through network interfaces 655 and 665, which can be ethernet network or other network interfaces. The LAN 670 is also coupled to a gateway computer system 675 which can provide firewall and other internet related services for the local area network. This gateway computer system 675 is coupled to the ISP 615 to provide internet connectivity to the client computer systems 650 and 660. The gateway computer system 675 can be a conventional server computer system. Also, the web server system 620 can be a conventional server computer system.

Alternatively, a server computer system 680 can be directly coupled to the LAN 670 through a network interface 685 to provide files 690 and other services to the clients 650, 660, without the need to connect to the internet through the gateway system 675.

Through the use of such a network, for example, the system can also provide an element of social networking, whereby users can contact other users having similar subject-profiles, or user can contact anyone in the public to forward the personalized information. In some embodiments, the system can include a messaging module operable to deliver notifications via email, SMS, TWITTER, FACEBOOK, LINKEDIN, and other mediums. In some embodiments, the system is accessible through a portable, single unit device and, in some embodiments, the input device, the graphical user interface, or both, is provided through a portable, single unit device. In some embodiments, the portable, single unit device is a hand-held device.

Regardless of the information presented, the system includes a broader concept of a platform for the research community, whether corporate, academic, private, or not-for-profit, for example, to communicate in an engaging way, whether confidential or public. For example, the systems and methods taught herein can enable researchers to use a computer/mobile network mobile interface to propose problems and solutions, offer data, request data, and otherwise communicate regarding issues of common interest. The systems and methods presented herein can be considered a "game-changer" in art of research and development using computer modeling.

It should be also appreciated that the methods and displays presented herein, in some embodiments, are not inherently related to any particular computer or other apparatus, unless otherwise noted. Various general purpose systems may be used with programs in accordance with the teachings herein, or it may prove convenient to construct a specialized apparatus to perform the methods of some embodiments. The required structure for a variety of these systems will be apparent to one of skill given the teachings herein. In addition, the techniques are not described with reference to any particular programming language, and various embodiments may thus be implemented using a variety of programming languages. Accordingly, the terms and examples provided above are illustrative only and not intended to be limiting; and, the term "embodiment," as used herein, means an embodiment that serves to illustrate by way of example and not limitation. The following examples are illustrative of the uses of the present invention. It should be appreciated that the examples are for purposes of illustration and are not to be construed as limiting to the invention.

Example 1

Pharmacokinetics Modeling

The systems and methods taught herein can be used in pharmacokinetic (PK) models. In this example, a compartmental approach was used in a PK model to show the advantages of using the non-mechanistic formulations and modeling approaches taught herein.

PK models are often used to describe the fate of substances administered externally to a living organism. In drug development, they are typically used to model the concentration of a drug in the bloodstream after oral, intravenous, or subcutaneous introduction into the body. PK analysis is performed by non-compartmental or compartmental methods. Non-compartmental methods estimate the exposure to a drug by estimating parameters such as area under the concentration-time curve (AUC), mean residence time, clearance, elimination half-life, elimination rate constant, peak plasma concentration ($C_{max}$), time to reach $C_{max}$, and minimum inhibitory concentration (MIC). Compartmental methods estimate the concentration-time graph using kinetic models. The advantage of compartmental over some non-compartmental analyses is the ability to predict the concentration at any time. The disadvantage is the difficulty in developing and validating the proper model.

1.1 Compartmental Pharmacokinetics

Figure 7:
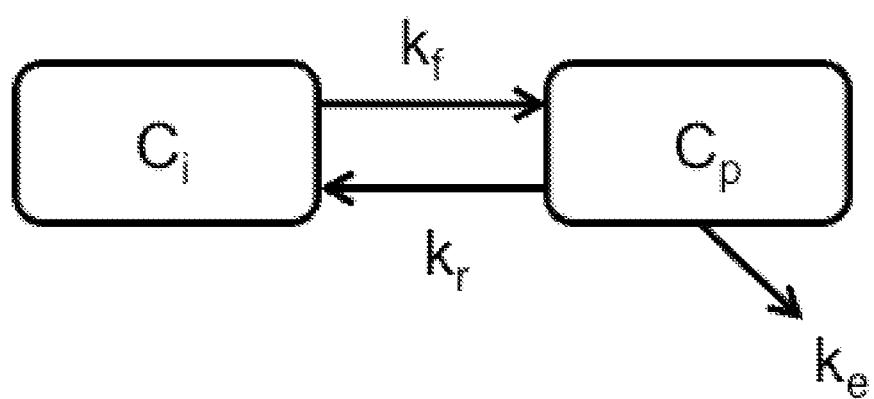
FIG. 7 shows a prior art, two-compartment linear model that was constructed to model the PK behavior of a particular drug, according to some embodiments.

FIG. 7 shows a prior art, two-compartment linear model that was constructed to model the PK behavior of a particular drug, according to some embodiments. In this example, the first compartment represents the gastro-intestinal (GI) region and the second represents plasma.

The resulting differential equations are:

$$V_i \frac{\partial C_i}{\partial t} = -k_f C_i + k_r C_p$$

$$V_p \frac{\partial C_p}{\partial t} = k_f C_i - (k_r + k_e) C_p;$$

where, $C_i$ and $C_p$ are the concentrations of the drug in the GI and plasma compartments, respectively; $V_i$ and $V_p$ are the volumes of distribution for the GI and plasma compartments, respectively; and $k_f$, $k_r$, and $k_e$ are the reaction rate constants. The initial conditions for this model are $C_i(0)=$ initial dose$=C_0$, $C_p(0)=0$.

The species of interest in this example is the plasma concentration, $C_p$. The solution to this system of differential equations for $C_p$ is:

$$C_p(t) = MC_0(e^{\beta_1 t} - e^{\beta_2 t});$$
$$\beta_1 > \beta_2;$$
where, $$\beta_1 = \frac{-\frac{k_f}{V_i} - \frac{k_r + k_e}{V_p} + \sqrt{\left(\frac{k_f}{V_i} + \frac{k_r + k_e}{V_p}\right)^2 - \frac{4 k_f k_e}{V_i V_p}}}{2} \quad (10)$$

$$\beta_2 = \frac{-\frac{k_f}{V_i} - \frac{k_r + k_e}{V_p} - \sqrt{\left(\frac{k_f}{V_i} + \frac{k_r + k_e}{V_p}\right)^2 - \frac{4 k_f k_e}{V_i V_p}}}{2} \quad (11)$$

$$M = \frac{k_f}{V_p \sqrt{\left(\frac{k_f}{V_i} + \frac{k_r + k_e}{V_p}\right)^2 - \frac{4 k_f k_e}{V_i V_p}}} \quad (12)$$

Note that, regardless of the parameter values, the solution for $C_p(t)$ is linear with respect to the initial dose; i.e., solutions for different initial doses are simply scalar multiplies of one another.

Figure 8:
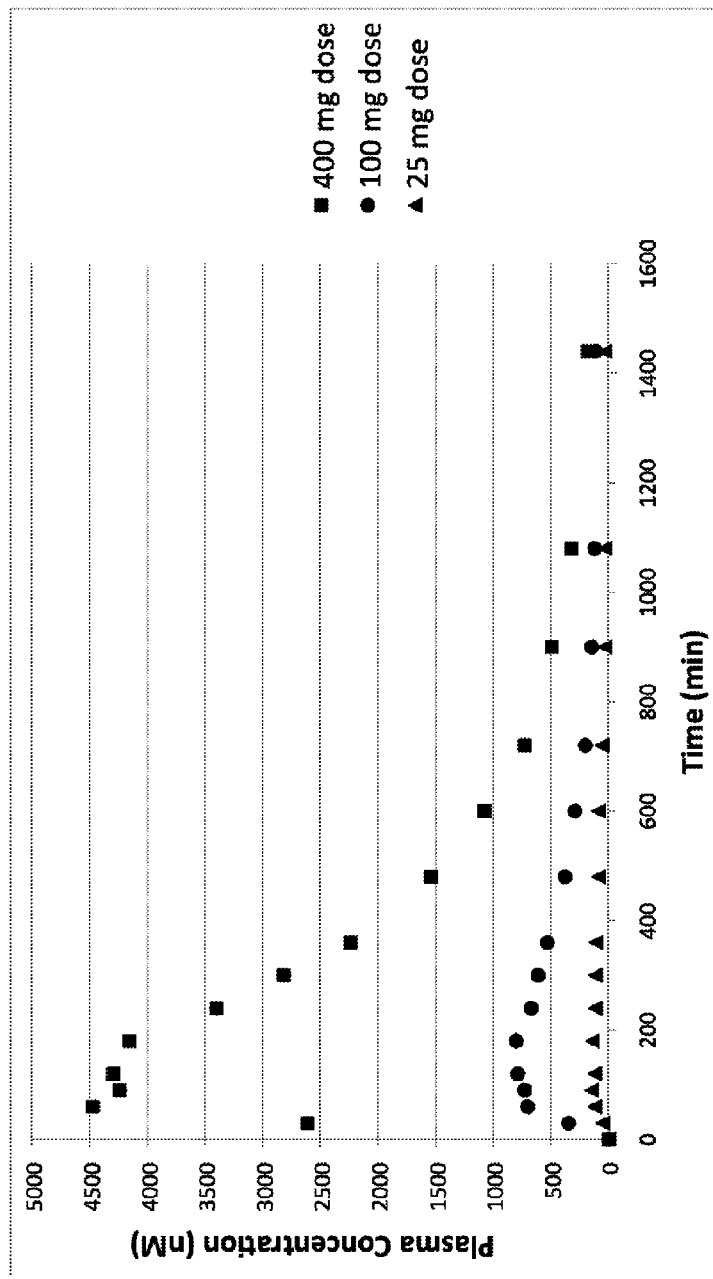
FIG. 8 shows the data used to calibrate this model (find optimal parameter values) a two-compartment linear model that was constructed to model the PK behavior of a particular drug, according to some embodiments.

FIG. 8 shows the data used to calibrate this model (find optimal parameter values), a two-compartment linear model that was constructed to model the PK behavior of a particular drug, according to some embodiments. Doses of 25 mg, 100 mg, and 400 mg were administered orally. See, for example, Bergman, A., et al. Biopharm. Drug Dispos., 28: 307-313 (2007), which is hereby incorporated herein by reference in its entirety.

When the solution variables $\beta_1$, $\beta_2$ and M are optimized to yield the best fit for all of the data, the resulting optimal values are:
$\beta_1 = -0.0025$
$\beta_2 = -0.0165$
$M = 13$
which gives the solution for any initial dose as $$C_p(t) = 13 C_0 (e^{-0.0025\, t} \ldots e^{-0.0165\, t})$$

In this case, the optimized solution variables give the best fit for the middle dose data, while overestimating the lower-dose data and underestimating the higher-dose data.

Figure 9:
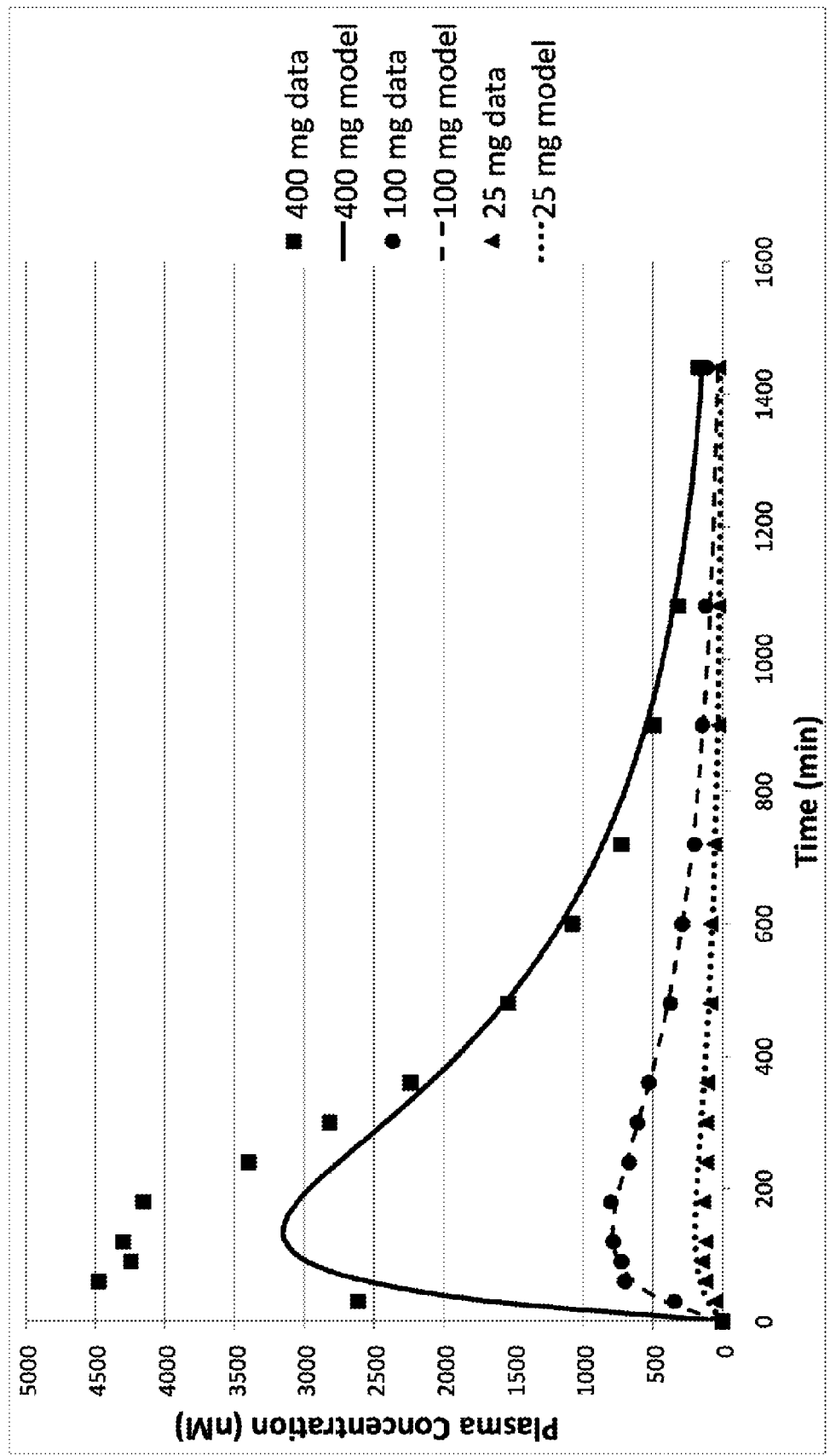
FIG. 9 shows a linear two-compartment model solute on for $C_p(t)$ compared to data for the pharmacokinetic modeling, according to some embodiments.

FIG. 9 shows a linear two-compartment model solute on for $C_p(t)$ compared to data for the pharmacokinetic modeling, according to some embodiments. In particular, the model solution for $C_p(t)$ is compared to the data for each of the 25 mg, 100 mg, and 400 mg cases. It shows that the model provides a good fit to the 100 mg data, but there is an overestimation of the 25 mg data and a significant underestimation of the 400 mg data.

One limitation of the mechanistic modeling approach—the inability of the linear two-compartment model to accurately model the fate of the drug over the entire range of dose values; i.e., an insufficiency. The mechanistic approach lacks the necessary structure to adequately model the PK of this drug over the entire range of dose values. In this case, an insufficiency is that one of reaction rates is non-linear rather than linear. Adding compartments in this case will not improve the results.

Another limitation of the mechanistic modeling approach—ambiguity of model parameters, as shown by the following analysis: Equations (10)-(12) give expressions for solution variables ($\beta_1$, $\beta_2$, and M) in terms of model parameters ($k_f$, $k_r$, $k_e$, $V_i$, and $V_p$). In order to find the values of model parameters that correspond to a given set of optimal values for solution variables, we must find expressions for model parameters in terms of solution variables. These expressions are found by enforcing the constraints that all model parameters be greater than zero.

$$-\beta_1 \leq \frac{k_f}{V_i} \leq -\beta_2 \tag{13}$$

$$V_p = \frac{k_f}{M(\beta_1 - \beta_2)} \tag{14}$$

$$k_e = \frac{\beta_1 \beta_2 V_i V_p}{k_f} \tag{15}$$

$$k_r = (-\beta_1 - \beta_2) V_p - \frac{k_f V_p}{V_i} - k_e \tag{16}$$

By choosing any combination of $k_f$ and $V_i$ that satisfies condition (13), one can then solve for the remaining parameters $V_p$, $k_e$, and $k_r$ using the given solution variable values ($\beta_1$, $\beta_2$, and M) and Equations (14)-(16). Therefore, in this particular example with $\beta_1 = -0.0025$, $\beta_2 = -0.0165$, and $M = 13$, the optimal values for $k_f$, $V_i$, $V_p$, $k_e$, and $k_r$ are any that satisfy the following conditions:

$$0.0025 \leq \frac{k_f}{V_i} \leq 0.0165 \tag{17}$$

$$V_p = 5.49 * k_f \tag{18}$$

$$k_e = \frac{V_i V_p}{24242 * k_f} \tag{19}$$

$$k_r = 0.019 * V_p - \frac{k_f V_p}{V_i} - k_e \tag{20}$$

By choosing any combination of $k_f$ and $V_i$ that satisfies condition (17), one can then solve for the remaining parameters $V_p$, $k_e$, and $k_r$ using Equations (18)-(20). Thus, while there is only one set of solution variable values that result from a given set of model parameter values (Equations (10)-(12)), there are an infinite number of model parameter values that can result from a given set of solution variable values (Equations (13)-(16)). This non-unique solution to parameter-mapping illustrates the ambiguity that is present in a mechanistic approach to modeling, where model parameters are used as intermediaries between inputs and model outputs (solution functions). This ambiguity makes it difficult-to-impossible to map input properties to output solutions by way of model parameters.

1.2 Non-Compartmental Pharmacokinetics

The systems and methods taught herein are non-compartmental in design. Non-compartmental PK analysis fits concentration-time curves to available data, and then uses these curves to estimate parameters such as AUC, half-life, $C_{max}$, and time to reach $C_{max}$. The PK parameters can then be used, for example, to describe the behavior of a drug after it is introduced into the body.

The systems and methods taught herein are different than traditional non-compartmental PK approaches for at least the reason that traditional approaches use a mathematical formulation similar to Equation (1), which describes a linear system. The systems and methods taught herein, for example, are also able to automatically describe non-linearities in the system and give more accurate fits to the data. Moreover, there is the problem of non-unique mappings, which is also an issue with current non-compartmental PK analyses. Different concentration-time curves can have the same AUC but different $C_{max}$, or the same $C_{max}$, but different AUC, for example. And, different concentration-time curves can have the same AUC but different shapes, resulting in the time above minimum concentration being different (different clearance rates). One of skill will appreciate that such ambiguities make it difficult to map properties of an input compound to its PK parameters, significantly impacting the value of PK properties in making predictions of the behavior of potential drug compounds in a system.

The Systems and Methods Taught Herein Yield Predictions that are More Accurate than Current State-of-the-Art Methods Using the systems and methods taught herein, we can construct a model that yields accurate predictions of the fate of the drug over the entire range of dose values. The systems and methods taught herein provide equation (9), as taught herein for example, which is a three-term model that worked well for this particular PK example. Optimization of the response variables for the $C_p(t)$ function gives the following optimized values of the variables in the response function of equation (9) for the PK example:

TABLE 1

| K | $K_p$ | $\alpha_p$ | term i | $M_i^0$ | $M_i^1$ | $N_i^0$ | $N_i^1$ |
|---|---|---|---|---|---|---|---|
| 2.283 | 0.150 | 0.0010 | 0 | −0.028 | 0.081 | — | — |
| | | | 1 | −3.430 | −10.433 | 0.0040 | 0.0037 |
| | | | 2 | 4.432 | 10.121 | 0.0667 | 0.0274 |

It should be appreciated that the systems and methods taught herein provided a simplified modeling approach, as regardless of how many compartments or nonlinear reactions might have been attempted to achieve sufficient accuracy from a mechanistic approach to this problem, the systems and methods provided herein were sufficient with only the 13 values shown in Table 1.

Figure 10:
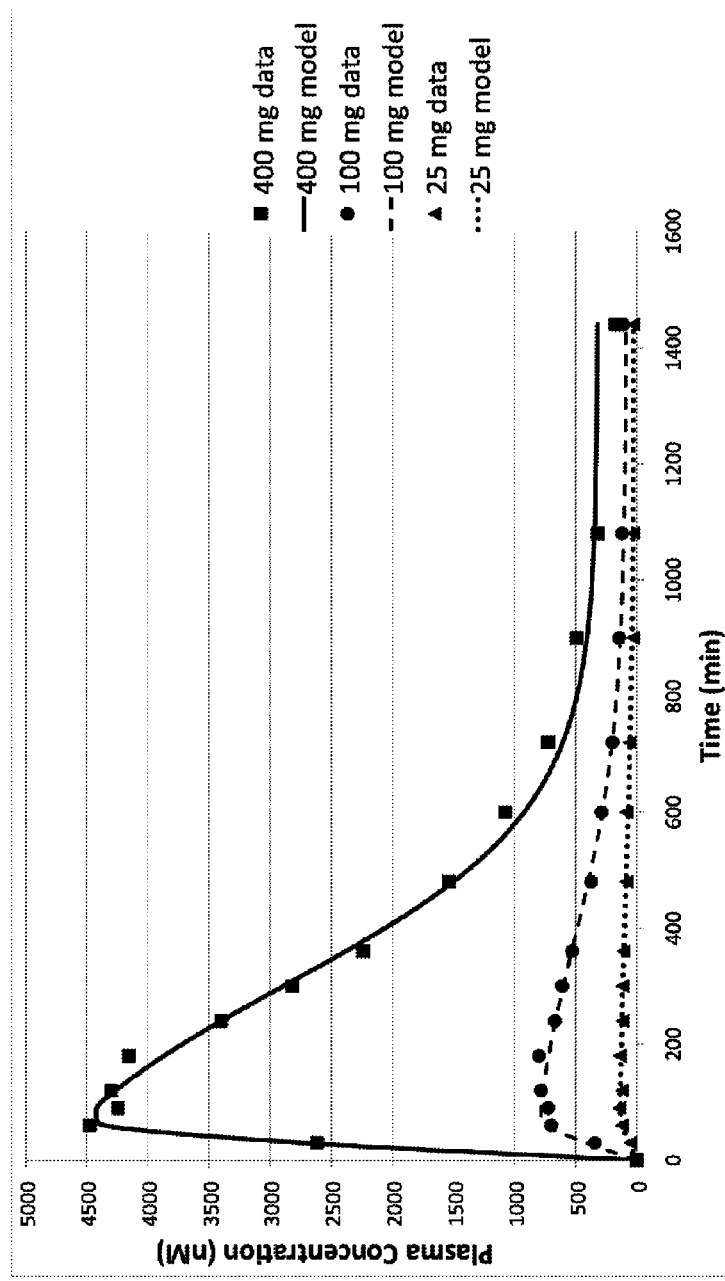
FIG. 10 shows the $C_p(t)$ response function compared to the data for each of the mg, 100 mg, and 400 mg cases, according to some embodiments.

FIG. 10 shows the $C_p(t)$ response function compared to the data for each of the mg, 100 mg, and 400 mg cases, according to some embodiments. As seen in FIG. 10, the systems and methods taught herein use the $C_p(t)$ response function to fit the data very well, illustrating that the systems and methods taught herein can accurately capture the inherent nonlinearity and, therefore, accurately model the fate of the drug over the entire range of dose values.

The additional degrees of freedom in the systems and methods taught herein provided a model that was more accurate than the compartmental model. In this example, the mechanistic compartment model contains only five model parameters and therefore involves fewer degrees of freedom than the systems and methods taught herein. In contrast, the two compartments, linear reactions, and five parameters in the compartmental model were not sufficient, as they did not adequately model the fate of the drug over the entire range of dose values. One of skill will appreciate that such current, state-of-the-art models can easily become large and involve hundreds of parameters. The systems and methods taught herein, however, provided sufficient accuracy using much fewer degrees of freedom, reducing the ambiguity that is otherwise present in the mechanistic approach with its large number of parameters.

Example 2

Enzyme Reaction Modeling (Non-Linear Kinetics)

This example models enzymatic reactions, which are inherently nonlinear in nature. Many input-response models are constructed using an assumption of linear reaction kinetics, which is often insufficient, particularly for large-scale and complex phenomena. One of skill will appreciate that, as shown in the previous PK example, a linear model may not accurately describe the fate of a drug over a wide range of input doses.

Enzyme kinetics is the study of the chemical reactions that are catalyzed by enzymes. The effects of reaction conditions on reaction rate are investigated which can reveal the catalytic mechanism of the enzyme, its role in metabolism, how its activity is controlled, and how a drug or an agonist might inhibit the activity. Typically, an enzymatic reaction involves an enzyme E binding to a substrate S to form a complex ES, which in turn is converted to a product P and the enzyme. This is represented schematically as:

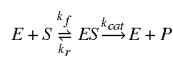

where $k_f$, $k_r$, and $k_{cat}$ denote the rate constants.

Applying the law of mass action, which states that the rate of a reaction is proportional to the product of the concentrations of the reactants, gives a system of four non-linear differential equations that define the rate of change of reactants with time t:

$$\frac{\partial [S]}{\partial t} = -k_f[E][S] + k_r[ES] \quad (21)$$

$$\frac{\partial [E]}{\partial t} = -k_f[E][S] + k_r[ES] + k_{cat}[ES] \quad (22)$$

$$\frac{\partial [ES]}{\partial t} = k_f[E][S] - k_r[ES] - k_{cat}[ES] \quad (23)$$

$$\frac{\partial [P]}{\partial t} = k_{cat}[ES]. \quad (24)$$

In this mechanism, the enzyme E is a catalyst, which only facilitates the reaction, so its total concentration, free plus combined, $[E]+[ES]=[E]_0$, is a constant. This conservation law can also be obtained by adding Equations (22) and (23). This system is nonlinear because of the products [E][S] that appear.

If you make the assumption that the concentration of the intermediate complex does not change on the time-scale of product formation, then $$\frac{\partial [ES]}{\partial t} = 0 \Rightarrow k_f[E][S] = k_r[ES] + k_{cat}[ES].$$

Combining this with the enzyme concentration law gives:

$$[ES] = \frac{[E]_0[S]}{\frac{k_r + k_{cat}}{k_f} + [S]}$$

From Equation (24), $$\frac{\partial [P]}{\partial t} = k_{cat}[ES] = \frac{k_{cat}[E]_0[S]}{\frac{k_r + k_{cat}}{k_f} + [S]}$$

If we define the following constants, $$V_{max} = k_{cat}[E]_0 \quad \text{the maximum reaction velocity}$$

$$K_m = \frac{k_r + k_{cat}}{k_f} \quad \text{the Michaelis constant;}$$

then, we arrive at the Michaelis-Menten model of enzyme kinetics $$\frac{\partial [P]}{\partial t} = \frac{V_{max}[S]}{K_m + [S]}, \quad (25)$$

which relates the rate of product formation to the concentration of substrate.

State-of-the-Art Michaelis-Menten Models Create Error Due to Invalid Assumptions Michaelis-Menten-type rates are not only used to model enzyme kinetics but are also used to model other saturable, nonlinear phenomena. Michaelis-Menten-type rates are often used in mechanistic compartment modeling to describe the nonlinear rate at which one species in a system is produced as a function of the concentration of some other species in the system. For this reason, it provides a very useful and practical example for comparing the systems and methods taught herein to typical mechanistic approaches to modeling nonlinear phenomena. The problem with using Michaelis-Menten-type rates for applications other than those for which it was derived is that the assumptions used to derive the approximation might not be applicable. For example, two assumptions used in deriving the Michaelis-Menten approximation are 1) $k_{cat} \ll k_r$, and 2) $E_0$ (the initial enzyme concentration)$\ll S_0$ (the initial substrate concentration). But these assumptions might not always be valid when attempting to use a Michaelis-Menten-type rate between two compartments in a systems biology model, which is often done.

To illustrate the error involved in using Michaelis-Menten-type rates when the underlying assumptions might not be valid, consider a system where $k_f = k_r = k_{cat} = 0.2$ and $E_0 = 10.0$. A Michaelis-Menten approximation (Equation (25)) of this system would have $V_{max} = 2.0$ and $K_m = 2.0$. It was found that using the systems and methods taught herein, using Equation (9) in some embodiments, a two-term model was sufficient for this particular enzymatic reaction example. Optimization of the solution variables for the P(t) function gives optimized values of the variables in Equation 9 as shown in Table 2 for the enzyme reaction modeling:

TABLE 2

| K | $K_p$ | $\alpha_p$ | term i | $M_i^0$ | $M_i^1$ | $N_i^0$ | $N_i^1$ |
|---|---|---|---|---|---|---|---|
| 1.065 | 2.798 | 0.1986 | 0 | −0.002 | −0.038 | — | — |
|  |  |  | 1 | 0.992 | 0.057 | 0.2352 | −0.0866 |

Figure 11:
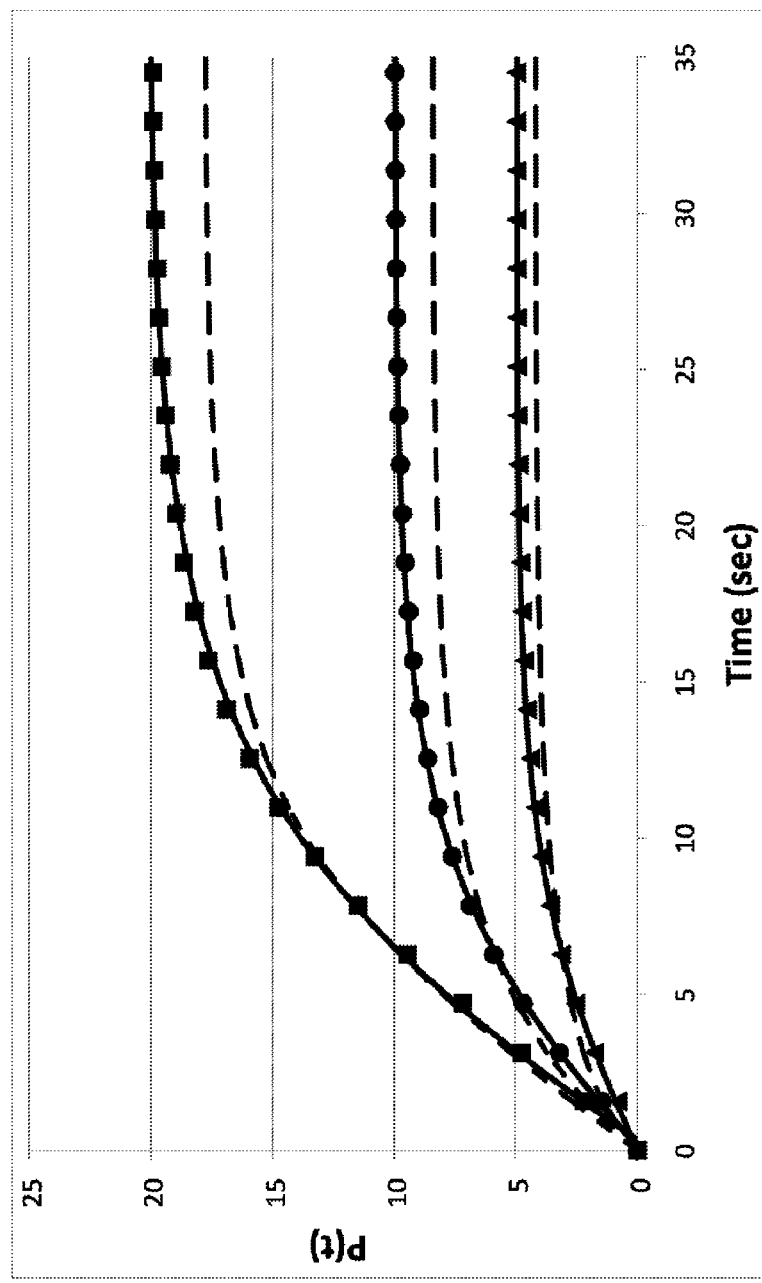
FIG. 11 shows the P(t) response function compared to data for the enzyme reaction modeling, according to some embodiments.

FIG. 11 shows the P(t) response function compared to data for the enzyme reaction modeling, according to some embodiments. As shown in FIG. 11, the solution for P(t) using the system of differential equations (Equations (21)-(24)) can be compared to P(t) obtained using the Michaelis-Menten approximation and to that obtained using the systems and methods taught herein, for $S_0$ values of 5.0, 10.0, and 20.0. The symbols represent the solution for P(t) from the system of differential equations, the dashed line represents the solution for P(t) using the Michaelis-Menten approximation, and the solid line represents the solution for P(t) using the systems and methods taught herein. The lowest lines are the solutions for the $S_0=5.0$ case, the middle set of lines are the solutions for the $S_0=10.0$ case, and the top lines are the solutions for the $S_0=20.0$ case. As can be readily seen from FIG. 11, the state-of-the-art method of using the Michaelis-Menten approximation shows a substantially inferior predictive power than the systems and methods taught herein.

One of skill will appreciate that the systems and methods taught herein provide a much more accurate representation for the solution of the system of differential equations over the entire range of initial substrate concentrations.

Example 3

Pharmacodynamic Modeling

This example compares the results of a published pharmacodynamic model to a model constructed using the systems and methods taught herein. From this example, one of skill will appreciate that the systems and methods taught herein provide a more accurate viral load response prediction than that obtained using the published, state-of-the-art large-scale compartmental model which contains many compartments, differential equations, nonlinear reactions, and parameters.

While PK models are used to describe the fate of substances administered externally to a living organism, pharmacodynamic (PD) models are used to describe the response of some system entity to the introduction of a substance administered externally. It is often said that PK models describe what the body does to a drug, whereas PD models describe what the drug does to the body. In terms of input-response, PK models describe the response of the input compound upon introduction into the body, while PD models describe the response of some other system entity after introduction of a certain compound. Both are input-response models, but in PD modeling, the response of interest is a system component that is different than the input compound. For example, a PD model might describe the amount of a certain type of infectious bacteria that is present over time after introduction of a specific antibiotic; whereas, a PK model would describe the fate of the antibiotic over time.

The published model is a PD model designed to predict HIV viral load response to the administration of the drug tenofovir in oral doses of 75, 150, 300, and 600 mg. See Duwal, S., et al. PLoS One, 7(7):e40382 (2012), which is hereby incorporated herein by reference in its entirety. The published PD model is coupled to a pharmacokinetic model, a four-compartment model containing both linear and nonlinear Michaelis-Menten kinetics, and it consists of a nonlinear system of eight differential equations. As such, the coupled pharmacokinetic-pharmacodynamic model is a mechanistic model containing 12 species and 31 free parameters. As a virus dynamics model, it was used to predict viral loads following tenofovir treatment in HIV-infected patients.

Figure 12A:
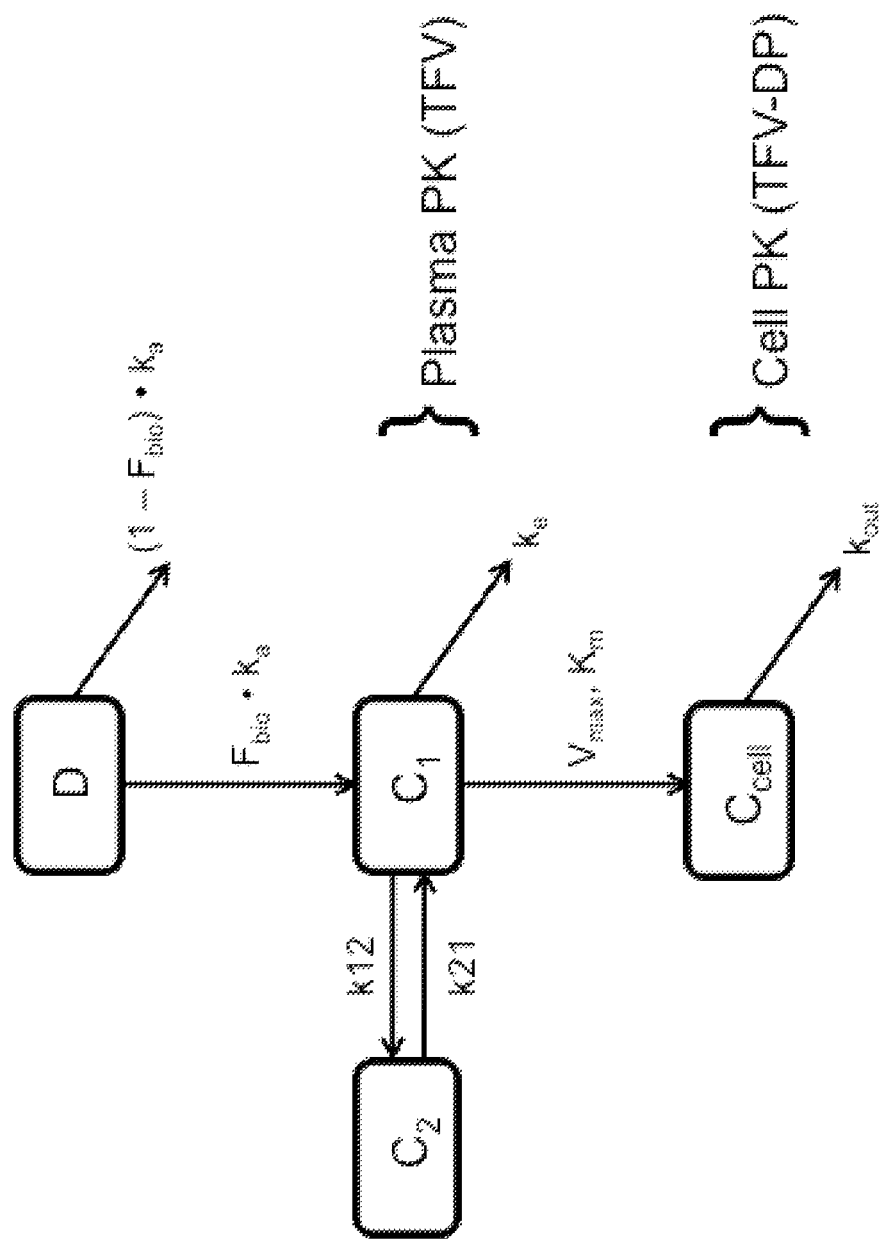
FIGS. 12A and 12B illustrate the pharmacokinetic and pharmacodynamic model as used in predicting viral loads in response to administration of tenofovir, according to some embodiments.
Figure 12B:
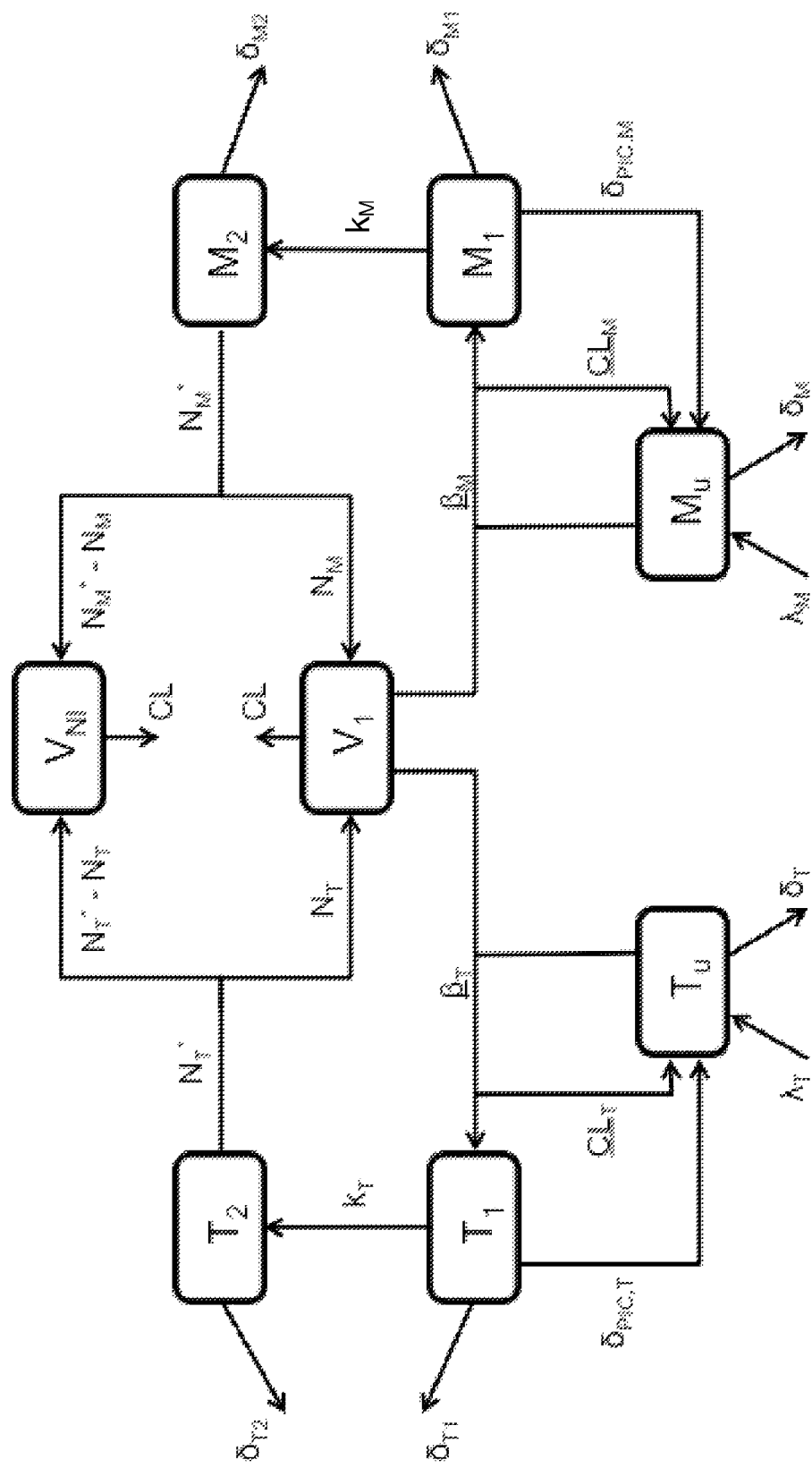

FIGS. 12A and 12B illustrate the pharmacokinetic and pharmacodynamic model as used in predicting viral loads in response to administration of tenofovir, according to some embodiments. FIG. 12A is a drawing of a pharmacokinetic model of the system, and FIG. 12B is a drawing of a virus dynamics model. In FIG. 12A, D refers to an input dose of tenofovir disoproxil fumurate (TDF), an antiviral pro-drug, in a subject. With respect to plasma PK, $C_1$ is a compartment that resembles plasma pharmacokinetics, and $C_2$ is a compartment for the poorly perfused (peripheral) tissues in the pharmacokinetic model. With respect to cell PK, $C_{cell}$ resembles the concentrations of tenofovir disphosphate (TFV-DP) in peripheral blood mononuclear cells. Parameters $k_{12}$ and $k_{21}$ are the rate constants for influx and outflux to/from the peripheral compartment $C_2$, and $k_a$ and $k_e$ are the rates of TFV uptake for the elimination into/out-of $C_1$, respectively. $F_{bio}$ is bioavailability. $V_{max}$ and $k_m$ are Michaelis-Menten kinetics parameters, and $k_{out}$ is the cellular elimination rate constant of TFV-DP. See, for example, pages 2 and 3 of Duwal, S., et al. PLoS One, 7(7):e40382 (2012).

FIG. 12B is coupled to FIG. 12A in that the $\beta_T$, $\beta_M$, $CL_T$, and $CL_M$ parameters in the pharmacodynamics model are functions of the $C_{cell}$ concentration from the pharmacokinetics model. In FIG. 12B, In brief, the virus dynamics model comprises T-cells, macrophages, free non-infectious virus ($T_U$, $M_U$, $V_{NI}$, respectively), free infectious virus $V_1$, and four types of infected cells: infected T-cells and macrophages prior to proviral genomic integration ($T_1$ and $M_1$, respectively) and infected T-cells and macrophages after proviral genomic integration ($T_2$ and $M_2$, respectively). $\lambda_T$ and $\lambda_M$ are the birth rates of uninfected T-cells and macrophages, and $\delta_T$ and $\delta_M$ denote their death rate constants. The parameters $\delta_{PIC,T}$ and $\delta_{PIC,M}$ refer to the intracellular degradation of essential components of the pre-integration complex, e.g., by the host cell proteasome, which return early infected T-cells and macrophages to an uninfected stage, respectively. Parameters $\beta_T$ and $\beta_M$ denote the rate of successful virus infection of T-cells and macrophages in the presence of TFV-DP, respectively, while the parameters $CL_T$ and $CL_M$ denote the clearance of virus through unsuccessful infection of T-cells and macrophages in the presence of TFV-DP. Parameters $k_T$ and $k_M$ are the rate constants of proviral integration into the host cell's genome and $N_T^*$ and $N_M^*$ denote the total number of released infectious and non-infectious virus from late infected T-cells and macrophages and $N_T$ and $N_M$ are the rates of release of infectious virus. The parameters $\delta_{T1}$, $\delta_{T2}$, $\delta_{M1}$ and $\delta_{M2}$ are the death rate constants of $T_1$, $T_2$, $M_1$, and $M_2$ cells, respectively. The free virus (infectious and non-infectious) gets cleared by the immune system with the rate constant CL. See, for example, pages 3 and 4 of Duwal, S., et al. PLoS One, 7(7):e40382 (2012).

The complicated modeling shown by FIGS. 12A and 12B can be simplified using the systems and methods taught herein. It was found, for example, that using the systems and methods taught herein, which includes using Equation (9), a three-term model was sufficient. Optimization of the response variables for the viral load function gives the following optimized values of the variables as shown in Table 3:

TABLE 3

| K | $K_p$ | $\alpha_p$ | term i | $M_i^0$ | $M_i^1$ | $N_i^0$ | $N_i^1$ |
|---|---|---|---|---|---|---|---|
| 0.233 | 5.010 | 0.0211 | 0 | 0.76 | 0.14 | — | — |
| | | | 1 | 26.21 | 7.63 | 0.0007 | 0.0054 |
| | | | 2 | −5.24 | 2.68 | −0.0004 | 0.0131 |

Figure 13:
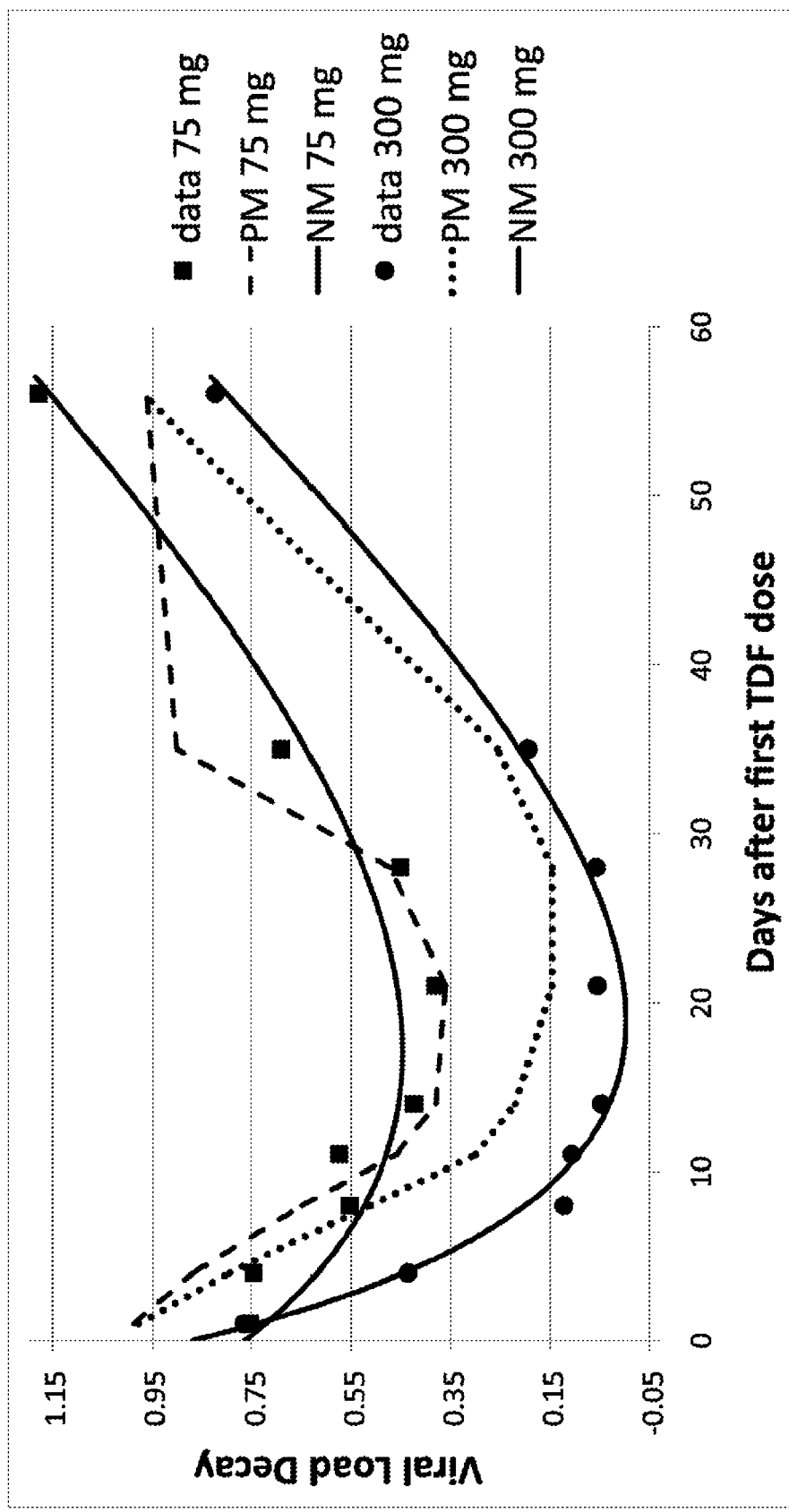
FIG. 13 shows a plot of the responses provided using the systems and methods taught herein as compared to the large-scale compartment model, according to some embodiments.

FIG. 13 shows a plot of the responses provided using the systems and methods taught herein as compared to the large-scale compartment model, according to some embodiments. The published model (PM) was taken from Duwal, et al. See Duwal, S., et al. PLoS One, 7(7):e40382 (2012), as described herein. The systems and methods taught herein are the new model (NM) and are compared to PM. Dashed and dotted lines represent PM, the predicted median viral kinetics, using the model of Duwal. The symbols represent actual data points from the observed viral kinetics, and the solid lines represent predicted responses using the systems and methods taught herein, NM. Once daily 75 mg TDF dosing and once daily 300 mg TDF dosing are shown.

As shown in FIG. 13, the new model is able to accurately capture the same input-response behavior that is produced by the larger mechanistic model. This increased level of accuracy is important not only in dosing studies of tenofovir but also in creating more accurate predictions of viral load response to test input compounds other than tenofovir. Surprisingly, the systems and methods taught herein functioned very well with only 13 response variables rather than the 31 model parameters used by the state-of-the-art model. As such, the systems and methods taught herein are less prone to the ambiguity in model parameter to solution mapping that is present in a mechanistic model. One of skill will appreciate this surprising and unexpected control over such ambiguities, particularly if one were to try to make predictions of the pharmacodynamic response based on properties of input compounds.

Example 4

Quantitative Structure-Activity Relationship (QSAR) Predictions

This example shows that the systems and methods taught herein can be used to determine quantitative structure-activity relationships (QSAR), the mapping of molecular structure properties of an input compound to a response, or activity, within a given system. QSAR allows one of skill, for example, to (i) summarize a relationship between chemical structures and biological activity in a dataset of chemicals; and (ii) predict the activities of new chemicals. It is this same type of characterization and prediction that can be obtained with the systems and methods taught herein, significantly impacting a wide variety of fields, including drug design and personalized medicine. One of skill will appreciate that the systems and methods taught herein can be used to relate properties of an input to a particular response profile and address the desire to relate the variables of an input-response model (the model parameters in a mechanistic model or the response function variables in the systems and methods taught herein, for example) to properties of the input. Moreover, one of skill will also appreciate the systems and methods taught herein for their ability to relate parameters of a dose response model in drug design to the molecular properties of a proposed drug (input compound). The accurate mapping of input molecular properties to model parameters allows the art to input compounds covering a wide range of molecular properties and get an accurate description of the resulting response for each. Accordingly, the systems and methods taught herein provide the basis for an 'in silico' screening process, where one could select an input compound that yields the most desirable response.

Mechanistic models lack the necessary one-to-one relationships between model parameters and model output. As demonstrated in previous examples, this is why such mechanistic models are often unable to produce sufficient maps of input properties to model parameters. This is a problem of "a lack of specificity," in that it is possible to achieve the same output from many different sets of model parameters. Unfortunately, this lack of specificity between parameters and output is a serious problem in that it becomes impossible to expose unique input-response relationships. For example, by way of ambiguous parameters, the same input could produce a wide range of responses, or many different inputs could produce the same response. The systems and methods taught herein, however, can reduce or even eliminate this ambiguity, and allow for more accurate mappings between input properties and output (response) profiles via the response function variables.

Using Molecular Properties to Select Drug Candidates

Molecular properties are often used to determine if a chemical compound with a certain pharmacological or biological activity has properties that would make it a likely orally active drug in humans. Such properties can include, but are not limited to, number of hydrogen bond donors, number of hydrogen bond acceptors, molecular weight, octanol-water partition coefficient, electrostatic potential, surface charge, surface potential, density, ionization energy, $H_{vaporization}$, $H_{hydration}$, lipophilicity parameter, $pK_a$, boiling point, refractive index, dipole moment, reduction potential, ovality, HOMO energy, polarizability, molecular volume, vdW surface area, molecular refractivity, hydration energy, surface area, LUMO energy, charges on individual atoms, solvent accessible surface area, maximum + and − charge, hardness, Taft's steric parameter, 3D configuration of atoms, and secondary structure such as helices, beta strands, beta sheets, coils, and loops. Molecular properties that are more geometrical in nature are used, for example, to determine if a chemical compound meets the essential, or desired, structural parameters for binding with a receptor. Because the systems and methods taught herein can remove much of the ambiguity between input properties and response profiles, they will be more likely to make accurate mappings from biological activity and structural properties of candidate drug molecules to response profiles. As such, the systems and methods taught herein can provide an extremely valuable tool for pre-clinical modeling and prediction of activity against a given target, or PK-ADME (absorption, distribution, metabolism, and excretion) properties of candidate drug compounds.

The Problem of Ambiguity in Current, State-of-the-Art Modeling

To demonstrate the ambiguity that would arise in attempting to map molecular properties of an input compound to variables in the response function, consider the pharmacokinetic modeling problem presented in Example 1. As was shown in that example, there were an infinite number of model parameter values ($k_f$, $k_r$, $k_e$, $V_i$, and $V_p$) that could yield the desired values for the variables $\beta_1$, $\beta_2$, and M in the solution function $C_p(t)$ when using a linear, mechanistic, compartmental modeling approach. A typical QSAR study of this problem would attempt to map molecular properties of an input compound to model parameter values. For example, if molecular weight (W) and partition coefficient (log P) were the predominant factors in the pharmacokinetic properties of a compound, then one would attempt to describe the model parameters $k_f$, $k_r$, and $k_e$ as functions of W and log P (it is assumed that $V_i$, and $V_p$ are parameter values that would have to be estimated but would be independent of W and log P). Once such functions are constructed, the values of the response function variables ($\beta_1$, $\beta_2$, and M) would be directly determined by the molecular weight and partition coefficient of the input compound. This is shown mathematically below:

$\beta_1 = F_1(k_f, k_r, k_e) \; k_f = G_1(W, \log P)$ $\beta_2 = F_2(k_f, k_r, k_e) \; k_r = G_2(W, \log P)$ $\beta_3 = F_3(k_f, k_r, k_e) \; k_e = G_3(W, \log P)$ $\beta_1 = H_1(W, \log P) = F_1(G_1(W, \log P), G_2(W, \log P), G_3(W, \log P))$ $\Rightarrow \beta_2 = H_2(W, \log P) = F_2(G_1(W, \log P), G_2(W, \log P), G_3(W, \log P))$ $M = H_3(W, \log P) = F_3(G_1(W, \log P), G_2(W, \log P), G_3(W, \log P))$ (26)

Therefore, given the molecular weight and partition coefficient of an input compound, the values of response function variables could be computed directly, thus giving a complete time-course pharmacokinetic profile of that compound. Examples of $F_1$, $F_2$, and $F_3$ functions were given in Example 1, Equations (10)-(12). Attempting to compute accurate molecular property to model parameter functions ($G_1$, $G_2$, and $G_3$ functions) demands a set of input-response data for input compounds covering a range of molecular properties. This data would be used to find the optimal function types and function values for the molecular property to model parameter functions.

The limitation of this approach comes from the ambiguity that is present in attempting to construct the molecular property to model parameter functions. For the sake of simplicity, consider the case where molecular weight is the only property that affects response. And consider the same pharmacokinetic problem from Example 1, where the values $\beta_1 = -0.0025$, $\beta_2 = -0.0165$, and $M = 13$ were found to provide the best fit to the given observations of response (the data sets of responses to given inputs). In that example, expressions were derived for model parameter values as functions of solution variable values (Equations (13)-(16)). These expressions showed that for a given set of $\beta_1$, $\beta_2$, and M values, there are an infinite number of model parameter values that can result. These expressions also provided bounds for the model parameter values. Thus, the molecular property to model parameter functions must be bounded in this case. There are many types of functions that can provide such bounds, but consider the functional form given in Equation (2) using only two terms:

$$G(W) = M^0 + M^1 \left( \frac{1 - e^{-\sigma W}}{1 + ce^{-\sigma W}} \right)$$

This function is bounded by $M^0 + M^1$ and $M^0 - M^1/c$. Using this form to define the parameter values as functions of W gives:

$$k_f = G_1(W) = M_1^0 + M_1^1 \left( \frac{1 - e^{-\sigma_1 W}}{1 + c_1 e^{-\sigma_1 W}} \right)$$

$$k_r = G_2(W) = M_2^0 + M_2^1 \left( \frac{1 - e^{-\sigma_2 W}}{1 + c_2 e^{-\sigma_2 W}} \right)$$

$$k_e = G_3(W) = M_3^0 + M_3^1 \left( \frac{1 - e^{-\sigma_3 W}}{1 + c_3 e^{-\sigma_3 W}} \right)$$

Equation (13) from Example 1 gives the allowable range for $k_f$ as a function of the given $\beta_1$ and $\beta_2$, and the calculated $V_i$.

$$-\beta_1 \leq \frac{k_f}{V_i} \leq -\beta_2 \Rightarrow -\beta_1 \leq \frac{G_1(W)}{V_i} \leq -\beta_2$$

Since $G_i(W)/V_i$ is bounded by $(1/V_i)(M_1^0 + M_1^1)$ and $(1/V_i)(M_1^0 - M_1^1/c_1)$ then $$-\beta_1 \leq \frac{1}{V_i}(M_1^0 + M_1^1) \leq -\beta_2$$

and $$-\beta_1 \leq \frac{1}{V_i}\left(M_1^0 - \frac{M_1^1}{c_1}\right) \leq -\beta_2$$

$$\Rightarrow |M_1^1|\left(1 + \frac{1}{c_1}\right) < (\beta_1 - \beta_2)V_i$$

$$-\beta_1 V_i - M_1^1 \leq M_1^0 \leq -\beta_2 V_i + \frac{M_1^1}{c_1} \quad \text{(if } M_1^1 < 0\text{)}$$

$$-\beta_1 V_i + \frac{M_1^1}{c_1} \leq M_1^0 \leq -\beta_2 V_i - M_1^1 \quad \text{(if } M_1^1 > 0\text{)};$$

Where, $\beta_1<0$, $\beta_2<0$, $V_i>0$, $M_1^0>0$, and $c_1>0$. There are no constraints placed on (i.e., $-\infty \le 0 \le \infty$).

Thus, the allowable values for $M_1^0$, $M_1^1$, and $c_1$, are given by the $\beta_1$, $\beta_2$, and $V_i$ values obtained from fitting the data. Thus, there are an infinite number of values for the variables ($M_1^0$, $M_1^1$, and $c_1$) that describes the relationship between the molecular property W and the model parameter $k_f$. This will also be true of the variables describing the relationship between the molecular property W and the model parameters $k_r$ and $k_e$. Depending on the values of $\beta_1$, $\beta_2$, and $V_i$, the range of allowable values for $M_1^0$, $M_1^1$, and $c_1$ could be quite large.

There are, of course, other types of nonlinear functional forms that could be used for the G(W) functions, but all will introduce additional parameters and the same type of ambiguity will result. Therefore, the non-unique mappings that exist between model parameters and response functions in a mechanistic model will extend to the mappings between input molecular properties and model parameters in a QSAR study. This will result in a non-unique mapping between input molecular properties and output response functions. Such a non-unique mapping will make it prohibitively difficult to obtain accurate and effective QSAR predictions.

Using the Systems and Methods Taught Herein; Eliminating Mechanistic Modeling Parameters to Reduce Ambiguity The approach for QSAR prediction using the systems and methods taught herein is to start with input-response data for input compounds having a wide range of molecular properties. For each compound, various doses would be tested and a model can be built using the new formulation; i.e., optimal values would be found for the response function variables K, $K_p$, $\alpha_p$, $M_0^0$, ..., $M_n^0$, $M_0^1$, ..., $M_n^0$, $N_1^0$, ..., $N_n^0$ and $N_1^1$, ..., $N_n^1$. A mapping can then be constructed between the molecular properties of the input compounds and the optimal values of the response function variables. Once this mapping, or set of functions, is found, then predictions can be made as to what type of response will result from introduction of a given compound into the system. All that would be required as input is the specific values of the molecular properties of a compound. These values would then uniquely determine the values of the response function variables in the systems and methods taught herein, which would give a time-course profile of the desired response. Using that time-course profile, one could evaluate the effectiveness of the input compound in achieving a desired response. The mapping from molecular properties to response functions will contain less ambiguity because it eliminates the intermediate step of mechanistic model parameters. It will be much more likely to obtain accurate mappings between input molecular properties and response function variables because of the reduction in ambiguity. With such mappings, virtual screenings can be performed to assess the likelihood that a particular input compound will produce a desired response. A mathematical description of the QSAR process using the systems and methods taught herein is given below.

Using available data, models would be set up for each input compound based on the observed responses due to various doses. Each of these models would contain optimal values of the response function variables K, $K_p$, $\alpha_p$, $M_0^0$, ..., $M_n^0$, $M_0^1$, ..., $M_n^1$, $N_1^0$, ..., $N_n^0$ and $N_1^1$, ..., $N_n^1$. From these models, functions would be fit that map molecular properties of the input to the variables in the response function. These functions are analogous to the H functions that were composed in the mechanistic case (Equations (26)). For example, if molecular weight, W, and partition coefficient log P were the only molecular properties considered, there would be 4n+5 functions, where n is the number of the final term in the response function. Using the optimal values of response function variables that were derived for each input compound, and the molecular weight and partition coefficient of each compound, the following functions (mappings) would be estimated:

$$K = H_1(W, \log P)$$

$$K_p = H_2(W, \log P)$$

$$\alpha_p = H_3(W, \log P)$$

$$M_0^0 = H_4(W, \log P) \qquad N_1^0 = H_{2n+6}(W, \log P)$$

$$\vdots \qquad \qquad \vdots$$

$$M_n^0 = H_{n+4}(W, \log P) \qquad N_n^0 = H_{3n+5}(W, \log P)$$

$$M_0^1 = H_{n+5}(W, \log P) \qquad N_1^1 = H_{3n+6}(W, \log P)$$

$$\vdots \qquad \qquad \vdots$$

$$M_n^1 = H_{2n+5}(W, \log P) \qquad N_n^1 = H_{4n+5}(W, \log P)$$

In some embodiments, there would typically be more than two molecular properties considered, and thus the construction of the H functions would require higher-dimensional approximations. The extension to higher dimensions does not significantly alter the basic approach, but it would require additional computational cost.

Once the H functions are established, a direct connection is made from molecular weight and partition coefficient of a compound to values of the response function variables. Based on this connection, when a new compound is considered, its molecular weight and partition coefficient are used to calculate values of the variables in the response function. After calculating the values of the variables in the response function, the result is a full time-course profile of the response. This profile can then be used to assess properties such as maximum concentration, time to maximum concentration, time above a minimum concentration, clearance, permeability, size of solid tumor, etc. - - - all of which are very valuable in systems biology and drug design modeling. These predictions of response provide an extremely valuable tool by which large numbers of compounds can be screened very quickly using high-speed and large-storage computers.

Example 5

Micro-Dosinq Studies

Micro-dosing is a technique for studying the behavior of drugs in humans through the administration of doses so low ("sub-therapeutic") that they are unlikely to produce whole-body effects, but high enough to allow the cellular response to be studied. This allows us to see the PK of the drug with almost no risk of side effects. This is usually conducted before clinical Phase I trials to predict whether a drug is viable for that phase of testing. Human micro-dosing aims to reduce the resources spent on non-viable drugs and the amount of testing done on animals. As only micro-dose levels of the drug are used, analytical methods are limited and extreme sensitivity is needed. Accelerator mass spectrometry (AMS) is the most common method for micro-dose analysis. Many of the largest pharmaceutical companies have now used micro-dosing in drug development, and the use of the technique has been provisionally endorsed by both the European Medicines Agency and the Food and Drug Administration. It is expected that human micro-dosing will gain a secure foothold at the discovery-preclinical interface driven by early measurement of candidate drug behavior in humans.

There are many reasons for potential drug candidates to be dropped from the pharmaceutical pipeline. A suitable compound must demonstrate efficacy in the target patient population and have an acceptable safety profile, requirements which are themselves extremely demanding. One property of a compound that influences these and other factors is its PK profile. That is, how efficiently the compound is absorbed from the site of administration into the body, how well it is distributed to various sites within the body, including the site of action, and how rapidly and by what mechanism(s) it is eliminated, by excretion and metabolism (ADME—absorption, distribution, metabolism and excretion). Furthermore, the vast majority of compounds are metabolized, therefore the fate of the newly formed metabolites must be taken into account, as many of these are active and some have adverse side effects. It has been estimated that between 10% and 40% of potential drugs fail during early clinical trials because of unsuitable PK features. A poor PK profile may render a compound of so little therapeutic value as to be not worth developing. For example, very rapid elimination of a drug from the body would make it impractical to maintain a compound at a suitable level to have the desired effect. Clearly, the ideal is to only test in humans those compounds that have desirable PK properties. However, this is no trivial task. The problem is that despite significant progress to date generally, we are still unable to predict the PK profile in humans of many drug classes from in vitro and computer-based methods. We are therefore reliant on information gained in animals, which is based on past experience and has been the most predictive, to help screen the compounds for those with an appropriate PK profile. One commonly-applied approach to predicting a human PK profile based on animal data is allometric scaling, which scales the animal data to humans, assuming that the only difference among animals and humans is body size. While body size is an important determinant of PK, it is certainly not the only feature that distinguishes humans from animals and, therefore, this simple approach has been estimated to have less than 60% predictive accuracy.

This is where micro-dosing comes in. Clinical testing phases 1 to 3 involve evaluating pharmacological doses generally first in human volunteers and then in patients for efficacy and safety. The hypothesis is that micro-dosing will help reduce or replace the extensive testing in animals of the many compounds that do not have desirable PK properties in humans and subsequently would be rejected. But what is a micro-dose, and how could it help? A micro-dose is so small that it is not intended to produce any pharmacologic effect when administered to humans and therefore is also unlikely to cause an adverse reaction. For practical purposes this dose is defined as ¹/₁₀₀th of that anticipated to produce a pharmacological effect, or 100 micrograms, whichever is the smaller. The interest in giving such a micro-dose to humans early in the drug development process is centered on the view that many of the processes controlling the PK profile of a compound are independent of dose level. Therefore, a micro-dose will provide sufficiently useful PK information to help decide whether it is worth continuing compound development, which includes, for example, toxicity testing in animals.

Computer models can provide valuable analytical tools in the area of micro-dosing, although there are serious practical hurdles that must be resolved. As we have seen in the previous examples, a computer model that does not accurately capture all of the linear and nonlinear effects within a system will not yield accurate extrapolations of low-dose results to higher-doses. This is where the systems and methods herein will have significant positive impact, where in some embodiments they will include a dose-response model using several different micro-doses, and then extrapolate that model to higher, therapeutic doses.

Testing of the systems and methods taught herein has shown that in true micro-dosing studies, if the low-dose data used to construct the model covers a wide enough range, then accurate predictions can be made for doses that are roughly one order of magnitude higher. To illustrate this point, consider the case of intestinal drug absorption. The absorption of drugs via the oral route is a subject of intense and continuous investigation in the pharmaceutical industry since good bioavailability implies that the drug is able to reach the systemic circulation by mouth. The intestine is an important tissue that regulates the extent of absorption of orally administered drugs, since the intestine is involved in first-pass removal. A simple model of intestinal drug absorption focuses on the permeation of a drug compound across the epithelial cells that separate the blood vessels and intestines. The ability of a compound to permeate the cell layer is governed by diffusive processes as well as cell membrane transporters that can actively move compounds in the opposite direction of a concentration gradient. These transporters counteract the permeation of a compound that would occur by diffusion alone, due to a concentration gradient.

The simple model of intestinal drug absorption can be represented as a three-compartment model, where one compartment represents the intestine, one the cell layer, and the other the bloodstream. Forward and reverse diffusion rates can be set up between the compartments, and the cell membrane transporters can be represented by a non-reversible rate between the cell and the intestine. Because the capacity of the cell membrane transporters is limited, it is a "saturable" process. That is, once the transporters have become saturated with a particular compound, they can no longer accept any more and will then continue to transport at a constant rate. This type of saturable process is nonlinear and is typically modeled using Michaelis-Menten kinetics. The compartment model and associated differential equations are given below.

Figure 14:
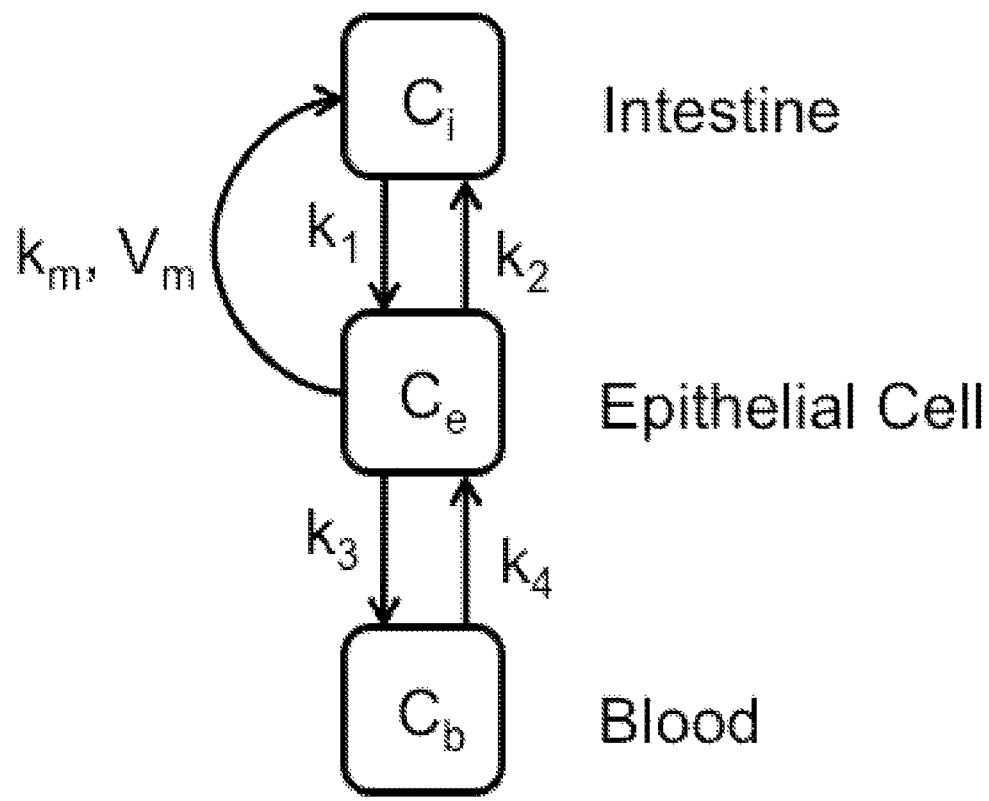
FIG. 14 shows a three-compartment model that is used as a simple representation for the absorption of a compound between the intestines and bloodstream for a dosing study, according to some embodiments.

FIG. 14 shows a three-compartment model that is used as a simple representation for the absorption of a compound between the intestines and bloodstream for a dosing study, according to some embodiments. The compartment modeling can include the following equations:

$$V_i \frac{\partial C_i}{\partial t} = -k_1 C_i + k_2 C_e + \left(\frac{V_m}{k_m + C_e}\right) C_e$$

$$V_e \frac{\partial C_e}{\partial t} = k_1 C_i - (k_2 + k_3) C_e + k_4 C_b - \left(\frac{V_m}{k_m + C_e}\right) C_e$$

$$V_b \frac{\partial C_b}{\partial t} = k_3 C_e - k_4 C_b;$$

where, $V_i$, $V_e$, and $V_b$ represent the volumes of distribution for the intestinal, epithelial cell, and bloodstream compartments, respectively; $k_1$, $k_2$, $k_3$, and $k_4$ represent the diffusion rates; and $k_m$, $V_m$ are the Michaelis-Menten rate constants for the active transport. For the purpose of this example, $V_i=V_e=V_b=1.0$, $k_1=k_2=1.0$, $k_3=k_4=5.0$, $k_m=1.0$, and $V_m=5.0$. The initial concentrations are all 0 except for the intestinal compartment whose initial condition is equal to the input dose, $C_0$.

In order to perform a dosing study, $C_0$ values of 1, 10, and 100 mg were used to construct a model of the absorption of a compound between the intestines and bloodstream using the new formulation and a linear model that does not take into account the nonlinear transport effect. It would be reasonable to expect that, given these initial values, a linear model might be chosen since that would provide a fairly accurate fit to the data. The two models were then used to predict the concentration profile in the blood compartment that results from an input dose of 1000 (one order of magnitude higher than the highest dose used to construct the model). The model results were then compared to the numerical solution of the system of differential equations (referred to as the "data"). It was found that using the systems and methods taught herein (using Equation (9)), a three-term model was sufficient for this particular example. Optimization of the response variables for the $C_b(t)$ function gives the following optimized values of the variables in the response function used by the systems and methods taught herein for the dosing study, as shown in Table 4:

TABLE 4

| K | $K_p$ | $\alpha_p$ | term i | $M_i^0$ | $M_i^1$ | $N_i^0$ | $N_i^1$ |
|---|---|---|---|---|---|---|---|
| 1.684 | 1.259 | 0.1225 | 0 | 0.0006 | −0.0049 | — | — |
| | | | 1 | 0.0211 | 0.1927 | 2.0551 | −0.0427 |
| | | | 2 | 0.1049 | −0.0003 | 5.5767 | 0.0497 |

Figure 15:
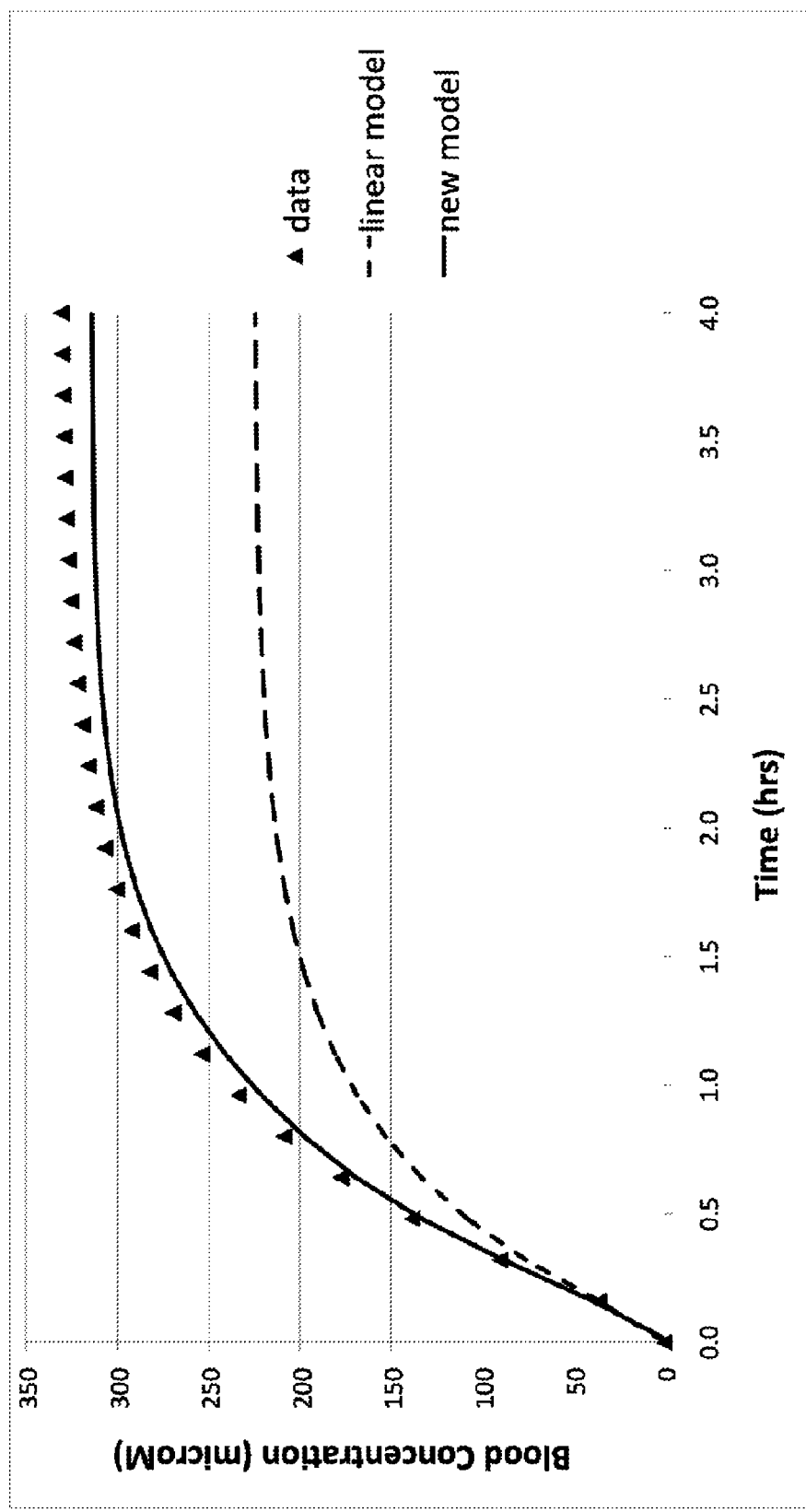
FIG. 15 shows the prediction of the bloodstream concentration vs. time profile for a 1000 mg dose, using both the linear and systems and methods taught herein, according to some embodiments.

FIG. 15 shows the prediction of the bloodstream concentration vs. time profile for a 1000 mg dose, using both the linear and systems and methods taught herein, according to some embodiments. Both (i) the linear model and (ii) the model of the systems and methods taught herein are compared to the 'data,' or numerical solution. Both the linear model and the systems and methods taught herein provide accurate fits to the $C_0$=1, 10, and 100 mg data sets (discussed as observed, but not plotted, for purposes of clarity). But, when you consider the use of the model to predict the $C_0$=1000 mg data set, FIG. 15 shows that the systems and methods taught herein provide a significantly more accurate fit to the data. This is because the systems and methods taught herein were able to pick up the nonlinear behavior due to the saturable membrane transport phenomena. It could be argued that one could adjust the mechanistic model to reflect the nonlinearity, but it may not be known a priori where the nonlinear phenomena occurs and precisely what the nonlinear kinetic rate(s) should be. The systems and methods taught herein pick up the nonlinearity automatically and are able to extend that to make accurate predictions of response due to higher-dose initial conditions.

Example 6

The Use of Surrogates in Modeling: Biomarkers and Metabolomics

This example shows how the use of surrogates for response data in modeling to predict a response. Surrogates can include, for example, biomarkers and metabolomics. If the generation of response data is prohibitively expensive or time-consuming, for example, then the use of biomarkers or metabolites allows for the construction of a model that might otherwise be impossible to build. For example, if the response of interest is the size of a solid tumor and we would like to have observations over a relatively short time scale (minutes-hours), then we would have to obtain images of the tumor every few minutes or hours, and the cost of imaging technology in itself could be prohibitive.

In some embodiments, the term "biomarker" can be used to refer a biological molecule found in blood, other body fluids, or tissues that is (i) a sign of a normal or abnormal process, or of a condition or disease; or, (ii) used to see how well the body responds to a treatment for a disease or condition. In some embodiments, A biomarker can also be called "a molecular marker" or "a signature molecule." In some embodiments, a biomarker can be diagnostic, for example, to help diagnose a cancer, perhaps before it is detectable by conventional methods. In some embodiments, a biomarker can be prognostic, for example, to forecast how aggressive the disease process is and/or how a patient can expect to fare in the absence of therapy. And, in some embodiments, a biomarker can be predictive, for example, to help identify which patients will respond to which drugs. For example, biomarker can be used as a surrogate indication of the progression of a tumor, for example, the measurement of which can be less time-consuming and costly than the measurement of the tumor size. The prostate-specific antigen (PSA) is an example of a protein produced by cells of the prostate gland that can be measured in blood samples, as prostate cancer can increase PSA levels in the blood, making PSA a biomarker for prostate tumors. Other examples of biomarkers include, but are not limited to, C reactive protein (CRP) for inflammation; high cholesterol for cardiovascular disease; S100 protein for melanoma; HER-2/neu gene for breast cancer; BRCA genes for breast and ovarian cancers (BRCA1 and BRCA2); CA-125 for ovarian cancer; BNP in heart failure, CEA in colorectal cancer; creatine levels in renal failure; cerebral blood flow for Alzheimer's disease, stroke, and schizophrenia; high body temperature for infection; and, the size of brain structures for Huntington's disease.

Metabolomics uses metabolites as the intermediates and products of metabolism, and metabolomics can be used in input-response modeling, for example, in the area of drug toxicity assessment. In some embodiments, metabolic profiling of a body fluid can be used as a surrogate. In some embodiments, metabolic profiling of urine or blood plasma can be used as a surrogate, for example, to detect the physiological changes caused by toxic insult of a chemical. Pharmaceutical companies can use metabolomics in modeling, for example, to test the toxicity of potential drug candidates: if a compound can be eliminated before it reaches clinical trials on the grounds of adverse toxicity, it saves the enormous expense of the trials. In some embodiments, the metabolite that is profiled can be an endogenous metabolite produced by the subject, an exogenous metabolite, or a xenometabolite produced by a foreign substance such as a drug. In some embodiments, a metabolite can include, but are not limited to, a lipoprotein or albumin.

In some embodiments, phenylanine and tyrosine concentrations can be used for diagnosing inborn errors of metabolism (IEM), as they are considered as potentially the most clinically applicable metabolic biomarkers in combination with glucose for diabetes diagnosis.

In some embodiments, metabolites can be used in cancer studies. For example, a subset of six metabolites (sarcosine, uracil, kynurenine, glycerol-3-phosphate, leucine and proline) have shown to be significantly elevated upon disease progression from benign to clinically localized prostate cancer and metastatic prostate cancer. One metabolite, sarcosine, has been identified as a potential candidate for future development in biomarker panels for early disease detection and aggressivity prediction in prostate cancer. Components of a mammalian system that can be used in such studies include, for example, plasma, tissue and urine. Blood serum can be used, for example, as the component in studies of renal cancer colorectal cancer, pancreatic cancer, leukemia, ovarian cancer, and oral cancer. Urine can be used, for example, as the component in studies of breast cancer, ovarian cancer, cervical cancer, hepatocellular carcinoma, and bladder cancer. And, saliva can be used, for example, as the component in studies of oral cancer, pancreatic cancer, and breast cancer, as well as periodontal disease.

In some embodiments, metabolites can be used in cardiovascular studies. For example, pseudouridine, citric acid, and the tricarboxylic acid cycle intermediate 2-oxoglutarate can be used in some embodiments as serum biomarkers. Cardiovascular conditions can include myocardial ischemia and coronary artery disease. In some embodiments, dicarboxylacylcarnitines can be used to predict death/myocardial infarction outcomes. And, in some embodiments, plasma levels of asymmetric dimethylarginine can be used to predict major adverse cardiac events in patients with acute decompensated heart failure and with chronic heart failure.

All of the previous examples - - - PK modeling (Example 1), enzyme reaction modeling (Example 2), PD modeling (Example 3), QSAR predictions (Example 4), and microdosing studies (Example 5) - - - rely on response data in order to build a model. Accordingly, surrogates such as biomarkers and metabolomics can be used as a means to obtain response data to build a useful model, particularly where the generation of response data is prohibitively expensive or time-consuming.

Example 7

Ex Vivo Testing and Personalized Medicine

Ex vivo testing results can be used to build the models for use with the systems and methods taught herein. The term "ex vivo" can be used to refer to experimentation or measurements done in or on tissue in an environment outside the organism with minimum alteration of natural conditions. Ex vivo conditions allow experimentation under more controlled conditions than is possible in in vivo experiments (in the intact organism), at the expense of altering the "natural" environment. A primary advantage of using ex vivo tissues is the ability to perform tests or measurements that would otherwise not be possible or ethical in living subjects. Examples of ex vivo testing would be studying the growth of bacteria in human cells and the associated antimicrobial activity of potential antibiotics; or, studying the chemosensitivity of fresh human hematopoietic cells, as well as malignant cells, in order to select drugs with preferential toxicity to malignant cells.

As such, the results of ex vivo testing can be used to construct input-response models of a particular subject and, based on that model, make predictions as to what types of therapeutic compounds might be effective in yielding a desired response within that subject. These models would have to be able to capture the complex, nonlinear behavior that is present in cell-, tissue-, and organ-scale processes. The ability of the systems and methods taught herein to quickly provide accurate and robust models of complex, nonlinear phenomena, as demonstrated in the previous examples, makes them useful in the application of ex vivo testing. One of skill will appreciated the significant impact in the area of personalized medicine made possible by the systems and methods taught herein; i.e., developing drug therapies at a dosage that is most appropriate for an individual patient.

Example 8

Demand Forecasting

The systems and methods taught herein have many potential applications outside of systems biology and drug design. For example, an important area of application is demand forecast modeling, where the input could be an individual consumer and the response is a product or service that individual might choose or require in the future. These products or services could be, for example, retail consumer products, health care services, or internet web sites.

In the case of QSAR modeling for biological applications, a model is built using available data and the molecular properties of an input compound are mapped to the parameters of the model. This mapping is then used to predict a certain response of interest based on the molecular properties of the input. In the case of demand forecasting, a model would be built using available data on individuals and their observed demand for products and services. The specific attributes of those individuals could then be mapped to the parameters of the demand model.

Using demand forecasting for mapping, one could predict a future demand for products and services based solely, for example, on one or more specific attributes of an individual. This type of modeling, and the predictions they would allow, would be very valuable for consumer products manufacturers, health care service providers, and those trying to reach potential customers through online web services.

Example 9

Implementation of the Algorithms and Optimization of Response Function Variables This example shows the implementation of the algorithms and optimization of response function variables for use in the systems and methods taught herein.

9.1 Algorithm

Take the following steps:

1) Read in data: $t_i$, $f_i$; i=1, . . . , npts, where npts is the total number of points in all the data sets;
2) Normalize all data values: $f_i^* = f_i/\text{scale}$, where:

$$fscale = \begin{cases} C_0, & \text{if response species is the same as input species} \\ 1, & \text{otherwise;} \end{cases}$$

3) Transform data:

$$\hat{t}_i = \frac{t_i}{t_{max}},$$

-continued where $t_{max}$ is the largest $t_i$ value (smallest $t_i$ value is assumed to be 0)

$$\hat{f}_i = \frac{f_i^* + f_{max}^* - 2f_{min}^*}{f_{max}^* - f_{min}^*},$$

where $f_{min}^*$ and $f_{max}^*$ are the smallest and largest $f_i^*$ values;

4) Fit data to the equation:

$$\hat{M}_0^0 + \hat{M}_0^1 (\text{kernel}) + [\hat{M}_1^0 + \hat{M}_1^1 (\text{kernel})] \quad (27)$$

$$\left\{ \frac{1 - e^{[\hat{N}_1^0 + \hat{N}_1^1 (\text{kernel})]\hat{t}}}{1 + (e^K - 2)e^{[\hat{N}_1^0 + \hat{N}_1^1 (\text{kernel})]\hat{t}}} \right\} + \ldots + [\hat{M}_n^0 + \hat{M}_n^1 (\text{kernel})]$$

$$\left\{ \frac{1 - e^{[\hat{N}_n^0 + \hat{N}_n^1 (\text{kernel})]\hat{t}}}{1 + (e^K - 2)e^{[\hat{N}_n^0 + \hat{N}_n^1 (\text{kernel})]\hat{t}}} \right\} = \hat{f};$$

where kernel is defined as:

$$\text{kernel} \equiv \frac{1 - e^{-\alpha_P C_0}}{1 + (e^{K_P} - 2)e^{-\alpha_P C_0}}$$

and this is done by minimizing the following objective function for $K$, $K_p$, $\alpha_p$, $\hat{M}_0^0, \ldots, \hat{M}_n^0, \hat{M}_0^1, \ldots, \hat{M}_n^1$, $\hat{N}_1^0, \ldots, \hat{N}_n^0$, and $\hat{N}_1^1, \ldots, \hat{N}_n^1$ (see section 9.2 for details of the minimization procedure):

$$F = \sum_{i=1}^{npts} \left\{ [\hat{M}_0^0 + \hat{M}_0^1 (\text{kernel})] + [\hat{M}_1^0 + \hat{M}_1^1 (\text{kernel})] \right. \quad (28)$$

$$\left\{ \frac{1 - e^{[\hat{N}_1^0 + \hat{N}_1^1 (\text{kernel})]\hat{t}_i}}{1 + (e^K - 2)e^{[\hat{N}_1^0 + \hat{N}_1^1 (\text{kernel})]\hat{t}_i}} \right\} + \ldots + [\hat{M}_n^0 + \hat{M}_n^1 (\text{kernel})]$$

$$\left. \left\{ \frac{1 - e^{[\hat{N}_n^0 + \hat{N}_n^1 (\text{kernel})]\hat{t}_i}}{1 + (e^K - 2)e^{[\hat{N}_n^0 + \hat{N}_n^1 (\text{kernel})]\hat{t}_i}} \right\} - \hat{f}_i \right\}^2$$

5) Transform response function variables back to original space $(t_i, f_i)$:

$$\hat{M}_0^0 = \frac{M_0^0 + f_{max}^* - 2f_{min}^*}{f_{max}^* - f_{min}^*} \Leftrightarrow M_0^0 = \hat{M}_0^0 (f_{max}^* - f_{min}^*) - f_{max}^* + 2f_{min}^*$$

$$\hat{M}_j^0 = \frac{M_j^0}{f_{max}^* - f_{min}^*} \Leftrightarrow M_j^0 = (f_{max}^* - f_{min}^*)\hat{M}_j^0; j = 1, \ldots, n$$

$$\hat{M}_j^1 = \frac{M_j^1}{f_{max}^* - f_{min}^*} \Leftrightarrow M_j^1 = (f_{max}^* - f_{min}^*)\hat{M}_j^1; j = 0, \ldots, n$$

$$\hat{N}_j^0 = N_j^0 t_{max} \Leftrightarrow N_j^0 = \frac{\hat{N}_j^0}{t_{max}}; j = 1, \ldots, n$$

$$\hat{N}_j^1 = N_j^1 t_{max} \Leftrightarrow N_j^1 = \frac{\hat{N}_j^1}{t_{max}}; j = 1, \ldots, n.$$

This will yield a final response function in terms of time and initial dose, $$f(t) = [M_0^0 + M_0^1 (\text{kernel})](fscale) + [M_1^0 + M_1^1 (\text{kernel})](fscale) \quad (29)$$

$$\left\{ \frac{1 - e^{[N_1^0 + N_1^1 (\text{kernel})]t}}{1 + (e^K - 2)e^{[N_1^0 + N_1^1 (\text{kernel})]t}} \right\} + \ldots + [M_n^0 + M_n^1 (\text{kernel})]$$

$$(fscale) \left\{ \frac{1 - e^{[N_n^0 + N_n^1 (\text{kernel})]t}}{1 + (e^K - 2)e^{[N_n^0 + N_n^1 (\text{kernel})]t}} \right\};$$

and, this function will serve as the prediction for a full time-course response for a given dose. Transforming equation 27 into equation 29:

Substituting relationships from [3.] and [5.] into Equation (27) gives:

$$\frac{M_0^0 + f_{max}^* - 2f_{min}^*}{f_{max}^* - f_{min}^*} + \frac{M_0^1 (\text{kernel})}{f_{max}^* - f_{min}^*} + \left[ \frac{M_1^0}{f_{max}^* - f_{min}^*} + \frac{M_1^1 (\text{kernel})}{f_{max}^* - f_{min}^*} \right]$$

$$\left\{ \frac{1 - e^{[N_1^0 (t_{max}) + N_1^1 (t_{max})(\text{kernel})]\frac{t}{t_{max}}}}{1 + (e^K - 2)e^{[N_1^0 (t_{max}) + N_1^1 (t_{max})(\text{kernel})]\frac{t}{t_{max}}}} \right\} + \ldots + \left[ \frac{M_n^0}{f_{max}^* - f_{min}^*} + \right.$$

$$\left. \frac{M_n^1 (\text{kernel})}{f_{max}^* - f_{min}^*} \right]$$

$$\left\{ \frac{1 - e^{[N_n^0 (t_{max}) + N_n^1 (t_{max})(\text{kernel})]\frac{t}{t_{max}}}}{1 + (e^K - 2)e^{[N_n^0 (t_{max}) + N_n^1 (t_{max})(\text{kernel})]\frac{t}{t_{max}}}} \right\} = \frac{f^* + f_{max}^* - 2f_{min}^*}{f_{max}^* - f_{min}^*}$$

Cancelling the $f_{max}^* - f_{min}^*$ and $t_{max}$ terms gives:

$$M_0^0 + f_{max}^* - 2f_{min}^* + M_0^1 (\text{kernel}) + [M_1^0 + M_1^1 (\text{kernel})]$$

$$\left\{ \frac{1 - e^{[N_1^0 + N_1^1 (\text{kernel})]t}}{1 + (e^K - 2)e^{[N_1^0 + N_1^1 (\text{kernel})]t}} \right\} + \ldots + [M_n^0 + M_n^1 (\text{kernel})]$$

$$\left\{ \frac{1 - e^{[N_n^0 + N_n^1 (\text{kernel})]t}}{1 + (e^K - 2)e^{[N_n^0 + N_n^1 (\text{kernel})]t}} \right\} = f^* + f_{max}^* - 2f_{min}^*;$$

The $f_{max}^*$ and $2 f_{min}^*$ terms cancel out, and $f^* = f/fscale$, which gives:

$$M_0^0 + M_0^1 (\text{kernel}) + [M_1^0 + M_1^1 (\text{kernel})]$$

$$\left\{ \frac{1 - e^{[N_1^0 + N_1^1 (\text{kernel})]t}}{1 + (e^K - 2)e^{[N_1^0 + N_1^1 (\text{kernel})]t}} \right\} + \ldots + [M_n^0 + M_n^1 (\text{kernel})]$$

$$\left\{ \frac{1 - e^{[N_n^0 + N_n^1 (\text{kernel})]t}}{1 + (e^K - 2)e^{[N_n^0 + N_n^1 (\text{kernel})]t}} \right\} = \frac{f}{fscale}$$

Multiplying both sides by fscale gives:

$$[M_0^0 + M_0^1 (\text{kernel})](fscale) + [M_1^0 + M_1^1 (\text{kernel})](fscale)$$

$$\left\{ \frac{1 - e^{[N_1^0 + N_1^1 (\text{kernel})]t}}{1 + (e^K - 2)e^{[N_1^0 + N_1^1 (\text{kernel})]t}} \right\} + \ldots + [M_n^0 + M_n^1 (\text{kernel})]$$

$$(fscale) \left\{ \frac{1 - e^{[N_n^0 + N_n^1 (\text{kernel})]t}}{1 + (e^K - 2)e^{[N_n^0 + N_n^1 (\text{kernel})]t}} \right\} = f;$$

which is equivalent to Equation (29).

9.2 Optimization of Response Function Variables

The optimization procedure consists of a set of nested optimizations for the response function variables K, $K_p$, $\alpha_p$, and the $\hat{N}_j^0$ and $\hat{N}_j^1$'s:

Perform a one-dimensional bounded search to find the K value (note: there is only one K value across multiple data sets within a given experiment) that minimizes a function whose value is determined by Performing a one-dimensional bounded search to find the $K_p$ value that minimizes a function whose value is determined by Performing a one-dimensional bounded search to find the $\alpha_p$ value that minimizes a function whose value is determined by Cycling through a series of two-dimensional bounded, adaptive grid-refinement searches to find the $\hat{N}_j^0$ and $\hat{N}_j^1$ values that minimize the objective function F, Equation (28)

To calculate $\hat{M}_j^0$ and $\hat{M}_j^1$'s, (i) start with the objective function, Equation (28), $$F = \sum_{i=1}^{npts} \left\{ \left[\hat{M}_0^0 + \hat{M}_0^1(\text{kernel})\right] + \left[\hat{M}_1^0 + \hat{M}_1^1(\text{kernel})\right] \left\{ \frac{1 - e^{[\hat{N}_1^0 + \hat{N}_1^1(\text{kernel})]\hat{t}_i}}{1 + (e^K - 2)e^{[\hat{N}_1^0 + \hat{N}_1^1(\text{kernel})]\hat{t}_i}} \right\} + \ldots + \left[\hat{M}_n^0 + \hat{M}_n^1(\text{kernel})\right] \left\{ \frac{1 - e^{[\hat{N}_n^0 + \hat{N}_n^1(\text{kernel})]\hat{t}_i}}{1 + (e^K - 2)e^{[\hat{N}_n^0 + \hat{N}_n^1(\text{kernel})]\hat{t}_i}} \right\} - \hat{f}_i \right\}^2;$$

and, (ii) solve the system of 2(n+1) linear equations that results from setting $$\frac{\partial F}{\partial \hat{M}_j^0} = 0;$$

$$j = 0, \ldots, n$$

and $$\frac{\partial F}{\partial \hat{M}_j^1} = 0;$$

$$j = 0, \ldots, n$$

$$\frac{\partial F}{\partial \hat{M}_0^0} = 2\sum_{i=1}^{npts} \{\} = 0$$

$$\frac{\partial F}{\partial \hat{M}_0^1} = 2\sum_{i=1}^{npts} (\text{kernel})\{\} = 0$$

$$\frac{\partial F}{\partial \hat{M}_1^0} = 2\sum_{i=1}^{npts} \{\} \left[ \frac{1 - e^{[\hat{N}_1^0 + \hat{N}_1^1(\text{kernel})]\hat{t}_i}}{1 + (e^K - 2)e^{[\hat{N}_1^0 + \hat{N}_1^1(\text{kernel})]\hat{t}_i}} \right] = 0$$

$$\frac{\partial F}{\partial \hat{M}_1^1} = 2\sum_{i=1}^{npts} (\text{kernel})\{\} \left[ \frac{1 - e^{[\hat{N}_1^0 + \hat{N}_1^1(\text{kernel})]\hat{t}_i}}{1 + (e^K - 2)e^{[\hat{N}_1^0 + \hat{N}_1^1(\text{kernel})]\hat{t}_i}} \right] = 0$$

$$\vdots$$

$$\frac{\partial F}{\partial \hat{M}_n^0} = 2\sum_{i=1}^{npts} \{\} \left[ \frac{1 - e^{[\hat{N}_n^0 + \hat{N}_n^1(\text{kernel})]\hat{t}_i}}{1 + (e^K - 2)e^{[\hat{N}_n^0 + \hat{N}_n^1(\text{kernel})]\hat{t}_i}} \right] = 0$$

$$\frac{\partial F}{\partial \hat{M}_n^1} = 2\sum_{i=1}^{npts} (\text{kernel})\{\} \left[ \frac{1 - e^{[\hat{N}_n^0 + \hat{N}_n^1(\text{kernel})]\hat{t}_i}}{1 + (e^K - 2)e^{[\hat{N}_n^0 + \hat{N}_n^1(\text{kernel})]\hat{t}_i}} \right] = 0;$$

where, $$\{\} = \left\{ \left[\hat{M}_0^0 + \hat{M}_0^1(\text{kernel})\right] + \left[\hat{M}_1^0 + \hat{M}_1^1(\text{kernel})\right] \left\{ \frac{1 - e^{[\hat{N}_1^0 + \hat{N}_1^1(\text{kernel})]\hat{t}_i}}{1 + (e^K - 2)e^{[\hat{N}_1^0 + \hat{N}_1^1(\text{kernel})]\hat{t}_i}} \right\} + \ldots + \left[\hat{M}_n^0 + \hat{M}_n^1(\text{kernel})\right] \left\{ \frac{1 - e^{[\hat{N}_n^0 + \hat{N}_n^1(\text{kernel})]\hat{t}_i}}{1 + (e^K - 2)e^{[\hat{N}_n^0 + \hat{N}_n^1(\text{kernel})]\hat{t}_i}} \right\} - \hat{f}_i \right\}.$$

Rearranging yields:

$$\hat{M}_0^0 \sum_{i=1}^{npts} 1 + \hat{M}_0^1 \sum_{i=1}^{npts} () + \hat{M}_1^0 \sum_{i=1}^{npts} [1] + \hat{M}_1^1 \sum_{i=1}^{npts} ()[1] + \ldots + \hat{M}_n^0 \sum_{i=1}^{npts} [n] + \hat{M}_n^1 \sum_{i=1}^{npts} ()[n] = \sum_{i=1}^{npts} \hat{f}_i$$

$$\hat{M}_0^0 \sum_{i=1}^{npts} () + \hat{M}_0^1 \sum_{i=1}^{npts} ()^2 + \hat{M}_1^0 \sum_{i=1}^{npts} ()[1] + \hat{M}_1^1 \sum_{i=1}^{npts} ()^2[1] + \ldots + \hat{M}_n^0 \sum_{i=1}^{npts} ()[n] + \hat{M}_n^1 \sum_{o=1}^{npts} ()^2[n] = \sum_{i=1}^{npts} ()\hat{f}_i$$

$$\hat{M}_0^0 \sum_{i=1}^{npts} [1] + \hat{M}_0^1 \sum_{i=1}^{npts} ()[1] + \hat{M}_1^0 \sum_{i=1}^{npts} [1]^2 + \hat{M}_1^1 \sum_{i=1}^{npts} ()[1]^2 + \ldots + \hat{M}_n^0 \sum_{i=1}^{npts} [1][n] + \hat{M}_n^1 \sum_{i=1}^{npts} ()[1][n] = \sum_{i=1}^{npts} [1]\hat{f}_i$$

$$M7\hat{M}_0^0 \sum_{i=1}^{npts} ()[1] + \hat{M}_0^1 \sum_{i=1}^{npts} ()^2[1] + \hat{M}_1^0 \sum_{i=1}^{npts} ()[1]^2 + \hat{M}_1^1 \sum_{i=1}^{npts} ()^2[1]^2 + \ldots + \hat{M}_n^0 \sum_{i=1}^{npts} ()[1][n] + \hat{M}_n^1 \sum_{i=1}^{npts} ()^2[1][n] = \sum_{i=1}^{npts} ()[1]\hat{f}_i$$

$$\vdots$$

$$\hat{M}_0^0 \sum_{i=1}^{npts} [n] + \hat{M}_0^1 \sum_{i=1}^{npts} ()[n] + \hat{M}_1^0 \sum_{i=1}^{npts} [1][n] + \hat{M}_1^1 \sum_{i=1}^{npts} ()[1][n] + \ldots + \hat{M}_n^0 \sum_{i=1}^{npts} [n]^2 + \hat{M}_n^1 \sum_{i=1}^{npts} ()[n]^2 = \sum_{i=1}^{npts} [n]\hat{f}_i$$

$$\hat{M}_0^0 \sum_{i=1}^{npts} ()[n] + \hat{M}_0^1 \sum_{i=1}^{npts} ()^2[n] + \hat{M}_1^0 \sum_{i=1}^{npts} ()[1][n] + \hat{M}_1^1 \sum_{i=1}^{npts} ()^2[1][n] + \ldots + \hat{M}_n^0 \sum_{i=1}^{npts} ()[n]^2 + \hat{M}_n^1 \sum_{i=1}^{npts} ()^2[n]^2 = \sum_{i=1}^{npts} ()[n]\hat{f}_i$$

where, () = (kernel)

and

-continued $$[j] = \left[\frac{1 - e^{[\hat{N}_j^0 + \hat{N}_j^1(kernel)]\hat{t}_i}}{1 + (e^K - 2)e^{[\hat{N}_j^0 + \hat{N}_j^1(kernel)]\hat{t}_i}}\right],$$
$$j = 1, \ldots, n$$

This yields the following system of equations, in matrix form:

$$\begin{bmatrix} \sum 1 & \sum 0 & \sum [1] & \sum 0[1] & \ldots & \sum [n] & \sum 0[n] \\ \sum 0 & \sum 0^2 & \sum 0[1] & \sum 0^2[1] & \ldots & \sum 0[n] & \sum 0^2[n] \\ \sum [1] & \sum 0[1] & \sum [1]^2 & \sum 0[1]^2 & \ldots & \sum [1][n] & \sum 0[1][n] \\ \sum 0[1] & \sum 0^2[1] & \sum 0[1]^2 & \sum 0^2[1]^2 & \ldots & \sum 0[1][n] & \sum 0^2[1][n] \\ \vdots & \vdots & \vdots & \vdots & \vdots & \vdots & \vdots \\ \sum [n] & \sum 0[n] & \sum [1][n] & \sum 0[1][n] & \ldots & \sum [n]^2 & \sum 0[n]^2 \\ \sum 0[n] & \sum 0^2[n] & \sum 0[1][n] & \sum 0^2[1][n] & \ldots & \sum 0[n]^2 & \sum 0^2[n]^2 \end{bmatrix} \begin{bmatrix} \hat{M}_0^0 \\ \hat{M}_0^1 \\ \hat{M}_1^0 \\ \hat{M}_1^1 \\ \vdots \\ \hat{M}_n^0 \\ \hat{M}_n^1 \end{bmatrix} = \begin{bmatrix} \sum \hat{f}_i \\ \sum 0\hat{f}_i \\ \sum [1]\hat{f}_i \\ \sum 0[1]\hat{f}_i \\ \vdots \\ \sum [n]\hat{f}_i \\ \sum 0[n]\hat{f}_i \end{bmatrix}.$$

When a solution to this system of equations is required, the $C_0$, $K$, $K_p$, $\alpha_p$, $\hat{N}_j^0$ and $\hat{N}_j^0$ values are known. Therefore, the $C_0$, $K_p$, and $\alpha_p$ values are used to calculate a (kernel) value, and the (kernel), $K$, $\hat{N}_j^0$ and $\hat{N}_j^0$ values are used to calculate the [j] values, (j=1, . . . , n). Given a (kernel) value and the [j] values, the linear system of equations (shown above) can be solved to give all of the $\hat{M}_j^0$ and $\hat{M}_j^1$ values (j=0, . . . , n).

I claim:

1. A non-compartmental method of predicting a non-linear, time-dependent response of a component of a system to an input into the system, the method comprising:
   identifying the system, the component, the input, and the non-linear, time-dependent response;
   wherein, the input includes a set of actual inputs and a test input, and the non-linear time-dependent response includes a set of non-linear, time-dependent actual responses and a non-linear, test response;
   obtaining the set of non-linear, time-dependent actual responses of the component to the set of actual inputs;
   using the set of actual inputs and the set of non-linear, time-dependent actual responses to provide a model for predicting the non-linear, test response to the test input, the model comprising the formula $$C(t) = [M_0^0 + M_0^1(kernel)] + [M_1^0 + M_1^1(kernel)] \quad (9)$$
$$\left\{\frac{1 - e^{-[N_1^0 + N_1^1(kernel)]\hat{t}}}{1 + (e^K - 2)e^{-[N_1^0 + N_1^1(kernel)]\hat{t}}}\right\} + \ldots + [M_n^0 + M_n^1(kernel)]$$
$$\left\{\frac{1 - e^{-[N_n^0 + N_n^1(kernel)]\hat{t}}}{1 + (e^K - 2)e^{-[N_n^0 + N_n^1(kernel)]\hat{t}}}\right\}$$

wherein,
$M^0{}_0, \ldots, M^0{}_n$ and $M^1{}_0, \ldots, M^1{}_n$ are overall scaling parameters;
$N^0{}_1, \ldots, N^0{}_n$ and $N^1{}_1, \ldots, N^1{}_n$ are exponential scaling parameters;
n ranges from 1 to 4;
K is an overall shifting parameter; and, C(t) is the non-linear, time-dependent response to the test input at time t;
and, $$kernel \equiv \frac{1 - e^{-\alpha_p C_0}}{1 + (e^{K_p} - 2)e^{-\alpha_p C_0}};$$

wherein, $C_0$ is the initial amount of the test input; $K_p$ is a shifting parameter related to $C_0$; and, $\alpha_p$ is shifting and scaling parameter related to $C_0$;

and, using the model to obtain the non-linear, time-dependent test response to the test input.

2. The method of claim 1, wherein the system is an environmental system and the component is selected from the group consisting of air, water, and soil.

3. The method of claim 1, wherein the system is a mammal, and the component is selected from the group consisting of a cell, a tissue, an organ, a DNA, a virus, a protein, an antibody, a bacteria.

4. The method of claim 1, wherein the system is a chemical system.

5. The method of claim 1, wherein the system is a mechanical system.

6. The method of claim 1, wherein the system is an electrical system.

7. A non-compartmental method of predicting a non-linear, time-dependent response of a component of a mammalian system to an input into the system, the method comprising:
   selecting a component of the system, the component selected from the group consisting of a cell, a tissue, an organ, a DNA, a virus, a protein, an antibody, a bacteria;
   selecting a set of actual inputs, the set of actual inputs having an element selected from the group consisting of a DNA, a virus, a protein, an antibody, a bacteria, a chemical, a dietary supplement, a nutrient, and a drug;
   obtaining a set of non-linear, time-dependent actual responses of the component to the set of actual inputs;
   using the set of actual inputs and the set of non-linear, time-dependent actual responses to provide a model for predicting a non-linear, test response to a test input, the model comprising the formula $$C(t) = [M_0^0 + M_0^1 (\text{kernel})] + [M_1^0 + M_1^1 (\text{kernel})] \quad (9)$$

$$\left\{ \frac{1 - e^{-[N_1^0 + N_1^1 (\text{kernel})]t}}{1 + (e^K - 2)e^{-[N_1^0 + N_1^1 (\text{kernel})]t}} \right\} + \ldots + [M_n^0 + M_n^1 (\text{kernel})]$$

$$\left\{ \frac{1 - e^{-[N_n^0 + N_n^1 (\text{kernel})]t}}{1 + (e^K - 2)e^{-[N_n^0 + N_n^1 (\text{kernel})]t}} \right\}$$

wherein, $M_0^0, \ldots, M_n^0$ and $M_0^1, \ldots, M_n^1$ are overall scaling parameters;

$N_1^0, \ldots, N_n^0$ and $N_1^1, \ldots, N_n^1$ are exponential scaling parameters;

n ranges from 1 to 4;

K is an overall shifting parameter; and,

C(t) is the non-linear, time-dependent response to the test input at time t;

and, $$\text{kernel} \equiv \frac{1 - e^{-\alpha_p C_0}}{1 + (e^{K_p} - 2)e^{\alpha_p C_0}};$$

wherein, $C_0$ is the initial amount of the test input; $K_p$ is a shifting parameter related to $C_0$; and, $\alpha_p$ is shifting and scaling parameter related to $C_0$;

and, using the model to obtain the non-linear, time-dependent test response to the test input.

8. The method of claim 7, wherein the component is blood.

9. The method of claim 7, wherein the component is a tumor cell.

10. The method of claim 7, wherein the component is a virus.

11. The method of claim 7, wherein the component is a bacteria.

12. The method of claim 7, wherein the non-linear, test response is a bacterial load.

13. The method of claim 7, wherein the non-linear, test response is a viral load.

14. The method of claim 7, wherein the non-linear, test response is a tumor marker.

15. The method of claim 7, wherein the non-linear, test response is a blood chemistry.

16. The method of claim 7, wherein the set of actual inputs includes a set of dosages of a drug.

17. The method of claim 7, wherein the set of actual inputs includes a set of drugs.

18. The method of claim 7, wherein the input is a diabetes drug, and the non-linear, time-dependent response is glucose in the bloodstream.

19. A device for predicting a non-linear, time-dependent response of a component of a physical system to an input into the system, the device comprising:

a processor;

a database for storing a set of actual input data, a set of non-linear, time-dependent actual response data, test input data, and non-linear, time-dependent test response data on a non-transitory computer readable medium;

an enumeration engine on a non-transitory computer readable medium to parameterize a non-compartmental model for predicting a non-linear, test response to a test input, the non-compartmental model comprising the formula $$C(t) = [M_0^0 + M_0^1 (\text{kernel})] + [M_1^0 + M_1^1 (\text{kernel})] \quad (9)$$

$$\left\{ \frac{1 - e^{-[N_1^0 + N_1^1 (\text{kernel})]t}}{1 + (e^K - 2)e^{-[N_1^0 + N_1^1 (\text{kernel})]t}} \right\} + \ldots + [M_n^0 + M_n^1 (\text{kernel})]$$

$$\left\{ \frac{1 - e^{-[N_n^0 + N_n^1 (\text{kernel})]t}}{1 + (e^K - 2)e^{-[N_n^0 + N_n^1 (\text{kernel})]t}} \right\}$$

wherein, $M_0^0, \ldots, M_n^0$ and $M_0^1, \ldots, M_n^1$ are overall scaling parameters;

$N_1^0, \ldots, N_n^0$ and $N_1^1, \ldots, N_n^1$ are exponential scaling parameters;

n ranges from 1 to 4;

K is an overall shifting parameter; and,

C(t) is the non-linear, time-dependent response to the test input at time t;

and, $$\text{kernel} \equiv \frac{1 - e^{-\alpha_p C_0}}{1 + (e^{K_p} - 2)e^{\alpha_p C_0}};$$

wherein, $C_0$ is the initial amount of the test input; $K_p$ is a shifting parameter related to $C_0$; and, $\alpha_p$ is shifting and scaling parameter related to $C_0$;

and, a transformation module on a non-transitory computer readable medium to transform the test data into the non-linear, time-dependent response data using the non-compartmental model.

20. The device of claim 19, wherein the system is an environmental system and the component is selected from the group consisting of air, water, and soil.

21. A device for predicting a non-linear, time-dependent response of a component of a mammalian system to an input into the system, the device comprising:

a processor;

a database for storing a set of actual input data, a set of non-linear, time-dependent actual response data, test input data, and non-linear, time-dependent test response data on a non-transitory computer readable medium;

an enumeration engine on a non-transitory computer readable medium to parameterize a non-compartmental model for predicting a non-linear, test response to a test input, the non-compartmental model comprising the formula $$C(t) = [M_0^0 + M_0^1 (\text{kernel})] + [M_1^0 + M_1^1 (\text{kernel})] \quad (9)$$

$$\left\{ \frac{1 - e^{-[N_1^0 + N_1^1 (\text{kernel})]t}}{1 + (e^K - 2)e^{-[N_1^0 + N_1^1 (\text{kernel})]t}} \right\} + \ldots + [M_n^0 + M_n^1 (\text{kernel})]$$

$$\left\{ \frac{1 - e^{-[N_n^0 + N_n^1 (\text{kernel})]t}}{1 + (e^K - 2)e^{-[N_n^0 + N_n^1 (\text{kernel})]t}} \right\}$$

wherein, $M^0_0, \ldots, M^0_n$ and $M^1_0, \ldots, M^1_n$ are overall scaling parameters;

$N^0_1, \ldots, N^0_n$ and $N^1_1, \ldots, N^1_n$ are exponential scaling parameters;

n ranges from 1 to 4;

K is an overall shifting parameter; and,

C(t) is the non-linear, time-dependent response to the test input at time t;

and, $$\text{kernel} \equiv \frac{1 - e^{-\alpha_p C_0}}{1 + (e^{K_p} - 2)e^{\alpha_p C_0}};$$

wherein, $C_0$ is the initial amount of the test input; $K_p$ is a shifting parameter related to $C_0$;

and, $\alpha_p$ is shifting and scaling parameter related to $C_0$;

and, a transformation module on a non-transitory computer readable medium to transform the test data into the non-linear, time-dependent response data using the non-compartmental model.

22. The device of claim 21, wherein the component is blood.

23. The device of claim 21, wherein the component is a tumor cell.

24. The device of claim 21, wherein the component is a virus.

25. The device of claim 21, wherein the component is a bacteria.

26. The device of claim 21, wherein the non-linear, time-dependent response is a bacterial load.

27. The device of claim 21, wherein the non-linear, time-dependent response is a viral load.

28. The device of claim 21, wherein the non-linear, time-dependent response is a tumor marker.

29. The device of claim 21, wherein the non-linear, time-dependent response is a blood chemistry.

30. The device of claim 21, wherein the device is a handheld device.

* * * * *